US007238473B1

(12) United States Patent
Blackshear et al.

(10) Patent No.: US 7,238,473 B1
(45) Date of Patent: Jul. 3, 2007

(54) TTP-RELATED ZINC FINGER DOMAINS AND METHODS OF USE

(75) Inventors: Perry J. Blackshear, Chapel Hill, NC (US); Wi S. Lai, Durham, NC (US); Ester Carballo-Jane, Durham, NC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 459 days.

(21) Appl. No.: 10/049,586

(22) PCT Filed: Aug. 14, 2000

(86) PCT No.: PCT/US00/22199

§ 371 (c)(1),
(2), (4) Date: Feb. 12, 2002

(87) PCT Pub. No.: WO01/12213

PCT Pub. Date: Feb. 22, 2001

Related U.S. Application Data

(60) Provisional application No. 60/148,810, filed on Aug. 13, 1999.

(51) Int. Cl.
| | | |
|---|---|---|
| C12Q 1/68 | (2006.01) | |
| C12N 9/00 | (2006.01) | |
| G01N 33/53 | (2006.01) | |
| G01N 33/00 | (2006.01) | |
| C07K 1/00 | (2006.01) | |
| C07H 21/04 | (2006.01) | |

(52) U.S. Cl. .................. 435/6; 435/183; 435/501; 435/94; 530/350; 536/23.1; 536/23.5

(58) Field of Classification Search ............ 435/6, 435/91.2, 183; 530/350; 536/23.1, 24.31, 536/24.33
See application file for complete search history.

(56) References Cited

U.S. PATENT DOCUMENTS 6,627,398 B1 * 9/2003 Wilusz et al. ............ 435/6

FOREIGN PATENT DOCUMENTS

WO    WO 97/42820 A      11/1997
WO    WO 97/42820 A1 *   11/1997

OTHER PUBLICATIONS

Akashi et al. Role of AUUUA sequences in stabilization of granulocyte-macrophage colony-stimulating factor RNA in stimulated cells. *Blood* 78:2005-2012 (1991).
Barnard et al. *Nucl. Acids Res.* 21:3580 (1993).
Beelman et al. Degradation of mRNA in eukaryotes. *Cell* 81:179 (1995).
Bohjanen et al. AU RNA-binding factors differ in their binding specificities and affinities. *J. Biol. Chem.* 267:6302-6309 (1992).
Bohjanen et al. An inducible cytoplasmic factor (AU-B) binds selectively to AUUUA multimers in the 3' untranslated region of lymphokine mRNA. *Mol. Cell. Biol.* 11:3288-3295.
Caput et al. Identification of a common nucleotide sequence in the 3'-untranslated region of mRNA molecules specifying inflammatory mediators. *Proc. Natl. Acad. Sci. USA* 83:1670-1674 (1986).
Carballo et al. Bone marrow transplantation reproduces the tristetrapolin-deficiency syndrome in recombination activating gene-2(-/-) mice. *J. Clin. Invest.* 100(5):986-995 (1997).
Carballo et al. Evidence that tristetraprolin is a physiological regulator of granulocyte-macrophage colony-stimulating factor messenger RNA deadenylation and stability. *Blood* 95(6):1891-1899 (Mar. 15, 2000).
Carballo et al. Tristetraprolin is a regulator of granulocyte-macrophage colony-stimulating factor mRNA stability. *Exper. Hematol.* 28(No. 7 Suppl. 1):36 (Jul. 2000).
Carballo et al. Feedback inhibition of macrophage tumor necrosis factor-alpha (TNFα) production by tristetraprolin (TTP), *Science* 281(5379):1001-1005 (Aug. 14, 1998).
Chen et al. AU-rich elements: characterization and importance in mRNA degradation. *Trends Biochem. Sci.* 20:465-470 (1995).
Chen et al. mRNA decay mediated by two distinct AU-rich elements from c-fos and granulocyte-macrophage colony-stimulating factor transcripts: different deadenylation kinetics and uncoupling from translation. *Mol. Cell. Biol.* 15:5777 (1995).
Chen et al. Selective degradation of early-response-gene mRNAs: functional analyses of sequence features of the AU-rich elements. *Mol. Cell. Biol.* 14:8471 (1994).
De et al. Identification of four CCCH zinc finger proteins in *Xenopus*, including a novel vertebrate protein with four zinc fingers and severely restricted expression. *Gene* 228(1-2):133-145 (Mar. 4, 1999).
DuBois et al. Growth factor-inducible nuclear protein with a novel cysteine/histidine repetitive sequence. *J. Biol. Chem.* 265(31):19185-19191 (1990).
Han et al. Interactive effects of the tumor necrosis factor promoter and 3' untranslated regions. *J. Immunol.* 146:1843 (1991).
Kim et al. Binding of a protein to an AU-rich domain of tumor necrosis factor α mRNA as a 35 kDa complex and its regulation in primary rat astrocytes. *Biochem. J.* 316:455-460 (1996).
Lai et al. Interactions of CCCH zinc finger proteins with mRNA. Binding of tristetraprotin-related zinc finger proteins to Au-rich elements and destabilization of mRNA. *J. Biol. Chem.* 275(23):17827:17837 (Jun. 9, 2000).
Lai et al. Evidence that tristetraprolin binds to AU-rich elements and promotes the deadenylation and destabilization of tumor necrosis factor alpha mRNA. *Mol. Cell. Biol.* 19(6):4311-4323 (Jun. 1999).
Ma et al. The yeast homologue YTIS11, of the mammalian TIS11 gene family is a non-essential, glucose repressible gene. *Oncogene* 10:487-494 (1995).

(Continued)

*Primary Examiner*—Bradley L. Sisson
(74) *Attorney, Agent, or Firm*—Needle & Rosenberg, P.C.

(57) ABSTRACT

The present invention provides methods of regulating the destruction of mRNA molecules containing an AU-rich element (ARE), for example, methods of stimulating the degradation of an mRNA molecule encoding TNF-α, and methods of inhibiting the degradation of an mRNA molecule encoding GM-CSF. Also provided are methods for identifying compounds that regulate the destruction of mRNA molecules containing AREs.

11 Claims, 6 Drawing Sheets

OTHER PUBLICATIONS

Muller et al. Association of AUUUA-binding protein with A+U-rich mRNA during nucleo-cytoplasmic transport. *J. Mol. Biol.* 226:721-733 (1992).

Nie et al. ERF-2, the human homologue of the murine Tis11d early response gene. *Gene* 152:285-286 (1995).

Peng et al. Functional characterization of a non-AUUUA AU-rich element from the *c-jun* proto-oncogene mRNA: Evidence for a novel class of AU-rich elements. *Mol. Cell. Biol.* 16(4):1490-1499 (1996).

Rubin et al. A poly (A) binding protein-specific sequence motif: MRTENGKSKGFGFVC binding to mRNA poly (A) and polynucleotides and its role on mRNA translation. *Biochem. Mol. Biol. Int.* 33:575 (1994).

Sachs. Messenger RNA degradation in eukaryotes. *Cell* 74:413 (1993).

Shaw et al. A conserved AU sequence from the 3' untranslated region of GM-CSF mRNA mediates selective mRNA degradation. *Cell* 46:659-667 (1986).

Stevens et al. Blastomeres and cells with mesendodermal fates of carp embryos express cth1, a member of the TIS11 family of primary response genes. *Int. J. Dev. Biol.* 42:181-188 (1998).

Stoecklin et al. Functional hierarchy of AUUUA motifs in mediating rapid interleukin-3 mRNA decay. *J. Biol. Chem.* 269(18):28591-28597 (1994).

Taylor et al. The human TTP protein: sequence, alignment with related proteins, and chromosomal localization of the mouse and human genes. *Nucl. Acids Res.* 19(12):3454 (1991).

Thompson et al. Cloning and characterization of two yeast genes encoding members of the CCCH class of zinc finger proteins: zinc finger-mediated impairment of cell growth. *Gene* 174(2):225-233 (1996).

Varnum et al. The TIS11 primary response gene is a member of a gene family that encodes with a highly conserved sequence containing an unusual Cys-His repeat. *Mol. Cell. Biol.* 11:1754-1758 (1991).

Wang et al. Posttranscriptional regulation of protein expression in human carcinoma cells by adenine-uridine-rich elements in the 3'-untranslated region of tumor necrosis factor-alpha messenger RNA. *Cancer Res.* 57:5426-5433 (1997).

Xu et al. Modulation of the fate of cytoplasmic mRNA by AU-rich elements: key sequence features controlling mRNA deadenylation and decay. *Mol. Cell. Biol.* 17(8):4611-4621 (1997).

Abraham et al., "p55 Tumor necrosis factor receptor fusion protein in the treatment of patients with severe sepsis and septic shock. A randomized controlled multicenter trial. Ro 45-2081 Study Group," JAMA. May 21, 1997;277(19):1531-8.

Achsel and Shimura, "Factors involved in the activation of pre-mRNA splicing from downstream splicing enhancers," J Biochem (Tokyo). Jul. 1996;120(1):53-60.

Agui et al., Stimulation of interleukin-6 production by endothelin in rat bone marrow-derived stromal cells. Blood 84:2531, 1994.

Antman et al.,: Effect of recombinant human granulocyte-macrophage colony-stimulating factor on chemotherapy-induced myelosuppression. N. Engl. J. Med. 319:593, 1988.

Baker EJ, Liggit P: Accelerated poly(A) loss and mRNA stabilization are independent effects of protein synthesis inhibition on alpha-tubulin mRNA in Chlamydomonas. Nuc. Acids. Res. 21:2237, 1993.

Beelman and Parker: Degradation of mRNA in eukaryotes. Cell 81:179, 1995.

Beelman and, Parker: Differential effects of translational inhibition in cis and in trans on the decay of the unstable yeast MFA2 mRNA. J. Biol. Chem. 269:9687, 1994.

Bentley, SA: The role and composition of the adherent layer in long-term bone marrow culture. In: Long term bone marrow culture: proceedings of a symposium held at the Kroc Foundation. Kroc Foundation Series, vol. 18. Alan R. Liss, Inc. New York. 1984.

Beutler "TNF, immunity and inflammatory disease: lessons of the past decade." J Investig Med. Jun. 1995;43(3):227-35.

Beutler B. and T. Brown, "A CAT reporter construct allows ultrasensitive estimation of TNF synthesis, and suggests that the TNF gene has been silenced in non-macrophage cell lines." J Clin Invest. Apr. 1991;87(4):1336-44.

Blackshear, P.J. 1984. Systems for polyacrylamide gel electrophoresis. Methods Enzymol. 104:237-255.

Carballo et al., Phagocytic and macropinocytic activity in MARCKS-deficient macrophages and fibroblasts. Am. J. Physiol. 277:163, 1999.

Cheng et al. "Cachexia and graft-vs.-host-disease-type skin changes in keratin promoter-driven TNF alpha transgenic mice." Genes Dev. Aug. 1992;6(8):1444-56.

Clements et al., "Matrix metalloproteinase expression during experimental autoimmune encephalomyelitis and effects of a combined matrix metalloproteinase and tumour necrosis factor-alpha inhibitor." J Neuroimmunol. Apr. 1997;74(1-2):85-94.

Derigs et al.,: Granulocyte-macrophage colony-stimulating factor expression is regulated at transcriptional and posttranscriptional levels in a murine bone marrow stromal cell line. Exp. Hematol. 22:924, 1994.

Dexter et al., Conditions controlling the proliferation of haemopoietic stem cells in vitro. J. Cell. Physiol. 91:335, 1976.

Dexter et al.,: Maintenance of hemopoietic stem cells and production of differentiated progeny in allogeneic and semiallogeneic bone marrow chimeras in vitro. J. Exp. Med. 145:1612, 1977.

Erickson et al.,: Decreased sensitivity to tumour-necrosis factor but normal T-cell development in TNF receptor-2-deficient mice. Nature 372:560, 1994.

Flach, et al.,. 1994. A yeast RNA-binding protein shuttles between the nucleus and the cytoplasm. Mol. Cell. Biol. 50:1-12.

Fu, X. D. "The superfamily of arginine/serine-rich splicing factors." RNA. Sep. 1995;1(7):663-80.

Gianni et al., Recombinant human granulocyte macrophage colony stimulating factor reduces hematologic toxicity and widens clinical applicability of high dose cyclophosphamide treatment in breast cancer. J. Clin. Oncol. 8:768, 1990.

Godfrey K., "Statistics in practice. Comparing the means of several groups." N Engl J Med. Dec. 5, 1985;313(23):1450-6.

Gomperts et al., 1990. The nucleotide sequence of an EGF-inducible gene indicates the existence of a new family of mitogen-inducible genes. Oncogene 5:1081-1083.

Gozani et al., "A potential role for U2AF-SAP 155 interactions in recruiting U2 snRNP to the branch site." Mol Cell Biol. Aug. 1998;18(8):4752-60.

Greenberger JS: Sensitivity of corticosteroid-dependent insulin-resistant lipogenesis in marrow preadipocytes of obese-diabetic (db/db) mice. Nature 275:752, 1978.

Gueydan et al., 1996. Engagement of tumor necrosis factor mRNA by an endotoxin-inducible cytoplamic protein. Mol. Med. 2:479-488.

Han et al. "Interactive effects of the tumor necrosis factor promoter and 3'-untranslated regions." J Immunol. Mar. 15, 1991;146(6):1843-8.

Han et al., "Complex regulation of tumor necrosis factor mRNA turnover in lipopolysaccharide-activated macrophages." Biochim Biophys Acta. Aug. 27, 1991;1090(1):22-8.

Hattori K. et al., "A metalloproteinase inhibitor prevents lethal acute graft-versus-host disease in mice." Blood. Jul. 15, 1997;90(2):542-8.

Hel et al., 1996. Two distinct regions in the 3' untranslated region of tumor necrosis factor alpha mRNA form complexes with macrophage proteins. Mol. Cell. Biol. 16:5579-90.

Hel et al., 1998. Characterization of the RNA binding proteins forming complexes with a novel putative regulatory region in the 3'-UTR of TNF- mRNA. Nucleic Acids Res. 26:2803-2812.

Hensel et al., "Autocrine stimulation of TNF-alpha mRNA expression in HL-60 cells." Lymphokine Res. 1987 Spring;6(2):119-25.

Heximer et al.,. 1993. A human putative lymphocyte G0/G1 switch gene homologous to a rodent gene encoding a zinc-binding potential transcription factor. DNA & Cell Biol. 12:73-88.

Jacob C. O., "Studies on the role of tumor necrosis factor in murine and human autoimmunity." J. Autoimmun. Apr. 1992;5 Suppl A:133-43.

Jorres A. et al., "Inhibition of tumour necrosis factor production in endotoxin-stimulated human mononuclear leukocytes by the prostacyclin analogue iloprost: cellular mechanisms." Cytokine. Feb. 1997;9(2):119-25.

Katz et al., 1994. AU-A, an RNA-binding activity distinct from hnRNP A1, is selective for AUUUA repeats and shuttles between the nucleus and the cytoplasm. Nucleic Acids Res. 22:238-46.

Keffer et al., "Transgenic mice expressing human tumour necrosis factor: a predictive genetic model of arthritis." EMBO J. Dec. 1991;10(13):4025-31.

Klausner et al., Cell 72, 19 (1993); A. B. Sachs, Cell 74, 413 (1993).

Koeffler et al., Transcriptional and posttranscriptional modulation of myeloid colony-stimulation factor expression by tumor necrosis factor and other agents. Mol. Cell. Biol. 8:3432, 1988.

Kolodziej, P.A., and R.A. Young. 1991. Epitope tagging and protein surveillance. Methods in Enzymology 194:508-519.

Lai et al.,: Rapid insulin-stimulated accumulation of an mRNA encoding a proline-rich protein. J. Biol. Chem. 265:16556, 1990.

Lai, et al., 1998. Characteristics of the intron involvement in the mitogen-induced expression of Zfp-36. J. Biol. Chem. 273:506-517.

Lai, et al.,. 1995. Promoter analysis of Zfp-36, the mitogen-inducible gene encoding the zinc finger protein tristetraprolin. J. Biol. Chem. 270:25266-25272.

Lang et al., TNFα, IL-1α and bFGF are implicated in the complex disease of GM-CSF transgenic mice. Growth Factors 6:131, 1992.

Lewis et al., 1998. Mapping of a minimal AU-rich sequence required for lipopolysaccharide-induced binding of a 55-kDa protein on tumor necrosis factor-_mRNA. J. Biol. Chem. 273:13781-13786.

Lobach et al., "Nucleotide sequence, expression, and chromosomal mapping of Mrp and mapping of five related sequences." Genomics. Jul. 1993;17(1):194-204.

Lorenz H. M. et al., "In vivo blockade of TNF-alpha by intravenous infusion of a chimeric monoclonal TNF-alpha antibody in patients with rheumatoid arthritis. Short term cellular and molecular effects." J. Immunol. Feb. 15, 1996;156(4):1646-53.

Ma et al.,. 1994. The Drosophila TIS11 homologue encodes a developmentally regulated gene. Oncogene 9:3329-3334.

Ma, Q., and H.R. Herschman. 1991. A corrected sequence for the predicted protein from the mitogen-inducible TIS11 primary response gene. Oncogene 6:1277-1278.

Mello et al., 1996. The PIE-1 protein and germline specification in C. elegans embryos. Nature 382:710-712.

Mercer and Wake. 1985. An analysis of the rate of metallothionein mRNA poly(A)-shortening using RNA blot hybridization. Nucleic Acids Res. 13:7929-7943.

Merendino et al., "Inhibition of msl-2 splicing by Sex-lethal reveals interaction between U2AF35 and the 3' splice site AG." Nature. Dec. 16, 1999;402(6763):838-41.

Morimoto et al. "KB-R7785, a novel matrix metalloproteinase inhibitor, exerts its antidiabetic effect by inhibiting tumor necrosis factor-alpha production." Life Sci. 1997;61(8):795-803.

Natesan et al., 1997. Transcriptional squelching re-examined. Nature 390:349-350.

Nemunaitis J: Use of hematopoetic growth factors in marrow transplantation. Curr. Opin. Oncol. 6:139, 1994.

Ning et al.,. "Distinct mechanisms for rescue from apoptosis in Ramos human B cells by signalling through CD40 and interleukin-4 receptor: role for inhibition of an early response gene, Berg36." Biochem Soc Trans. May 1997;25(2):306S.

Odeh "The role of tumour necrosis factor-alpha in acquired immunodeficiency syndrome." J Intern Med. Dec. 1990;228(6):549-56.

Otsuka et al., 1988. Isolation and characterization of an expressible cDNA encoding human IL-3. Induction of IL-3 mRNA in human T cell clones. J. Immunol. 140:2288-2295.

Reimund et al., "Mucosal inflammatory cytokine production by intestinal biopsies in patients with ulcerative colitis and Crohn's disease." J Clin Immunol. May 1996;16(3):144-50.

Rizzuto et al., 1995. Chimeric green fluorescent protein as a tool for visualizing subcellular organelles in living cells. Curr. Biol. 5:635-642.

Ross et al.,: Cytokine messenger RNA stability is enhanced in tumor cells. Blood 77:1787, 1991.

Rothe et al., Mice lacking the tumour necrosis factor receptor 1 are resistant to TNF-mediated toxicity but highly susceptible to infection by listeria monocytogenes. Nature 364:798, 1993.

Rubin HN, Halim MN: Stimulation of globin synthesis by 11-amino acid peptide. Biochem. Mol. Biol. Int. 31:267, 1993.

Sachs, "Messenger RNA degradation in Eukaryotes" ell 74:413-421 (1993).

Schuler GD, Cole MD: GM-CSF and oncogene mRNA stabilities are independently regulated in trans in a mouse monocytic tumor. Cell 55:1115, 1988.

Seydoux et al.,. 1996. Repression of gene expression in the embryonic germ lineage of C. elegans. Nature 382:713-716.

Shalaby et al. "Prevention of the graft-versus-host reaction in newborn mice by antibodies to tumor necrosis factor-alpha." Transplantation. Jun. 1989;47(6):1057-61.

Shaw, G., and R. Kamen. 1986. A conserved AU sequence from the 3' untranslated region of GM-CSF mRNA mediates selective mRNA degradation. Cell 46:659-667.

Shi Y. et al., J. Biol. Chem. 272, 29290 (1997).

Shyu et al., "The c-fos transcript is targeted for rapid decay by two distinct mRNA degradation pathways." Genes Dev. Jan. 1989;3(1):60-72.

Solorzano et al., "A matrix metalloproteinase inhibitor prevents processing of tumor necrosis factor alpha (TNF alpha) and abrogates endotoxin-induced lethality." Shock. Jun. 1997;7(6):427-31.

Spriggs et al., "Phospholipase A2 activation and autoinduction of tumor necrosis factor gene expression by tumor necrosis factor." Cancer Res. Nov. 15, 1990;50(22):7107-7.

Stanley et al., The structure and expression of the murine gene encoding granulocyte-macrophage colony stimulating factor: evidence for utilization of alternative promoters. EMBO J. 4:2569,1985.

Stumpo et al., "Identification of c-fos sequences involved in induction by insulin and phorbol esters." J Biol Chem. Feb. 5, 1988;263(4):1611-4.

Stumpo et al., "MARCKS deficiency in mice leads to abnormal brain developmental and perinatal death." Proc Natl Acad Sci U S A. Feb. 14, 1995;92(4):944-8.

Stumpo et al.;: Molecular cloning, characterization and expression of a cDNA encoding the 80 to 87 kDa myristoylated alanine-rich C kinase substrate: a major cellular substrate for protein kinase C. Proc. Natl. Acad. Sci. USA 86:4012, 1989.

Taylor et al., A pathogenetic role for TNFα in the syndrome of cachexia, arthritis, and autoimmunity resulting from tristetraprolin (TTP) deficiency. Immunity 4:445, 1996.

Taylor et al.,: Mitogens stimulate the rapid nuclear to cytosolic translocation of tristetraprolin, a potential zinc-finger transcription factor. Mol. Endocrinol. 10:140, 1996.

Taylor et al.,: Phosphorylation of tristetraprolin, a potential zinc finger transcription factor, by mitogen stimulation in intact cells and by mitogen activated protein kinase in vitro. J. Biol. Chem. 270:13341, 1995.

te Kronnie et al.,. "Zebrafish CTH1, a C3H zinc finger protein, is expressed in ovarian oocytes and embryos." Dev Genes Evol. Jul. 1999;209(7):443-6.

Thorens et al., Phagocytosis and inflammatory stimuli induce GM-CSF mRNA in macrophages through posttranscriptional regulation. Cell 48:671, 1987.

Tso et al., Isolation and characterization of rat and human glyceraldehyde-3-phosphate dehydrogenase cDNA: genomic complexity and molecular evolution of the gene. Nucl. Acids Res. 13:2485, 1985.

Ulich et al.,. "Haematologic effects of TNF." Res Immunol. Jun. 1993;144(5):347-54.

Vadhan-Raj S, et al., Stimulation of myelopoiesis in patients with aplastic anemia by recombinant human granulocyte macrophage colony stimulating factor. N. Engl. J. Med. 319:1628, 1988.

Van Den Heuvel et al.,: Stromal cells in long-term cultures of liver, spleen and bone marrow at different developmental ages have different capacities to maintain GM-CFC proliferation. Exp. Hematol. 19:115, 1991.

Varnum et al., HR: The TIS11 primary response gene is a member of a gene family that encodes proteins with a highly conserved sequence containing and unusual Cys-His repeat. Mol. Cell. Biol. 11:1754, 1991.

Varnum et al.,: Nucleotide sequence of a cDNA encoding TIS11, a message induced in Swiss 3T3 cells by the tumor promoter tetradecanoyl phorbol acetate. Oncogene 4:119, 1989.

Vogel et al.,: Induction of colony stimulating factor in vivo by recombinant interleukin 1α and recombinant tumor necrosis factor α. J. Immunol. 138:2143, 1987.

Wodnar-Filipowicz A, Moroni C: Regulation of interleukin 3 mRNA expression in mast cells occurs at the posttranscriptional level and is mediated by calcium ions. Proc. Natl. Acad. Sci. USA 87:777, 1990.

Worthington et al., 1996. Metal binding properties and secondary structure of the zinc-binding domain of Nup475. Proc. Natl. Acad. Sci. USA 93:13754-13759.

Wu et al., "Neural tube defects and abnormal brain development in F52-deficient mice." Proc Natl Acad Sci U S A. Mar. 5, 1996;93(5):2110-5.

Xu et al., "Modulation of the fate of cytoplasmic mRNA by AU-rich elements: key sequence features controlling mRNA deadenylation and decay." Mol Cell Biol. Aug. 1997;17(8):4611-21.

Yam et al.,: Cytochemical identification of monocytes and granulocytes. Am. J. Clin. Pathol. 55:283, 1971.

Zhang et al.,. "Cloning and intracellular localization of the U2 small nuclear ribonucloeprotein auxiliary factor small subunit." Proc Natl Acad Sci U S A. Sep. 15, 1992:89(18):8769-73.

Zoja et al., : Interleukin-1β and tumor necrosis factor-α induce gene expression and production of leukocyte chemotactic factors, colony-stimulating factors, and interleukin-6 in human mesangial cells. Am. J. Pathol. 138:991, 1991.

Zorio and Blumenthal, "Both subunits of U2AF recognize the 3' splice site in *Caenorhabditis elegans*." Nature. Dec. 16, 1999;402(6763):835-8.

Zuo and Maniatis, "The splicing factor U2AF35 mediates critical protein-protein interactions in constitutive and enhancer-dependent splicing." Genes Dev. Jun. 1, 1996;10(11):1356-68.

* cited by examiner

1110
GAAUUCACUGGAGCCUCGAAUGUCCAUUCCUGAGUUCUGCAAAGGGAGAGUGGUCAGGUUGC

1197
CUCUGUCUCAGAAUGAGGCUGGAUAAGAUCUCAGGCCUUCCUACCUUCAGACCUUUCCAGAC

1281
UCUUCCCUGAGGUGCAAUGCACAGCCUUCCUCACAGAGCCAGCCCCCCUCUAUUUAUAUUUG 1300                 1325                1350
CACUUAUUAUUUAUUAUUUAUUUAUUAUUUAUUUAUUUGCUUAUGAAUGUAUUUA  SEQ ID NO:24

```
                     10        20        30        40        50        60
hTTP         MDLTAIYESLLSLSPDVPVPSDHGGTESSPG-------WGSSGPWSLS---------PSD
hsERF1(11B)  MTTTLVSATIFDLSEVLCKGNKMLNYSAPSAGGCLLDRKAVGTPAGGG--------FPRR
hsERF2(11D)  MSITLLSA--FYDVDFLCKTEKSLANLNLNN---MLDKKAVGTPVAAAPSSGFAPGFLRR 70        80        90       100       110       120
hTTP         SSPSGVTSRLPGR--------S-TSLVEGR---------------------SCGWVPP
hsERF1(11B)  TSVTLPSSKFHQN--------QLLSSLKG---------------EP----APALSSR
hsERF2(11D)  TSASNLHALAHPAPSPGSCSPKFPGAANGSSCGSAAAGGPTSYGTLKEPSGGGGTALLNK 130       140       150       160       170       180
hTTP         PP-----GHAPLAPRLGPELSPSPTSPTAT--STTPSRYKTELGRTTSESGRCRYGAKCQ
hsERF1(11B)  DSRFRDRSFSHGGER---LLPTQKQ-PGGG--LVNSSRYKIELCRPFELNGACKYGDKCQ
hsERF2(11D)  ENKFRDRSFSENGDRSQHLLHLQQQKGGGSQINSTRYKIELCRPFEESGTCKYGEKCQ
                                                              •   •  •

190       200       210       220       230       240
hHTTP        FAHGLGELRQANRHPKYKTELCHKFYLQGRCPYGSRCHFIHNPSE---------DLAA
hsEFR1(11B)  FAHGIHELRSLIRHPKYKIELCRIFHIIGFCPYGPRCHFIHNAEERR-ALAG--ARDLSA
hsEFR2(11D)  FAHGFHELRSLIRHPKYKIELCRIFHIIGFCPYGPRCHFIHNADERRPAPSGGASGDLRA
                  •            •       •    •   •  •

250       260       270       280       290       300
hTTP         PG-----------HPPVLRQSISFSGLPSGRRTSPPPPGLAGPSLSSSSFSPSSSPPPP
hsEFR1(11B)  D------------RPRLQHSFSHAGFPSAAAT------AAATGLLDS---PTSITPPP
hsEFR2(11D)  FSTRDALHLGFPREPRPKLHHSLSFSGFPSGHHQPPG--GLESPLLLDS---PTSRTPPP 310       320       330       340       350       360
hTTP         G-------DLPSPSAFSAAPGTPLAR----------------------
hsEFR1(11B)  ------------ITSADDLLGSPTLPDGT-------------------
hsEFR2(11D)  PSCSSASSCSSSASSCSSASAASTPSGTPTCCASAAAALRLLYGTGGAEDLLAPGAPCAA 370       380       390       400       410       420
hTTP         ------RDPTPVCCPSCRRATP--------------------------
hsEFR1(11B)  -------NNPFAFSSQELASLFA-------------------------
hsEFR2(11D)  CSSASCANNAFAHG-PELSSLITPLAIQTHNFAAVAAAAYYRSQQQQQQQQGLAPPAQPPA 430       440       450       460       470       480
hTTP         -ISVWGPLGG-----------LVRTPSVQSLGSDP----DEYASSGSSLGGSDSPVFEA
hsEFR1(11B)  -PSMGLPGGG----SP--TTFLFRPMSESPHMFDSPPSPQDSLSDQEGYLSSSSSS--HS
hsEFR2(11D)  PPSATLPAGAAAPPSPPFSFQLPRRLSDSP-VFLAPPSPPDSLSDRDSYLSGSLSSGSLS 490       500
hTTP         GVFAPPQPVAAPRRLPIFNRISVSE   SEQ. ID NO: 1
hsEFR1(11B)  GSDSPT--LDNSRRLPIFSRLSISDD  SEQ. ID NO: 2
hsEFR2(11D)  GSESPS--LDPGRRLPIFSRLSISDD  SEQ. ID NO: 3
```

FIG. 2

```
1281                          1309
CUCUAUUUAUAUUUGCACUUAUUAUUUAUUAUUUAUUUAUUAUUUA
  •                             • ▲   ▲    ▲    ▲   ▲
       1332              1350
   UUUAUUUGCUUAUGAAUGUAUUUA    SEQ ID NO: 25
        •               •
```

```
              10         20         30         40         50         60
XC3H-4      MEISNDSLDLFS------SFFPQLSPPADP-----ETPLLPSFSAP--PKHLSLSSLRY
carp CTH1   MFEISTDNLFLFPIEGLNEAFFPLEGLASG---SLSLAKALLPLVESPSPPMIPWLCSIRY
zebrafish CTH1 MFEISQDDLFIFPIEGLNEAFFPLEGLGGGGGLSLAEALLPLVESPSPPMIPWLCSIRY 70         80         90        100        110        120
XC3H-4      KIELCSRYAESGFCAYRNRCQFAHGLSELRPPVCHPKYKIELCRSFHVLGTLNYGLRCLF
carp CTH1   KIELCSRYAEIGICKYAERCQFAHGLHDLHVPSRHPKYKIELCRIYHIAGYCVYGIRCLF
zebrafish CTH1 KIELCSRYAEIGICKYAERCQFAHGLHDLHVPSRHPKYKIELCRIYHIAGYCVYGIRCLF 130        140        150        160        170        180
XC3H-4      IHSPQERREPPVLPDNLSLPPRRYGGPYRERCRLWSAPGGCPYSARCHFQFPKSARET--
carp CTH1   VHNLKEQR--PVRQRCRNVP---------CRIFRAFGVCPFGIRCHFLHVEGGSESDG
zebrafish CTH1 VHNLKEQR--PIRPRRRNVP---------CRIFRAFGVCPFGIRCHFLHVEGGSESDG 190        200        210        220        230        240
XC3H-4      ---------------CRHFAALGDPYGACCHFSHSPPLDRWGSGTKNSS---
carp CTH1   GEEEQICQPMSQSQEWKPRGALCRIFSAFGFCLYGIRCRFQHGLPNSIKGVNSTHTSWPH
zebrafish CTH1 AEEEQTWQPPSQSQEWKPRGALCRIFSAFGFCLYGIRCRFQHGLPNTIKGHHANHTSWPQ 250        260        270        280        290        300
XC3H-4      -----GSLS--------PSD---------PD-SDPDTPVLSESPANNAFSFSS--
carp CTH1   QMTNRGSLSPVSDACSSQSPPSSVPSVCQGFAVYPEGSGPVIPPSVEAVANNAFTFSSQH
zebrafish CTH1 QMINGSISPISDTCTSPSPPSSSPTSALPSPVYPDSSGPIIPPSVEAVANNAFTFSSQH 310        320        330        340        350
XC3H-4      ---LLLPLALRLQILGDDDLPIASDPLPGDDTDLLPGDEEIAQGLLSVLG   SEQ.ID NO:4
carp CTH1   LNDLLLPLALRLQQLEN---VTNAGPQDAVDKPLLLSLWQDDPRS         SEQ.ID NO:5
zebrafish CTH1 LNDLLLPLALRLQQLEK---AASAGPQDVLDKPLL                SEQ.ID NO:6
```

FIG. 4

```
                           1                                        35
    rat_cmg1       RYKTELCRPF EENGACKYGD KCQFAHGIHE LRSLT
  human_cmg1       RYKTELCRPF EENGACKYGD KCQFAHGIHE LRSLT
  mouse_cmg1       RYKTELCRPF EENGACKYGD KCQFAHGIHE LRSLT
 xenopus_xc3h-2    RYKTELCRPF EENGSCKYGD KCQFAHGIHE LRSLI
  human_tis11d     RLKTELCRPF EESGTCKYGE KCQFAHGFHE LRSLT
  mouse_tis11d     RYKTELCRPF EESGTCKYGE KCQFAHGFHE LRSLT
 xenopus_xc3h-3.1  RYKTELCRPF EENGACKYGE KCQFAHGFHE LRSLT
 xenopus_xc3h-3.2  RYKTELCRPF EESGACKYGE KCQFAHGFHE LRSLT
    human_ttp      RYKTELCRTF SESGRCRYGA KCQFAHGLGE LRQAN
   bovine_ttp      RYKTELCRTF SESGRCRYGA KCQFAHGLGE LRQAN
    mouse_ttp      RYKTELCRTY SESGRCRYGA KCQFAHGLGE LRQAN
     rat_ttp       RYKTELCRTY SESGRCRYGA KCQFAHGPGE LRQAN
 xenopus_xc3h-1    RYKTELCRTF SETGTCKYGA KCQFAHGKIE LREPN
    carp_cth1      RYKTELCSRY AETGTCKYAE RCQFAHGLHQ LHVPS
  zebrafish_cth1   RYKTELCSRY AETGTCKYAE RCQFAHGLHQ LHVPS
 xenopus_xc3h-4    RYKTELCSRY AESGFCAYRN RCQFAHGLSE LRPPV 36                          65
    rat_cmg1       RHPKYKTELC RTFHTIGFCP YGPRCHFIH  ~ SEQ.ID NO:7
  human_cmg1       RHPKYKTELC RTFHTIGFCP YGPRCHFIH  ~ SEQ.ID NO:8
  mouse_cmg1       RHPKYKTELC RTFHTIGFCP YGPRCHFIH  ~ SEQ.ID NO:9
 xenopus_xc3h-2    RHPKYKTELC RTFHTIGFCP YGPRCHFIH  ~ SEQ.ID NO:10
  human_tis11d     RHPKYKTELC RTFHTIGFCP YGPRCHFIH  ~ SEQ.ID NO:11
  mouse_tis11d     RHPKYKTELC RTFHTIGFCP YGPRCHFIH  ~ SEQ.ID NO:12
 xenopus_xc3h-3.1  RHPKYKTELC RTFHTIGFCP YGPRCHFIH  ~ SEQ.ID NO:13
 xenopus_xc3h-3.2  RHPKYKTELC RTFHTIGFCP YGPRCHFIH  ~ SEQ.ID NO:14
    human_ttp      RHPKYKTELC HKFYLQGRCP YGSRCHFIH  ~ SEQ.ID NO:15
   bovine_ttp      RHPKYKTELC HKFYLQGRCP YGSRCHFIH  ~ SEQ.ID NO:16
    mouse_ttp      RHPKYKTELC HKFYLQGRCP YGSRCHFIH  ~ SEQ.ID NO:17
     rat_ttp       RHPKYKTELC HKFYLQGRCP YGSRCHFIH  ~ SEQ.ID NO:18
 xenopus_xc3h-1    RHPKYKTELC HKFYLYGECP YGSRCHFIH  ~ SEQ.ID NO:19
    carp_cth1      RHPKYKTELC RTYHIAGYCV YGTRCLFVH  ~ SEQ.ID NO:20
  zebrafish_cth1   RHPKYKTELC RTYHNAGYCV YVTRCLFVH  ~ SEQ.ID NO:21
 xenopus_xc3h-4    RHPKYKTELC RSFHVLGTCN YGLRCLFIH  ~ SEQ.ID NO:22
```

FIG.5B

TTP-RELATED ZINC FINGER DOMAINS AND METHODS OF USE

The present application is a 35 U.S.C. § 371 national phase application filed from, and claiming priority to, international application PCT/US00/22199, filed Aug. 14, 2000 (published under PCT Article 21(2) in English), which claims priority to U.S. provisional patent application Ser. No. 60/148,810, filed Aug. 13, 1999, which applications are herein incorporated by reference in their entireties.

ACKNOWLEDGMENTS

This invention was made with intramural support from the National Institutes of Health. The government has certain rights in the invention.

FIELD OF THE INVENTION

This invention relates generally to regulation of mRNA stability, for example, to stimulate or inhibit the production of polypeptides involved in disease.

BACKGROUND OF THE INVENTION

The zinc finger protein family encompasses a broad variety of proteins with assorted functions. One relatively uncommon class of zinc finger proteins contains fingers of the Cys-Cys-Cys-His (SEQ ID NO:48) (CCCH) type, in which three cysteines and one histidine are thought to coordinate a single atom of zinc. Members of a very small subclass of the larger family of CCCH zinc finger proteins contain two tandem zinc fingers consisting of $Cx_8Cx_5Cx_3H$ (SEQ ID NO:47) (wherein "x" refers to variable amino acids), spaced exactly 18 amino acids apart. The prototype of proteins of this CCCH double zinc finger subclass is tristetraprolin (TTP), also known as TIS11 and Nup475. TTP is localized to the nucleus of quiescent fibroblasts, but is rapidly phosphorylated on serine residues and translocated to the cytosol after stimulation with serum or other mitogens. TTP is almost completely cytosolic in macrophages.

TTP-deficient mice appear normal at birth, but rapidly develop a wasting syndrome accompanied by erosive arthritis, dermatitis, alopecia, autoantibodies and myeloid hyperplasia. Essentially all of these inflammation-associated conditions can be prevented by the injection of monoclonal antibodies specific for mouse tumor necrosis factor-α (TNF-α), one of the principal mediators of the inflammatory response in mammals.

In addition to its well known role in acute septic shock, TNF-α has been implicated in the pathogenesis of chronic processes such as autoimmunity, graft-versus-host disease, rheumatoid arthritis, Crohn's disease, and the cachexia that accompanies cancer and acquired immunodeficiency syndrome (AIDS). Anti-TNF-α therapies such as neutralizing antibodies against TNF-α and chimeric soluble TNF-α receptors have demonstrated efficacy against some of these conditions in clinical trials.

The present invention is based upon the discovery that the TTP tandem zinc finger domain alone (as well as the analogous domain from other TTP-related polypeptides) is sufficient to bind to an AU-rich element (ARE) within the 3' untranslated region (UTR) of a TNF-α mRNA molecule, thereby targeting the TNF-α mRNA molecule for destruction. The present invention is further based upon the discovery that this mRNA turnover mechanism is not unique to TNF-α mRNA, as destruction of other mRNAs containing AREs, such as the mRNA that encodes granulocyte-macrophage stimulating factor (GM-CSF), is stimulated by the tandem zinc finger domain of TTP and TTP-related polypeptides. Accordingly, the invention provides functional fragments of TTP and TTP-related polypeptides, nucleic acids encoding such functional fragments, and methods of using the nucleic acids and polypeptide fragments to regulate (i.e., stimulate or inhibit) the destruction of mRNAs that contain an ARE. These methods may be used to treat diseases and conditions that are affected by polypeptides encoded by an mRNA molecule whose destruction is modulated by an ARE. The polypeptides and methods of the invention can also be used to identify compounds that regulate the activity of TTP and TTP-related polypeptides, and are therefore useful for regulating levels of mRNA encoding TNF-α, GM-CSF, and other mRNAs containing functional AREs, such as that encoding interleukin-3 (IL-3).

SUMMARY OF THE INVENTION

Described herein are methods based upon the discovery that TTP and TTP-related proteins stimulate the destruction of certain mRNAs by binding to an AU-rich element (ARE) within the 3' untranslated region of such mRNAs, and that the zinc finger domain of TTP and TTP-related proteins is sufficient to mediate this destruction.

In a first aspect, the invention features a method of treating granulocytopenia in a subject, including administering to the subject an agent that inhibits the degradation of GM-CSF mRNA, thereby treating granulocytopenia in the subject.

In various embodiments of the first aspect of the invention, the granulocytopenia is relative or absolute; the degradation of GM-CSF mRNA is inhibited by inhibiting the mRNA degradative activity of TTP; or the agent that inhibits the degradative activity of TTP is a competitor of TTP. For example, the competitor can compete with TTP for binding on the AU-rich element (ARE) of GM-CSF mRNA; or the competitor can compete with TTP for binding on an mRNA degradative enzyme.

In other embodiments of the first aspect of the invention, the degradation of GM-CSF mRNA is inhibited by inhibiting the mRNA degradative activity of ERF1; for example, the agent that inhibits the mRNA degradative activity of ERF1 can be a competitor of ERF1. The competitor can compete with ERF1 for binding on the AU-rich element (ARE) of GM-CSF mRNA; or can compete with ERF1 for binding on an mRNA degradative enzyme.

In still other embodiments of the first aspect of the invention, the degradation of GM-CSF mRNA is inhibited by inhibiting the mRNA degradative activity of ERF2. The agent that inhibits the mRNA degradative activity of ERF2 can be a competitor of ERF2. For example, the competitor can compete with ERF2 for binding on the AU-rich element (ARE) of GM-CSF mRNA, or can compete with ERF2 for binding on an mRNA degradative enzyme.

In a second aspect, the invention features a method of treating granulocytopenia in a subject, including administering to the subject a mutant TTP that has reduced activity compared to wild type TTP. In various embodiments of the second aspect of the invention, the activity of TTP reduced is degradation of GM-CSF mRNA; or the mutant TTP is administered by delivering to the subject a nucleic acid that encodes the mutant TTP and allows expression of the mutant TTP in cells of the subject.

In a third aspect, the invention features a method of treating granulocytopenia in a subject, including administering to the subject a mutant ERF1 that has reduced activity compared to wild type TTP. In various embodiments of the third aspect of the invention, the activity of ERF1 reduced is degradation of GM-CSF mRNA; or the mutant ERF1 is administered by delivering to the subject a nucleic acid that encodes the mutant ERF1 and allows expression of the mutant ERF1 in cells of the subject.

In a fourth aspect, the invention features a method of treating granulocytopenia in a subject, including administering to the subject a mutant ERF2 that has reduced activity compared to wild type TTP. In various embodiments of the fourth aspect of the invention, the activity of ERF2 reduced is degradation of GM-CSF mRNA, or the mutant ERF2 is administered by delivering to the subject a nucleic acid that encodes the mutant ERF2 and allows expression of the mutant ERF2 in cells of the subject.

In a fifth aspect, the invention features a mutant TTP that has a reduced TTP activity compared to wild type TTP. In various embodiments of the fifth aspect of the invention, the activity of TTP reduced is TTP binding to the ARE of GM-CSF mRNA; the activity of TTP reduced is TTP binding to an mRNA degradative enzyme; the activity of TTP reduced is degradation of GM-CSF mRNA; the mutant is C124R; or the mutant is C147R.

In a sixth aspect, the invention features a mutant ERF1 that has a reduced ERF1 activity compared to wild type ERF1. In various embodiments of the sixth aspect of the invention, the activity of ERF1 reduced is ERF1 binding to the ARE of GM-CSF mRNA; the activity of ERF1 reduced is ERF1 binding to an mRNA degradative enzyme; or the activity of ERF1 reduced is degradation of GM-CSF mRNA.

In a seventh aspect, the invention features a mutant ERF2 that has a reduced ERF2 activity compared to wild type ERF2. In various embodiments of the seventh aspect of the invention, the activity of ERF2 reduced is ERF2 binding to the ARE of GM-CSF mRNA; the activity of ERF2 reduced is ERF2 binding to an mRNA degradative enzyme; or the activity of ERF2 reduced is degradation of GM-CSF mRNA.

In an eighth aspect, the invention features a method of screening an agent for the ability to inhibit an activity of TTP, including the steps of: a) cotransfecting a cell with a nucleic acid that encodes TTP and a nucleic acid that includes an ARE downstream of a nucleic acid sequence encoding a reporter protein; b) contacting the cell of step a) with the agent; and c) comparing the expression of the reporter protein in the cell of step b) to the cell of step a) in the absence of the agent, an increase in reporter gene expression in the cells of step b) compared to the cells of step a) indicating that the agent has the ability to inhibit an activity of TTP.

In a ninth aspect, the invention features a method of screening an agent for the ability to compete with TTP for binding to the ARE of mRNA, including the steps of: a) transfecting a cell with a nucleic acid that encodes TTP; b) obtaining a cytosolic extract of the cell of step a); c) contacting the cytosolic extract of step b) with the agent; d) contacting the cytosolic extract of steps b) and c) with a probe including an ARE; e) comparing the binding of the probe to TTP in the cytosolic extract of step b) with the binding of the probe to TTP in the cytosolic extract of step c), the presence of reduced binding of the probe to TTP in the cytosolic extract of step c) indicating an agent that can compete with TTP for binding to the ARE of mRNA.

In a tenth aspect, the invention features a method of stimulating the degradation of an mRNA molecule having an AU-rich element (ARE), including contacting the mRNA molecule with a tandem zinc finger (TZF) polypeptide consisting essentially of the tristetraprolin (TTP) zinc finger domain or including a TTP-like zinc finger domain, thereby stimulating degradation of the mRNA molecule.

In various embodiments of the tenth aspect of the invention, the TTP-like zinc finger domain is selected from the ERF1 zinc finger domain, the ERF2 zinc finger domain, and the XC3H-4 zinc finger domain; the TZF polypeptide is selected from ERF1, ERF2, and XC3H-4; the mRNA molecule is within a cytosolic extract; the mRNA molecule is within a cell; the mRNA molecule is within a patient or subject; the mRNA molecule encodes TNF-$\alpha$; or production of a polypeptide (e.g., TNF-$\alpha$) encoded by the mRNA molecule is decreased.

In other embodiments of the tenth aspect of the invention, the TZF polypeptide is administered to a patient or subject to treat, inhibit, or prevent a TNF-$\alpha$-related disease or condition in the patient or subject; a nucleic acid encoding the TZF polypeptide is administered to a patient or subject to treat, inhibit, or prevent a TNF-$\alpha$-related disease or condition in the patient or subject; or the ARE is a class II ARE.

In an eleventh aspect, the invention features a method of identifying a compound that modulates the activity of TTP or a TTP-like polypeptide, including: a) contacting a sample with the compound, and b) detecting or measuring the binding between an ARE and a TZF polypeptide consisting essentially of a TTP zinc finger domain or a polypeptide including a TTP-like zinc finger domain in the sample, whereby an increase or decrease in the binding between the ARE and the polypeptide, relative to the binding between the ARE and the polypeptide in the sample not contacted with the compound, identifies a compound that modulates the activity of TTP or a TTP-like polypeptide.

In various embodiments of the eleventh aspect of the invention, an increase in the binding between the ARE and the polypeptide identifies a compound that stimulates the activity of a TTP or a TTP-like polypeptide; the method identifies a compound that stimulates degradation of an mRNA molecule including an ARE; the mRNA molecule encodes TNF-$\alpha$; a decrease in the binding between the ARE and the TZF polypeptide identifies a compound that inhibits the activity of TTP or a TTP-like polypeptide; the method identifies a compound that inhibits degradation of an mRNA molecule including an ARE; the mRNA molecule encodes GM-CSF or IL-3; the method further includes contacting the sample with an inhibitor of mRNA transcription prior to detecting or measuring the binding between the ARE and the TZF polypeptide; or the ARE is a class II ARE.

In a twelfth aspect, the invention features a method of identifying a compound that mimics the activity of TTP or a TTP-like polypeptide, including: a) contacting a first sample including an RNA molecule including an ARE with a compound; b) contacting a second sample including an RNA molecule including an ARE with the compound and with a saturating amount of a TZF polypeptide consisting essentially of a TTP zinc finger domain or including a TTP-like zinc finger domain; c) detecting or measuring degradation of the RNA molecule or binding of the compound to the ARE in the first sample and in the second sample; e) comparing the degradation or binding in the first sample to the degradation or binding in the first sample not contacted with the compound; and f) comparing the degradation or binding in the first sample to the degradation or binding in the second sample, whereby an increase in degradation or binding in the first sample contacted with the compound relative to the sample not contacted with the compound, and lack of an increase in degradation or binding in the second sample contacted with the compound and with the saturating amount of a TZF polypeptide, identifies a compound that mimics the activity of TTP or a TTP-like peptide. In one embodiment of the eleventh aspect of the invention, the ARE is a class II ARE.

In a thirteenth aspect, the invention features a polypeptide consisting essentially of a TTP zinc finger domain or a TTP-like zinc finger domain. In various embodiments of the twelfth aspect of the invention, the polypeptide can bind to a class II ARE within an mRNA molecule and stimulate degradation of the mRNA molecule under physiological conditions, or the TTP-like zinc finger domain is from ERF1, ERF2, or XC3H-4.

In a fourteenth aspect, the invention features a nucleic acid consisting essentially of a nucleotide sequence that encodes a TTP zinc finger domain or a TTP-like zinc finger domain. In various embodiments of the thirteenth aspect of the invention, the TTP-like zinc finger domain is from ERF1, ERF2, or XC3H-4.

In a fifteenth aspect, the invention features a vector including the nucleic acid of claim 66, wherein the nucleic acid is operably linked to a promoter for transcription of the nucleic acid.

In a sixteenth aspect, the invention features a mutant XC3H-4 that has a reduced XC3H-4 activity compared to wild type XC3H-4. In various embodiments of the seventh aspect of the invention, the activity of XC3H-4 reduced is XC3H-4 binding to the ARE of GM-CSF mRNA; the activity of XC3H-4 reduced is XC3H-4 binding to an mRNA degradative enzyme; or the activity of XC3H-4 reduced is degradation of GM-CSF mRNA.

In this specification and in the claims that follow, reference is made to a number of terms that shall be defined to have the following meanings.

As used in the specification and the appended claims, the singular forms "a," "an," and "the" include plural referents unless the context clearly dictates otherwise.

In the present invention "comprising" means that at least the elements specified are present. By "containing" is meant that at least the elements specified are present.

By "TTP zinc finger" or "TTP zinc finger domain" is meant a polypeptide fragment of 77 amino acids or less, which has a 64 amino acid sequence identical to the sequence in TTP that contains two CCCH zinc fingers spaced eighteen amino acids apart, as shown in FIG. 5B, and which, by itself, is sufficient to bind to a class II ARE within an mRNA molecule and stimulate degradation of the mRNA molecule.

By "TTP-like zinc finger" or "TTP-like zinc finger domain" is meant a polypeptide fragment that has a 64 amino acid TZF consensus sequence as set forth below, or as shown in FIG. 5B, which is not identical to a TTP zinc finger, and which, by itself, is sufficient to bind to a class II ARE within an mRNA molecule and stimulate degradation of the mRNA molecule.

By "class II ARE" is meant an AU-rich region in the 3'-untranslated region of an mRNA molecule, which contains repeats of the pentanucleotide "AUUUA" sufficient to permit binding of TTP or a TZF polypeptide to stimulate deadenylation and/or degradation of the mRNA molecule. An example of a class II ARE is depicted, e.g., in FIG. 1. Class II AREs are known in the art, and are described, e.g., in Xu et al. *Mol. Cell. Biol.*, 17:4611–4621, 1997.

By "TTP-like polypeptide" or "TZF polypeptide" is meant a polypeptide that displays TTP-like activity, i.e., can bind to a class II ARE and can stimulate deadenylation and/or degradation of an mRNA molecule containing a class II ARE. A TTP-like polypeptide can be a polypeptide consisting of only the 64 amino acid tandem zinc finger (TZF) domain having the TZF amino acid consensus sequence (representatives of which are shown in FIG. 5B), or a TZF polypeptide can be a larger polypeptide comprising the TZF domain (for example, a naturally occurring polypeptide such as ERF1 or ERF2), or the TZF polypeptide may contain the TZF domain plus additional amino acid sequences, as long as the TTP-like polypeptide can carry out its TTP-like activities of binding a class II ARE and stimulating mRNA deadenylation and/or degradation. A polypeptide having the amino acid sequence of full-length human TTP or full-length rodent TTP is excluded from this definition.

A TTP-like polypeptide or TZF polypeptide will contain a 64 amino acid TZF domain having a TZF consensus sequence as follows (see FIG. 5B for numbering strategy; slashes indicate alternative residues; preferred amino acids are denoted by upper case letters and less preferred amino acids are denoted by lower case letters):

| | | |
|---|---|---|
| aa1–aa7: | RYKTELC | (SEQ ID NO: 42) |
| aa8: | R/s | |
| aa9: | P/T/r | |
| aa10: | F/Y | |
| aa11: | E/S/a | |
| aa12: | E | |
| aa13: | S/N/t/s | |
| aa14: | G | |
| aa15: | A/R/T/S/f | |
| aa16: | C | |
| aa17: | K/R/a | |
| aa18: | Y | |
| aa19: | G/a/r | |
| aa20: | E/A/D/n | |
| aa21: | K/R | |
| aa22–aa27: | CQFAHG | (SEQ ID NO: 43) |
| aa28: | L/F/I/p/k | |
| aa29: | H/G/i/s | |
| aa30: | E/D | |
| aa31: | L | |
| aa32: | R/H | |
| aa33: | S/Q/v/e/p | |
| aa34: | L/A/P | |
| aa35: | T/N/s/v | |
| aa36: | R/q | |
| aa37–aa45: | HPKYKTELC | (SEQ ID NO: 44) |
| aa46: | R/H | |
| aa47: | T/K/s | |
| aa48: | F/Y | |
| aa49: | H/Y | |
| aa50: | T/L/n/v | |
| aa51: | I/Q/a/l/y | |
| aa52: | G | |
| aa53: | F/R/y/e/t | |
| aa54: | C | |
| aa55: | P/v/n | |
| aa56: | Y | |
| aa57: | G/v | |
| aa58: | P/S/t/l | |
| aa59–aa60: | RC | |
| aa61: | H/l/n | |
| aa62: | F | |
| aa63: | I/v | |
| aa64: | H | |

Examples of naturally occurring TTP-like (TZF) polypeptides include, but are not limited to: ERF1/CMG1; ERF2/TIS11D/XC3H-3.2; XC3H-3.1; XC3H-1; CTH1 (carp); CTH1 (zebrafish); and XC3-H-4.

By "sample" is meant an animal (e.g., a human or non-human primate, or a domestic, farm, or laboratory animal, such as a horse, dog, cat, bird, ferret, cow, pig, sheep, goat, rat, mouse, rabbit, guinea pig, fish, or frog); a tissue, organ, or body fluid obtained from an animal; a cell (either within an animal or taken directly from an animal, or a cell maintained in culture or from a cultured cell line); a lysate, lysate fraction, or extract (e.g., a cytosolic extract) derived from a cell; a molecule derived from a cell or cellular material (e.g., a polypeptide or nucleic acid molecule); or an experimental reaction mixture (e.g., containing a buffer and salts, substrates, and/or any other molecules needed to carry out an assay) which is to be assayed or analyzed according to the methods of the invention, for example, to identify a compound that modulates the activity of TTP or a TTP-like polypeptide.

By "modulates the activity of TTP or a TTP-like polypeptide" is meant a compound that increases or decreases the binding of TTP or a TTP-like polypeptide (or a TZF polypeptide) to an ARE, e.g. (but not limited to), by binding to either the polypeptide, to an ARE, or to an RNA molecule containing the ARE, or by increasing or decreasing the amount of TTP or TTP-like polypeptide available for binding (e.g., by increasing or decreasing degradation of the polypeptide). The compound either facilitates or blocks binding between the polypeptide and the ARE, thereby stimulating or inhibiting degradation of an mRNA molecule that contains an ARE, and that undergoes degradation that is enhanced by the binding of TTP or a TTP-like polypeptide to the ARE.

By "binding between and ARE and a TZF polypeptide" is meant that the ARE and TZF polypeptide physically interact with each other. The amount of binding can be detected and/or measured by methods described herein or known in the art, either directly (e.g., by gel shift or UV cross-linking assays) or indirectly (e.g., by measuring RNA levels by Northern or RNA dot blot analysis to ascertain the relative amount of mRNA degradation resulting from binding between an ARE within the 3' UTR of an RNA molecule and the TZF polypeptide; or by measuring protein levels by Western analysis or ELISA or reporter enzyme assay to ascertain the relative amount of protein, thus inferring the relative amount of mRNA degradation resulting from binding between an ARE within the 3' UTR of an RNA molecule and the TZF polypeptide).

By "TNF-α-related disease or condition" is meant any disease or condition in which TNF-α plays a role, and in which a decrease in TNF-α would be useful in treating preventing, or slowing the disease. Examples of TNF-α-related diseases or conditions include, but are not limited to: acute septic shock, autoimmunity, graft-versus-host disease, rheumatoid arthritis, Crohn's disease, cachexia associated with cancer or AIDS, wasting syndrome, dermatitis, alopecia, myeloid hyperplasia, and, in general, TNF-α-dependent inflammation.

By "a saturating amount of a TZF polypeptide" is meant an amount of a TZF polypeptide sufficient to induce the maximal amount of degradation of an RNA species that has a class II ARE and whose degradation is stimulated by a TZF polypeptide. The saturating amount of a TZF polypeptide may be in a cell or in a cell-free mixture, e.g., a cytosolic extract or other reaction mixture for identifying compounds that mimic, stimulate, or inhibit the activity of TTP or a TTP-like polypeptide.

BRIEF DESCRIPTION OF THE DRAWINGS

FIG. 2 is a diagram showing a sequence alignment comparing human TTP to two human TTP-like proteins, ERF1 and ERF2.

FIG. 4 is a diagram showing a sequence alignment comparing the TTP-like frog protein XC3H-4 to two related proteins from fish, i.e., carp CTH1 and zebrafish CTH1.

FIG. 5B is a diagram of a sequence alignment of the 64 amino acid tandem zinc finger domain of TTP and TTP-related polypeptides.

DETAILED DESCRIPTION OF THE INVENTION

Figures 1A, 1B:
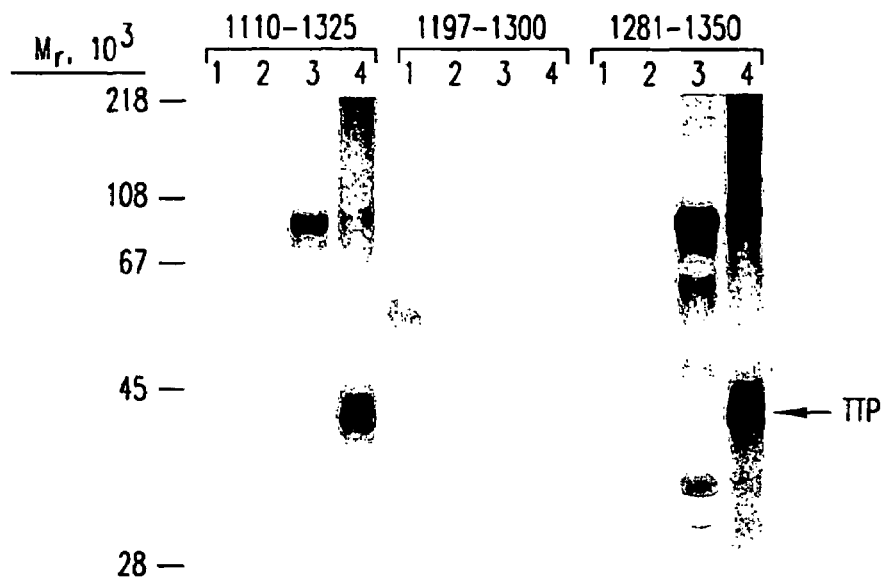
FIG. 1A is a diagram of a UV cross-linking assay showing cross-linking of human TTP with mouse TNFα mRNA ARE probes.
FIG. 1B is a diagram showing the nucleotide sequence of the mouse TNFα ARE probes used in the experiment depicted in FIG. 1A.

The present invention may be understood more readily by reference to the following detailed description of the invention and the Examples included therein.

Before the present compounds and methods are disclosed and described, it is to be understood that this invention is not limited to specific proteins or specific methods. It is also to be understood that the terminology used herein is for the purpose of describing particular embodiments only and is not intended to be limiting.

Described herein are methods based upon the discovery that tristetraprolin (TTP) binds to and destabilizes mRNAs containing a class II AU-rich element (ARE) in their 3' untranslated regions (UTRs). The mRNAs encoding polypeptides such as tumor necrosis factor-alpha (TNF-α), granulocyte-macrophage colony stimulating factor (GM-CSF), and interleukin-3 (IL-3) all contain such AREs and are destabilized by the binding of TTP to the ARE. Described herein are methods for beneficially stimulating or inhibiting degradation of mRNAs containing AREs and methods for identifying additional compounds that are useful for regulating degradation of ARE-containing mRNAs that encode polypeptides involved in disease and inflammation.

Experiments described herein show that TTP binds directly to the ARE of TNF-α mRNA. The integrity of both zinc fingers is required for this direct protein-RNA interaction, since a single mutation of cysteine to arginine within the CCCH motif from either finger abolished TTP's ARE binding activity. The same mutations abrogated the ability of TTP to destabilize the TNF mRNA in intact cells. These experiments show that TTP binds directly to the TNF ARE and destabilizes TNF mRNA in a zinc-finger dependent manner, apparently by initially stimulating mRNA deadenylation.

Two other polypeptides bearing structural similarity to TTP of this subclass have been identified to date in mammals: cMG1 (TIS11b, ERF1, Berg-36) (Barnard et al., Nucleic Acids Res 21:3580, 1993; Gomperts et al., Oncogene 5:1081–1083, 1990; Ning et al., Biochem Soc Trans 25:306S, 1997; and Varnum et al., Mol Cell Biol 11:1754–1758, 1991); and TIS11d (ERF2) (Varnum et al., supra; and Nie et al., Gene 152:285–286, 1995). Like TTP, ERF1/TIS11b and ERF2/TIS11d contain the two typical CCCH fingers, spaced 18 amino acids apart, with the sequence RYKTEL (SEQ ID NO:26) or a variant leading into each finger. Proteins with nearly identical double zinc fingers spaced 18 amino acids apart also have been identified in *Drosophila* and yeast (Ma et al., Oncogene 9:3329–3334, 1994; Ma and Herschman, Oncogene 10:487–494, 1995; and Thompson et al., Gene 174:225–233, 1996).

In addition to the *Xenopus* homologues (see FIG. 5B) of the three mammalian proteins described above, which all contain two tandem zinc fingers (TZFs), also known is a fourth *Xenopus* homologue (XC3H-4) containing two CCCH zinc fingers spaced 18 amino acids apart and preceded by the R(K)YKTEL sequence (SEQ ID NO:27, as well as an additional more carboxyl-terminal pair of CCCH zinc fingers that are more closely spaced and lack the lead-in R(K)YKTEL sequence (SEQ ID NO:27) (De et al., Gene 228:133–145, 1999).

The mammalian and *Xenopus*/fish CCCH proteins described herein comprise the known members of a subclass of vertebrate CCCH proteins in which the following features characterize the tandem zinc finger (TZF) domains: 1) Both fingers within the TZF domain in the four proteins are preceded by a conserved six amino acid lead-in sequence, R(K)YKTEL; 2) Both fingers in all proteins contain the following conserved residues and spacing, Cxx(F/Y)x3GxCxYxx(K/R)CxFxH, where x represents variable amino acids; 3) Both fingers in all proteins are separated by exactly 18 amino acids, i.e., between the terminal H of the first finger and the first C of the second finger. These characteristics are identical in the protein homologues despite their species of origin, ranging from human to *Xenopus laevis;* 4) The three mammalian proteins and their homologues are basic, with overall pIs ranging from 8.75–9.91. In contrast, the *Xenopus* protein XC3H-4 has an overall pI of 5.9; however, the TZF domain itself is basic, with a pI of 9.1, similar to the pIs of the TZF domains from the other three proteins (De et al., Gene 228:133–145, 1999).

As shown herein, the two other known mammalian members of this class of tandem CCCH zinc finger proteins exhibited activities similar to TTP in various assays. Specifically, the rat cMG1 protein, whose homologues include mouse TIS11b, human ERF1, and *Xenopus* XC3H-2, and the *Xenopus* XC3H-3 protein, whose homologues include mouse TIS11d and human ERF2, stimulated the apparent deadenylation and destruction of the TNF mRNA in intact cell transfection experiments. Second, these proteins, as well as a TZF domain from the fourth known vertebrate member of this protein class, *Xenopus* XC3H-4, bound to the ARE of the TNF mRNA in cell-free experiments, as demonstrated by gel shift and UV-light cross-linking experiments. Finally, a 77 amino acid TTP fragment containing the 64 amino acid TZF domain of TTP was sufficient to mediate the TTP effect on TNF mRNA stability in cell transfection experiments, as well as in cell-free gel shift and crosslinking experiments.

In contrast, the hU2AF35 protein exhibited no activity in these assays. This protein, a subunit of the essential mRNA splicing factor hU2AF, contains two related CCCH zinc fingers, present in the protein homologues from human to yeast, but that are separated by 116 amino acids in the human protein. Thus, the mere presence of two zinc fingers of this type does not appear to confer TNF mRNA destabilizing and ARE binding activity, in the absence of the other characteristics of the more closely spaced TZFs of TTP and its relatives.

The finding that TTP and its related proteins all exhibited similar mRNA binding and destabilizing activities indicates that the domain they all hold in common, the 64 amino acid TZF domain, is critical for these activities. That the TZF domain is necessary for these activities is demonstrated by the finding, described herein, that mutation of a single cysteine in either zinc finger to an arginine completely abrogated TTP's ARE-binding and mRNA destabilizing activities. Therefore, although not wishing to be bound by theory, it appears likely that the first step in the effect of TTP to destabilize these mRNAs is its binding to the ARE, since non-binding zinc finger mutants do not stimulate TNF mRNA breakdown in intact cells.

The present experiments demonstrate that a 77 amino acid domain of TTP (SEQ ID NO: 23) that contains the 64 amino acid TZF domain was also sufficient for both ARE binding and TNF mRNA destabilizing activities. Therefore, at present, this 64 amino acid domain is the minimum known TTP sequence required for these activities. The corresponding minimum known ARE sequence required for this binding is 24 bases (nucleotides 1309–1332 in Genbank accession number X02611). Therefore, polypeptides containing TZF domains as described herein may be used in the methods of the invention to treat diseases and conditions involving in which it would be beneficial to regulate destruction of an mRNA molecule whose degradation is stimulated by an ARE. The polypeptides and methods of the invention can also be used to identify compounds that regulate the activity of TTP and TTP-related polypeptides, and are therefore useful for regulating levels of mRNA encoding TNF-α, GM-CSF, and other mRNAs containing functional AREs, such as that encoding interleukin-3 (IL-3). Useful assays for identifying such compounds are described herein.

As demonstrated herein, TTP deficiency has a similar effect on the stability of another mRNA containing a class II ARE, i.e., the mRNA encoding GM-CSF. In particular, there was a marked stabilization of GM-CSF mRNA in bone marrow stromal cells derived from TTP-deficient mice, compared to control cells, indicating that TTP is also a physiological regulator of GM-CSF mRNA stability, and thus, of GM-CSF secretion.

Recombinant GM-CSF has been administered to human patients for a variety of indications, including the bone marrow suppression that accompanies certain forms of chemotherapy, autologous bone marrow transplantation, aplastic anemia, and other neutropenic conditions. The present studies allow the development of new therapeutic approaches for stimulating GM-CSF production, for example, in a patient or subject, by increasing the stability of its mRNA.

Accordingly, a method of treating granulocytopenia in a subject is provided. The method comprises administering to the subject an agent that inhibits the degradation of GM-CSF mRNA. The granulocytopenia may be relative granulocytopenia (reduction in granulocyte count below a level considered to be clinically normal) or absolute granulocytopenia (the absence of granulocytes). Treating granulocytopenia involves an increase in granulocyte count to a normal count or approaching a normal count, or it can involve an increase in granulocyte count that is significant compared to the granulocyte count prior to treatment with the agent. The determination that treatment has occurred can be based on clinical parameters such as those applied by a physician in medical practice or the determination can be based on the measurement of a subclinical parameter that is shown to be a reasonable indicator of clinical improvement.

The patient or subject can be a human or non-human primate, or any animal that experiences granulocytopenia (e.g., a cat, a dog, a horse, a bird, or a rodent) as part of a pathological condition or exposure to a granulocyte-depleting amount of a toxic substance (e.g., a chemotherapeutic agent). Additionally, populations of cells in vitro can be enriched for granulocytes according to the present method. These cells may be from cell culture of they may be primary cells ex vivo. These populations of cells can be used as research tools to study GM-CSF or they can be returned to the subject.

The methods of the invention can be used to treat granulocytopenia of whatever cause, particularly diseases that result from a shortage of granulocytes, by increasing the level of GM-CSF in the treated subject. Diseases that are caused by a shortage of granulocytes include granulocytopenia generally, and, specifically, granulocytopenia associated with cancer chemotherapy; associated with propylthiouracil use; associated with other drug use besides chemotherapeutic agents and propylthiouracil; associated with radiotherapy for marrow ablation for bone marrow transplantation or for other conditions; primary granulocytopenia; aplastic anemia; myelofibrosis and myeloid metaplasia; systemic lupus erythematosus; congenital neutropenia, chronic neutropenic disease, cyclic neutropenia, AIDS, myelodysplastic syndromes, myeloid leukemia, acute myeloid leukemia, other forms of myeloablative treatment. Examples of the clinical parameters that can be used to measure the status of the disease (e.g., treatment) include granulocyte counts, as well as measurement of peripheral blood granulocyte precursors, e.g. band forms, and marrow aspiration or marrow biopsy for myeloid lineage cells. Examples of these methods are well known in the art.

Increased levels of GM-CSF are provided by inhibiting the degradation of GM-CSF mRNA. This is accomplished by inhibiting the mRNA degradative activity of certain proteins identified herein as having GM-CSF mRNA degradative activity.

Herein it is shown that tristetraprolin (TTP) stimulates degradation of GM-CSF mRNA (see, e.g., Examples 1 and 4). Without being bound by theory, the mRNA degradative activity of TTP is likely to be a function of its ability to recruit a deadenylating enzyme into proximity with the GM-CSF mRNA. Thus, an agent that inhibits the degradation of GM-CSF mRNA can be an agent that inhibits the mRNA degradative activity of TTP, for example, a competitor of TTP. A competitor of TTP can compete with TTP for binding to the AU-rich element (ARE) of GM-CSF mRNA, thereby partially or completely inhibiting the binding of TTP (or a TTP-like protein) to the AU-rich element. Alternatively, a competitor of TTP can compete with TTP for binding to an mRNA degradative enzyme (e.g., a deadenylase, exonuclease (e.g., a 3' exonuclease) or endonuclease) that plays a role in TTP-induced GM-CSF mRNA degradation. Examples of the agents that inhibit TTP induced mRNA degradation include certain mutant TTP molecules described herein. Other agents, such as chelators of zinc, can also inhibit TTP's mRNA degradative activity.

As shown herein, members of the ERF1 and ERF2 families of TTP-like proteins also stimulate degradation of TNF-α and GM-CSF mRNA. ERF1 and ERF2 are TTP-like proteins of the CCCH double zinc finger class. There is weak similarity between TTP and ERF1 or ERF2 in the non-zinc finger domains, but they are very similar (highly conserved) in the zinc finger domains, both having a lead-in sequence of R(K)YKTEL (SEQ ID NO:27, and then two zinc fingers, spaced 18 amino acids apart, that each have the composition $Cx_8GxCxYGx(K/R)CxFxH$ (SEQ ID NO: 46), where x represents various amino acids. The cloning of ERF1 and the alignment of human and rat ERF1 are described in Barnard et al., *Nucleic Acids Res.* 21:3580, 1993, and the cloning of ERF2 is described in Nie et al., *Gene* 152:285–286, 1995. ERF1 and ERF2 function analogously to TTP, and therefore, competitors and inhibitors of ERF1 and ERF2 may be identified as described for TTP above.

The 64 amino acid double zinc finger domain of TTP and TTP-related polypeptides (see FIG. 5B) is sufficient to accomplish all of the relevant functions of TTP, i.e. stimulating degradation of TNFα mRNA, interleukin 3 (IL3) mRNA and GM-CSF mRNA in transfection studies in intact cells (see Example 3 for these protocols); binding to the AREs of these three mRNAs in cell-free crosslinking studies; and binding to the AREs in cell-free gel shift studies. The two TTP related proteins, represented by their rat and *Xenopus laevis* homologues, respectively, have the same effect as TTP on all three mRNAs in all three assays. Alignment of the human and *Xenopus* versions of ERF2 are provided in De et al. (Identification of four CCCH zinc finger proteins in *Xenopus*, including a novel vertebrate protein with four zinc fingers and severely restricted expression, *Gene* 228:133–145, 1999).

Therefore, all three known members of this CCCH double zinc finger class can be used in the present methods, as can the subdomains of the three proteins that contain the double zinc finger domain, and thus exhibit all the activities of TTP. Examples of other such proteins that are identified according to the methods taught herein can also be used in the ways taught for TTP, ERF1, and ERF2. For example, a fourth member of the class, XC3H-4 (De et al., *Gene* 228:133–145, 1999), has recently been identified, which contains the double zinc finger domain and appears to possess similar activity to the other members of this class. The relevant protocols for the study of ERF, ERF2 and fragments of TTP are those described in Example 3, except that ERF1 and ERF2, as well as fragments of TTP, were used in place of the full length TTP used in that example.

Further examples of proteins that can act as competitors of TTP for ARE binding, include ERF1 and ERF2 as described above; XC3H-4 and its mammalian putative mammalian homologue; TIAR and TIA-1, the AUF-1 family, HuR, HuC, Hel-N1, HuD, AU-B. In fact, ERF1, ERF2 and XC3H-4 do compete with TTP for ARE binding, but since they have TTP-like activities, they would be less effective in protocols to decrease TTP-induced mRNA degradation. The other proteins in the above list are not expected to have TTP-like activities, and are expected to have an ARE-protective effect due to competition with TTP, ERF1, ERF2 etc. Mutants of TTP, ERF1, ERF2, etc. that do not bind the ARE could still inhibit the activities of wild type TTP, ERF1, ERF2 etc. by interacting with degradative enzymes such as the deadenylases or exonucleases.

A method of treating granulocytopenia in a subject is provided, comprising administering to the subject a mutant TTP that has reduced activity compared to wild type TTP. This method works because the mutant competes with wild type TTP expressed in the cell. The amount of mutant expressed can be measured and its sufficiency to compete with wildtype TTP can be assessed routinely using the methods taught herein. The activity of TTP reduced is degradation of GM-CSF mRNA. The mutant TTP can by administered directly or it can be administered by delivering to the subject a nucleic acid that expresses the mutant TTP in cells of the subject.

Another method of treating granulocytopenia in a subject comprises administering to the subject a mutant ERF1 that has reduced activity compared to wild type ERF1. This method works because the mutant competes with wild type ERF1 or TTP expressed in the cell. The amount of mutant expressed can be measured and its sufficiency to compete with wild type ERF1 can be assessed routinely using the methods taught herein. The activity of ERF1 reduced is degradation of GM-CSF mRNA. The mutant ERF1 can be administered directly or it can be administered by delivering to the subject a nucleic acid that expresses the mutant ERF1 in cells of the subject.

Another method of treating granulocytopenia in a subject comprises administering to the subject a mutant ERF2 that has reduced activity compared to wild type ERF2. This method works because the mutant competes with wild type ERF2 or TTP expressed in the cell. The amount of mutant expressed can be measured and its sufficiency to compete with wild type ERF2 can be assessed routinely using the methods taught herein. The activity of ERF2 reduced is degradation of GM-CSF mRNA. The mutant ERF2 can be administered directly or it can be administered by delivering to the subject a nucleic acid that expresses the mutant ERF2 in cells of the subject.

A mutant TTP that has a reduced TTP activity compared to wild type TTP is provided. In the mutant TTP, the activity of TTP reduced is TTP binding to the ARE of GM-CSF mRNA. Alternatively, in the mutant TTP, the activity of TTP reduced is TTP binding to an mRNA degradative enzyme. The activity of TTP reduced is degradation of GM-CSF mRNA, although the actual activity of the mutant can take place at any point in the degradative pathway. A mutant with this activity is also referred to as a dominant negative mutant.

Examples of the TTP mutant that reduce GM-CSF mRNA degradation include C124R and C147R (coordinates based on the numbering system disclosed in Genbank accession number AAA61240 for human TTP). All the numbering for the TTP mutants describe herein is based on this sequence. These mutants and their activities are described in Example 3. Additional dominant negative mutants of TTP are provided. They include (using the same numbering system) H128K; H166L; F126N; deletion of F164; and insertion of Q after 1165. All are non-binding mutants that exhibit dominant negative activity in assays such as those taught in Example 3.

A mutant ERF1 that has a reduced ERF1 activity compared to wild type ERF1 is provided. In the mutant ERF1, the activity of ERF1 reduced is ERF1 binding to the ARE of GM-CSF mRNA. Alternatively, in the mutant ERF1, the activity of ERF1 reduced is ERF1 binding to an mRNA degradative enzyme. The activity of ERF1 reduced is degradation of GM-CSF mRNA, although the actual activity of the mutant can take place at any point in the degradative pathway. A mutant with this activity is also referred to as a dominant negative mutant.

Examples of mutations in the rat version of ERF1 that are the equivalent of C124R and C147 R of TTP have also been made. The equivalent mutations to human ERF1 are C135R and C158R based on Genbank accession number NP_004917. These are also non-binding and dominant negative mutants as tested in protocols essentially like those described in Example 3, except using the ERF1 mutants rather than TTP.

A mutant ERF2 that has a reduced ERF2 activity compared to wild type ERF2 is provided. In the mutant ERF2, the activity of ERF2 reduced is ERF2 binding to the ARE of GM-CSF mRNA. Alternatively, in the mutant ERF2, the activity of ERF2 reduced is ERF2 binding to an mRNA degradative enzyme. The activity of ERF2 reduced is degradation of GM-CSF mRNA, although the actual activity of the mutant can take place at any point in the degradative pathway. A mutant with this activity is also referred to as a dominant negative mutant.

Active fragments of the TTP, ERF1, ERF2, XC3H-4 and other TTP-like proteins are provided. The fragments can possess the mRNA degradative activity of the full-length molecule or they can compete with the full-length molecule for binding to the ARE, and, thus, inhibit the degradative activity of the full-length molecule. Similarly, fragments of the mutants of these proteins are contemplated. Whether the fragment has a degradative activity or inhibits degradation can be routinely determined using the methods taught herein.

The nucleic acids of this invention (e.g., those encoding wild-type or mutant TTP or TTP-like proteins or fragments thereof) can be administered using in vivo gene therapy techniques (U.S. Pat. No. 5,399,346). With regard to gene therapy applications, the nucleic acid can comprise a nucleotide sequence which encodes a gene product which is meant to function in the place of a defective gene product and restore normal function to a cell which functioned abnormally due to the defective gene product. Alternatively, the nucleic acid may encode a gene product which was not previously present in a cell or was not previously present in the cell at a therapeutic concentration, whereby the presence of the exogenous gene product or increased concentration of the exogenous gene product imparts a therapeutic benefit to the cell and/or to a subject.

For in vivo administration, the cells can be in a subject and the nucleic acid can be administered in a pharmaceutically acceptable carrier. The subject can be any animal in which it is desirable to selectively express a nucleic acid in a cell. In a preferred embodiment, the animal of the present invention is a human. In addition, non-human animals which can be treated by the method of this invention can include, but are not limited to, non-human primates, cats, dogs, birds, horses, cows, goats, sheep, guinea pigs, hamsters, gerbils and rabbits, as well as any other animal in which selective expression of a nucleic acid in a cell can be carried out according to the methods described herein.

In the method described above which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc.

(San Diego, Calif.) as well as by means of a Sonoporation machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver nucleic acid to the infected cells. The exact method of introducing the nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors, and pox virus vectors, such as vaccinia virus vectors. Physical transduction techniques can also be used, such as liposome delivery and receptor-mediated and other endocytosis mechanism. This invention can be used in conjunction with any of these or other commonly used gene transfer methods.

The nucleic acid and the nucleic acid delivery vehicles of this invention, (e.g., viruses; liposomes, plasmids, vectors) can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vehicle may be administered orally, parenterally (e.g., intravenously), by intramuscular injection, by intraperitoneal injection, transdermally, extracorporeally, topically or the like. The exact amount of the nucleic acid or vector required will vary from subject to subject, depending on the species, age, weight and general condition of the subject, the severity or mechanism of any disorder being treated, the particular nucleic acid or vehicle used, its mode of administration and the like.

The compounds of this invention (e.g., nucleic acids. proteins, polypeptides, small molecules) can be administered to a cell of a subject either in vivo or ex vivo. For administration to a cell of the subject in vivo, as well as for administration to the subject, the compounds of this invention can be administered orally, parenterally (e.g., intravenously), by intramuscular injection, by intraperitoneal injection, subcutaneous injection, transdermally, extracorporeally, topically, mucosally or the like.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected composition, possibly in combination with a pharmaceutically acceptable carrier and, in addition, may include other medicinal agents, pharmaceutical agents, carriers, adjuvants, diluents, etc.

Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. A more recently revised approach for parenteral administration involves use of a slow release or sustained release system such that a constant dosage is maintained. See, e.g., U.S. Pat. No. 3,610,795, which is incorporated by reference herein. These compounds can be present in a pharmaceutically acceptable carrier, which can also include a suitable adjuvant. By "pharmaceutically acceptable" is meant a material that is not biologically or otherwise undesirable, i.e., the material may be administered to an individual along with the selected compound without causing substantial deleterious biological effects or interacting in a deleterious manner with any of the other components of the composition in which it is contained.

The exact amount of the compound required will vary from subject to subject, depending on the species, age, weight and general condition of the subject, the particular compound used, its mode of administration and the like. Thus, it is not possible to specify an exact amount for every compound. However, an appropriate amount can be determined by one of ordinary skill in the art using only routine experimentation given the teachings herein.

If ex vivo methods are employed, cells or tissues can be removed and maintained outside the subject's body according to standard protocols well known in the art. The compounds of this invention can be introduced into the cells via known mechanisms for uptake of small molecules into cells (e.g., phagocytosis, pulsing onto class I MHC-expressing cells, liposomes, etc.). The compounds of this invention can also be linked to the homeodomain of Antennapedia for introduction, i.e. internalization of the compound, into cells (Prochiantz, P. "Getting hydrophilic compound into cells: lessons from homeopeptides", Curr. Opin. Neurobiol. 6(5): 629–634.) The cells can then be infused (e.g., in a pharmaceutically acceptable carrier) or transplanted back into the subject per standard methods for the cell or tissue type. Standard methods are known for transplantation or infusion of various cells into a subject.

The invention provides methods of screening an agent for the ability to inhibit an activity of TTP or an activity of TTP-like proteins (e.g., ERF1, ERF2, and XC3H-4). For example, a method of screening an agent for the ability to inhibit an activity of TTP is provided. The method can comprise the steps of: a) co-transfecting a cell with a nucleic acid that encodes TTP and a nucleic acid that comprises a TTP binding sequence (e.g., an ARE) downstream of a nucleic acid sequence encoding a reporter protein; b) contacting the cell of step a) with the agent; and c) comparing the expression of the reporter protein in the cell of step b) to the cell of step a) in the absence of the agent, a reduction of expression in the cells of step b) compared to the cells of step a) indicating that the agent has the ability to inhibit an activity of TTP. Examples of this type of assay are described in Example 2 and Example 3. The steps of the above method can be applied to determine whether an agent can inhibit ERF1 by substituting an ERF1 encoding nucleic acid for a TTP encoding nucleic acid, and by substituting a nucleic acid that contains an ERF1 binding site for the nucleic acid that contains a TTP binding site. Similarly, the method can be used to determine whether an agent can inhibit ERF2, by substituting any ERF2 encoding nucleic acid and nucleic acid with and ERF2 binding sequence for the TTP sequences described above.

A method of screening an agent for the ability to compete with TTP or TTP-like protein (e.g., ERF1, ERF2, XC3H-4, etc.) for binding to the ARE of mRNA is provided. For example, the method can comprise the steps of: a) transfecting a cell with a nucleic acid that encodes an epitope-tagged TTP or untagged TTP in the cell; b) obtaining a cytosolic extract of the cells of step a); c) contacting the cytosolic extract of step b) with the agent or an appropriate control; d) contacting the cytosolic extract of steps b) and c) with a probe from the 3' UTR of an mRNA; e) comparing the bining of the probe to the TTP in the cytosolic extract of step b) with the binding of the probe to the TTP in the cytosolic extract of step c), the presence of reduced binding of the probe to TTP in the cytosolic extract of step c) indicating an agent that can compete with TTP for binding to the ARE of mRNA. TTP binding to ARE probes can be readily demonstrated in cell-free assays, making possible screens for potential inhibitors of this interaction. These steps can be adapted to detect competitors of ERF1, ERF2, XC3H-4 etc. by substituting these molecules for TTP.

A variety of assay methods can be used to determine whether a given compound interferes with TTP or related protein binding to the GM-CSF ARE and the breakdown of GM-CSF mRNA. These would include cell-based experiments, such as the transfection studies in 293 cells cited in Example 3; it can be seen that addition of cell-permeable compounds to the cells that inhibited the TTP-mRNA interaction would result in inhibition of TTP's ability to deadenylate and destroy the mRNA. Such assays could use a variety of more convenient readouts, e.g. luminescent proteins, human growth hormone, chloramphenicol acetyltransferase, beta-galactosidase, etc. Similar cell based studies could also be performed in yeast, where there is considerable precedent for high-throughput screening assays for protein interactions with DNA, RNA and other proteins. Cell-free assays would probably be the most convenient to set up; these would involve extracts from cells expressing TTP or its related proteins (e.g., ERF1, ERF2, etc.) or its active fragments (e.g., the double zinc finger domain), and testing their ability to bind to purified, labeled GM-CSF ARE, assayed by either crosslinking or gel-shift assays as described in the Examples. More conveniently still, these assays could use purified TTP or its active fragments, or purified members of the TTP-related protein class or their active fragments, or fusion proteins expressing TTP or its related proteins or their fragments. All have been shown to be active at binding and crosslinking to the TNFα ARE. These would use variable lengths of sequence of the GM-CSF ARE—e.g., a probe that corresponds to bases 3390–3467 of Genbank accession number X03020, but the experiments with the TNF ARE have shown that this could probably be shortened to a "core" ARE of about 23 bases (bases 1309 to 1332 of Genbank Accession number X02611 and corresponding bases for GM-CSF).

It is also possible to use other assays that interfere with TTP's putative interaction with a deadenylase. Such an enzyme has been recently cloned (Komer C G. Wormington M. Muckenthaler M. Schneider S. Dehlin E. Wahle E. "The deadenylating nuclease (DAN) is involved in poly(A) tail removal during the meiotic maturation of *Xenopus* oocytes" EMBO J. 17, 5427–5437 (1998)), and could be used in cell-free assays. Another recently devised assay (Ford L P. Watson J. Keene J D. Wilusz J. ELAV proteins stabilize deadenylated intermediates in a novel in vitro mRNA deadenylation/degradation system. Genes & Development. 13:188–201, 1999) can be used that uses whole cell extracts to look at deadenylation of the TNF mRNA. Stimulatory effects of TTP on this reaction, and inhibitory effects of the dominant negative mutants are, thus, determined.

Test Compounds

In general, compounds that modulate the activity of TTP and TTP-like polypeptides may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, e.g., Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on the activity of TTP or a TTP-like polypeptide should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits a particular target TTP or TTP-like polypeptide. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions in which it is desirable to regulate or mimic activity of TTP or a TTP-like polypeptide.

The present invention is more particularly described in the following examples, which are intended only to be illustrative, since numerous modifications and variations therein will be apparent to those of ordinary skill in the art.

EXAMPLE 1

TTP is a Regulator of GM-CSF mRNA Deadenylation and Stability

Methods

Mice.

Mice deficient in TTP were generated in our laboratory by interbreeding heterozygous animals as described (12). Genotyping of the offspring was performed by PCR of tail DNA, using a set of primers that span the region of the wild-type gene that was disrupted by the targeting vector, and another set that amplified a fragment of the Neo-cassette inserted in the targeting vector (12). Mice deficient in both TNFα receptors (TNFR) (17, 18) were kindly provided by Dr. Mark W. Moore (Genentech, South San Francisco, Calif.), and were interbred with the TTP heterozygous animals. Genotyping of the offspring was performed by PCR of tail DNA, using primers that span the region of the wild-type genes disrupted by the targeting vectors. Genotyping was also performed using Southern blotting of tail DNA after digestion with BglII and probing for Neo, with a 0.7 kb fragment of the vector PMC1neoPolyA (Stratagene, LaJolla, Calif.); this technique revealed three bands of ~3.5 kb (TNFR1), ~2.5 kb (TTP) and ~2 kb (TNFR2). Triple-heterozygous mice were interbred to yield triple-homozygous offspring. As controls for these animals, animals deficient in both TNFR but containing both TTP alleles were generated. All animals were maintained in autoclaved microisolator cages in a barrier facility. Animal care and all experiments were in accordance with institutional guidelines for animal use.

Culture of Bone Marrow Stromal Cells.

Primary cultures of bone marrow stromal cells were established according to the protocol described by Dexter et al. (19, 20) and modified by Van Den Heuvel et al. (21). Briefly, marrow cells from both femurs were flushed with minimum essential medium alpha (α-MEM) using a 1 ml syringe attached to a 25 G needle. After centrifugation for 5 min at 4° C. at 500 g, the cells were resuspended in 0.15 M ammonium chloride to lyse the red cells. After a 5 min incubation at room temperature, the cells were re-centrifuged as above, and then resuspended in culture medium (α-MEM supplemented with 25% (vol/vol) fetal calf serum (GIBCO BRL, Gaithersburg, Md.), 100 U/ml penicillin, 100 µg/ml streptomycin, 2 mM glutamine, and 1.25 µg/ml fungizone (all additives from GIBCO BRL)). Cells were plated onto 60–100 mm diameter petri dishes, as many plates as required for a given experiment (normally, 5–12 plates/animal), and cultured at 33° C. in a humidified atmosphere containing 5% $CO_2$ for 4 days. After that, the medium was replaced by fresh culture medium and then replaced at weekly intervals until confluence was achieved (usually 4–6 weeks).

For identification of cell types, cells were trypsinized (0.05% trypsin (wt/vol)/0.53 mM EDTA, GIBCO BRL) and replated in the same culture medium at 50,000 cells/well in 4-well Lab-Tek tissue culture chambers (Nunc, Thousand Oaks, Calif.), and incubated for another 48 hrs before performing any of the stains or assays. Morphology was assessed by staining the cells with the Diff-Qick Stain Set (Baxter Healthcare Corporation, McGaw Park, Ill.). Non-specific esterase staining was performed as described (22), using α-naphthyl acetate as a substrate (Sigma Chemical Co., St. Louis, Mo.). Phagocytosis of latex beads was performed for 30 min as previously described (23), using 0.8 µm latex beads (Sigma). Oil red 0 stain was used to identify fat cells. Cells were analyzed and photographed using a Nikon Eclipse 400 microscope (Southern Micro Instruments, Atlanta, Ga.), equipped with an Olympus PM-C35B camera (Olympus America Inc., Lake Success, N.Y.). Uptake of Dil-acetylated LDL (Biomedical Technologies, Inc., Stoughton, Mass.) was used to identify macrophages and endothelial cells, and was performed as described by Agui et al. (24). Cells were analyzed using a Nikon Eclipse 600 microscope (Southern Micro Instruments). At least 500 cells per genotype, in duplicate, were counted in each assay.

Northern Blotting

When indicated, the cells were stimulated with lipopolysaccharide (LPS) (1 µg/ml) (Sigma) or mouse recombinant TNFα (10 ng/ml) (R & D Systems, Inc., Minneapolis, Minn.) for different times, and RNA was extracted with the RNeasy kit from Qiagen, Inc. (Valencia, Calif.), according to the directions provided by the manufacturer. RNA was analyzed by Northern blot as described (25), except that the gels contained 1.5% (w/v) agarose. Filters were sequentially probed with cDNA probes to mouse GM-CSF (plasmid p5'mGM-CSF, containing the sequences of exons I, II, III and part of the exon IV of the mouse GM-CSF (bp 1136–1317, 1415–1456, 2214–2339, 3082–3153 of GenBank accession number X03020), was constructed by RT-PCR using RNA from Raw 264.7 cells treated for 4 hrs. with 1 µg/ml of LPS as the template for RT. The 5' primer for PCR amplification was $^{5'}$gtcgacACTCA-GAGAGAAAGGCTAAGG$^{3'}$ (SEQ ID NO:28), and the 3' primer was $^{5'}$CATTCAAAGGGgatatcAGTCAG$^{3'}$ (SEQ ID NO:29, where the lower case letters indicate the restriction sites for SalI and EcoRV, respectively (the EcoRV site is a naturally occurring site in the mGM-CSF gene). The resulting PCR product was digested with these enzymes and cloned into the SalI, EcoRV and XbaI sites of the vector pSK-(Stratagene). Correct sequence of the plasmid insert was confirmed by dye terminator cycle sequencing (Perkin-Elmer, Foster City, Calif.)) and rat GAPDH (26). The 423 bp SalI-EcoRV insert from the GM-CSF and the 1.3 kb EcoRI insert from the GAPDH cDNAs were isolated from low-melting point agarose gels and random primer labeled with $\alpha$-$^{32}$P dCTP for Northern hybridization.

In the RNA stability experiments, BMSC were cultured in the presence of 1 µg/ml LPS for 2 hrs, after which the LPS-containing medium was removed and replaced by fresh medium containing 5 µg/ml of actinomycin D (Sigma). Cells were then harvested for the preparation of RNA at 15 min intervals, using the Qiagen RNeasy kit as described above. Analysis of Northern blots for TNFα and GAPDH mRNA was performed using PhosphorImager analysis (Molecular Dynamics, Sunnyvale, Calif.); in the case of the GM-CSF mRNA, laser-scanning densitometry was performed using a Zeineh soft laser scanning densitometer (model SL-504-XL, Biomed Instruments Inc., Fullerton, Calif.). This was attempted only when at least one of the peak areas was $\geq 20$ arbitrary densitometry units. RNase H assays were performed as described (16).

Measurement of GM-CSF Secretion

To assess GM-CSF secretion, BMSC were cultured in 24-well plates for 6 weeks, then stimulated with LPS (1 µg/ml) for 24 hrs, after which the supernatants were removed and stored at −80° C. until used. GM-CSF secretion was assessed by ELISA, using a specific kit for mouse GM-CSF from Endogen (Woburn, Mass.), following the specifications of the manufacturer.

Results

Characteristics of Bone Marrow Stromal Cells (BMSC) from Wild Type and TTP-Deficient Mice.

Although we were not able to detect GM-CSF mRNA expression in primary macrophages by Northern blotting, our previous data suggested that BMSC might be involved in the development of the TTP-deficiency phenotype (13). BMSC are a mixture of fibroblast-like, macrophage-like, endothelial cells and adipocytes that provide the microenvironment and growth factors needed for the normal development of the hematopoietic system (19, 27).

We first examined primary BMSC cultures from wild type (WT) and TTP-deficient mice after 4–6 weeks of culture at 33° C. These conditions maintain the cultures in a nonhematopoietic state, i.e., hematopoietic progenitors do not survive the first stages of the culture, leaving behind purely stromal cells that are still capable of producing hematopoietic growth factors (21). This point was confirmed by the absence of hematopoietic precursors or mature polymorphonuclear cells in the stained cultures. To evaluate the relative proportions of each cell type in the cultures, we performed a series of specific assays. Dil-acetylated LDL is avidly taken up by macrophages and endothelial cells, which can be then differentiated by morphology (24). Using this assay, WT cultures contained 64% positive cells, while TTP-deficient cultures contained 60% positive cells. The negative cells in these cultures are considered to be fibroblast-like cells (24). Non-specific esterase is a selective cytochemical stain for macrophages (22). Using this method, 47% cells were positive in the WT cultures and 48% in the TTP-deficient cultures. Macrophages are also highly phagocytic for latex beads. In these cultures, 41% of the WT cells and 39% of the TTP-deficient cells were phagocytic for latex beads. The use of oil red O stain, specific for fat cells, revealed that fewer than 1% of cells were fat cells in both WT or TTP-deficient cultures (24, 28). Taken together, these results indicate that the relative proportions of each cell type were comparable between WT and TTP-deficient cultures. Thus, the differences observed between the two genotypes with respect to GM-CSF production were not likely to be due to differences in the proportions of different cell types in the cultures.

Expression of GM-CSF mRNA in Bone Marrow Stromal Cells from WT and TTP-Deficient Mice.

After the BMSC became confluent, they were stimulated with either LPS (1 µg/ml) or TNFα (10 ng/ml), and the effect of these factors on GM-CSF mRNA accumulation was studied over a period of 8 hrs. When comparing wild type (WT) and knockout (KO) samples or heterozygous (Htz) and KO samples, identical amounts of total cellular RNA were subjected to electrophoresis in parallel gels; blotting was performed in parallel; and both were hybridized together with the same probe and exposed to film in the same autoradiography cassette. LPS induced detectable levels of GM-CSF mRNA in WT cells within 2 hrs; these levels peaked at 3 hrs and then slowly decreased over the next several hours, with a slight increase at 8 hrs. GM-CSF mRNA does not appear as a single species in these cells, but as two major components of approximately 1.0 and 0.8 kb, as previously described (29). When an identical study was performed with cells derived from the TTP-deficient mice, however, there were several differences in the pattern of GM-CSF mRNA expression. First, the GM-CSF mRNA was detectable earlier in the TTP-deficient cells (after 1 hr of exposure to LPS); second, the overall accumulation of GM-CSF mRNA at the peak time (3 hrs) appeared to be approximately two-fold greater in the TTP-deficient cells than in the WT cells (after normalizing for GAPDH mRNA expression); and third, the distribution of the two major mRNA species was different. In the WT cells, the average proportion of the lower band, expressed as percentage of the total GM-CSF mRNA, was 40±3% (mean±S.E.M. of 7 values); in contrast, the lower band from the TTP-deficient cells contained only 16±1% (mean±S.E.M. of 8 values) of the total (p<0.0001 when compared to WT values by Student's t test).

When TNFα was used as the stimulus, these differences were even more pronounced. The total amount of GM-CSF mRNA accumulation was much greater (approximately 5-fold at the time of the greatest difference, i.e., 5 hrs) than that seen in the control cells (in this case, derived from a heterozygous (Htz) mouse). In addition, GM-CSF mRNA expression was detected earlier (45 min) and remained detectable at identical autoradiographic exposures for a much longer period (up to 8 hrs in the KO, versus 5 hrs in the Htz cells). Finally, almost no smaller form of GM-CSF mRNA was detectable in the TTP-deficient cells (46±4% in the Htz (n=7) versus 11±2% (n=9) in the KO cells, p<0.0001).

GM-CSF mRNA Adenylation State in BMSC from WT and TTP-Deficient Mice.

Because TTP has been shown to promote the deadenylation of a synthetic modified TNFα mRNA in a co-transfection system (16), we determined whether the smaller GM-CSF mRNA species that was prominent in the WT and Htz cells but nearly absent in the TTP-deficient cells was the deadenylated form of the GM-CSF mRNA. RNase H treatment on selected samples of GM-CSF mRNA. After hybridization with oligo (dT) and digestion with RNase H to remove any remaining polyA tails, the RNA was analyzed by Northern blot. The addition of RNase H completely eliminated the larger species of GM-CSF mRNA, leaving only a single form that co-migrated exactly with the smaller band present in the Htz cells but almost absent in the TTP-deficient cells. This result establishes that the two major forms of GM-CSF mRNA observed in the WT and Htz cells, as well as in earlier studies (29), correspond to the polyadenylated and deadenylated forms of GM-CSF mRNA, respectively, and that the absence of TTP results in a marked increase in the proportion of the polyadenylated form relative to the deadenylated form. By comparing the migration position of the two bands with RNAs of known size, we estimate that the polyA tail of the fully polyadenylated form was approximately 220 residues long in these cells.

Half-Life of GM-CSF mRNA in BMSC from WT and TTP-Deficient Mice.

Because deadenylation is a process associated with the initiation of mRNA degradation (30), we next evaluated the half-life of GM-CSF mRNA in BMSC from WT and TTP-deficient mice. After incubation of BMSC with LPS for 2 hrs followed by the addition of actinomycin D (5 µg/ml), there was a gradual disappearance of GM-CSF mRNA from the WT cells, with an estimated half-life of 111 min. In contrast, in the TTP-deficient cells there was essentially no disappearance of the GM-CSF mRNA over the 60 min period of actinomycin D treatment, with no calculable half-life. These data confirm that the absence of TTP results in an increase in the stability of GM-CSF mRNA. As in the previous experiments, the proportion of GM-CSF mRNA in the smaller, deadenylated form was much greater (32±2%) in the WT (n=5) than in the TTP-deficient cells (8±0.3%) (n=5) (p<0.0001). Although we cannot exclude effects of TTP-deficiency on transcription of the GM-CSF gene, these results demonstrate that both GM-CSF mRNA stability and the proportion of the message in the fully polyadenylated form are increased in the BMSC from the TTP-deficient mice.

To test for the specificity of this effect, we probed the same filters with cDNAs for both TNFα and c-fos. There was increased stability of TNFα mRNA in the TTP-deficient BMSC, confirming our previous results in macrophages (11); in the BMSC, the calculated half-life for TNFα mRNA in the WT cells was 35 min, versus 90 min in the TTP-deficient cells. There was also the apparent absence of a stable, deadenylated intermediate form of the TNFα mRNA, in contrast to the results with GM-CSF mRNA. When similar studies were performed with c-fos mRNA, another short-lived mRNA that contains a so-called class I ARE (31), the estimated half-life of the mRNA was 43 min in the WT cells versus 41 min in the TTP-deficient cells. These results suggest but do not prove that the TTP effect is specific to a particular set of mRNAs, those containing class II AREs.

Secretion of GM-CSF from BMSC from WT and TTP-Deficient Mice.

Our previous results with TNFα showed that the increased stability of TNFα mRNA was accompanied by increased secretion of the protein (13). To determine whether a similar situation occurred with GM-CSF, we incubated confluent layers of BMSC in the presence of LPS (1 μg/ml) for 24 hrs, and measured the amount of GM-CSF secreted into the culture medium using a specific ELISA. There were no statistically significant differences between the levels of GM-CSF secreted by WT and TTP-deficient BMSC in basal, unstimulated conditions, but the levels were barely detectable in this assay. On the other hand, after 24 hrs of stimulation with LPS, the medium from the WT cells contained 2.5±0.6 pg of GM-CSF/ml/μg of DNA (mean±S.E.M. of 5 samples), versus 14.6±4.5 pg of GM-CSF/ml/μg of DNA in the medium from the TTP-deficient cells (5 samples). This 5.8-fold difference was statistically significant ($p<0.05$ using Student's t test). This result suggested that, as in the case of TNFα (11, 13), the absence of TTP resulted not only in an increase in the stability of GM-CSF mRNA, but also in the increased production of GM-CSF from these cells.

Effect of TNFα Receptor Deficiency on GM-CSF mRNA Stability in TTP-Deficient Mice.

TNFα is well known as an inducer of GM-CSF synthesis (32–35); it has also been shown to increase the stability of GM-CSF mRNA (33). Therefore, there was a theoretical possibility that in the TTP-deficient cells, the increased stability of GM-CSF mRNA could be secondary to the excess circulating TNFα levels that characterize these animals. To test this possibility, we generated mice that were deficient in TTP as well as in the two TNFα receptors (triple KO mice). In these mice, any phenotypic changes observed should be due to factor(s) other than TNFα.

To determine whether BMSC from the triple KO mice exhibited stabilized GM-CSF mRNA relative to their controls (animals lacking both TNFα receptors, but WT for TTP), LPS stimulation with and without actinomycin D was performed on their BMSC. In the absence of both TNFα receptors, GM-CSF mRNA levels in the BMSC changed in response to LPS in the same way as in the WT cells, appearing as two species of approximately 1.0 kb and 0.8 kb. However, in the triple KO cells, when TTP was also absent, a pattern identical to that observed in the TTP-deficient mice was seen, i.e., essentially the only form of GM-CSF mRNA present in these cells was the larger, polyadenylated species. In the double KO cells, the deadenylated form represented an average of 41±6% (n=3) of the total GM-CSF mRNA versus 7.5±0.4% (n=4) in the triple KO cells ($p<0.0005$). There was also marked accumulation of total hybridizeable mRNA in the triple KO cells compared to the double KO cells, with an approximately 4-fold increase observed at 3 hrs. Studies of GM-CSF mRNA stability after actinomycin D confirmed that the absence of TTP resulted in a prolonged half-life of GM-CSF mRNA, particularly the polyadenylated form, even in the absence of both TNFα receptor subtypes. In this experiment, the smaller, deadenylated form represented 40±5% (n=5) of the total GM-CSF mRNA in the double KO cells versus 6.1±0.9% (n=5) in the triple KO cells ($p<0.0001$). The calculated half-life of GM-CSF mRNA in the double KO cells was 63 min, but no decay was observed in the triple KO cells. These results establish that the absence of TTP per se is sufficient to inhibit deadenylation and increase the stability of GM-CSF mRNA, even in the absence of TNFα signaling.

The most important finding of the present study is that TTP appears to be a normal, physiological regulator of GM-CSF mRNA stability in the mouse. Using BMSC derived from TTP-deficient mice, we showed that GM-CSF mRNA accumulation was markedly enhanced in cells lacking TTP relative to control cells after stimulation with either LPS or TNFα. Using the transcription inhibitor actinomycin D, it was demonstrated that this increased mRNA accumulation was due, at least in part, to an increase in GM-CSF mRNA stability in the TTP-deficient cells relative to control cells. These data and the data in Examples 2 and 3 indicate that cellular levels of both TNFα and GM-CSF mRNA are controlled to some extent by TTP. As in the case of TNFα, this leads to increased expression of GM-CSF protein from the TTP-deficient cells compared to control cells.

Concerning the mechanism of this effect, the TNFα, GM-CSF and interleukin-3 (IL-3) AREs are all so-called class II AREs, which contain several, usually tandem, AUUUA repeats. Co-transfection experiments in 293 cells, using artificial constructs in which the c-fos promoter was used to drive expression of the β-globin protein coding sequence linked to a 3'-ARE derived from either the TNFα or GM-CSF mRNA, revealed that TTP expression led to decreased accumulation of these "mRNAs", implicating the AREs in this process. In addition, when the half-life of c-fos mRNA, which contains a class I ARE, was estimated in the WT and TTP-deficient BMSC, there was no difference between the two genotypes, suggesting possible specificity of TTP for class II AREs. Direct binding studies demonstrated that TTP could bind directly to the TNFα ARE (see Examples 2 and 3). In additional co-transfection studies, TTP expression led to the destabilization of a somewhat truncated TNFα mRNA, in which the ARE was shortened from seven AUUUA repeats to 3.5, and the spacing between the ARE and a synthetic polyA tail of 33 residues was decreased to 0 b from the normal 300 b in the mouse (GenBank accession number X02611) (16). This TTP-induced mRNA destabilization was accompanied by the formation of a deadenylated intermediate. Thus, a primary role of TTP is to stimulate initially the process of deadenylation and ultimately the overall degradation of the mRNA.

Data from the present study firmly establish a physiological role for TTP as a promoter of GM-CSF mRNA deadenylation. In support of this conclusion are several types of data. First, in every experiment (n=5) in which BMSC from normal mice were used, Northern blotting of GM-CSF mRNA revealed that a substantial proportion (32–45%) of the total GM-CSF mRNA was in a smaller form of approximately 0.8 kb, with the remainder in a larger form (approximately 1 kb). The existence of these two hybridizing forms of GM-CSF mRNA in mouse cells has long been noted in the literature (29, 37), and has been assumed to be due to use of alternate promoters or alternative transcription start sites. Using RNase H with oligo (dT), it was demonstrated that the smaller of the two species represented completely deadenylated GM-CSF mRNA. Thus, the larger of the two species is likely to contain the full polyA tail, calculated to be approximately 220 residues long in these cells. Although the two predominant species were routinely detected on Northern blots, between them on most blots there was a "smear" of intermediate-sized species, presumably representing partially deadenylated mRNA.

Second, in every experiment (n=5) performed with BMSC derived from TTP-deficient mice, there was marked accumulation of the larger, fully polyadenylated form of the GM-CSF mRNA relative to the smaller form, which represented only 6–16% of the total GM-CSF mRNA. This is strong evidence that the normal control of GM-CSF deadenylation is regulated in some manner by TTP. Also, TTP binds and can be crosslinked to the normal, but not ARE-deleted, GM-CSF 3' UTR probes in cell-free studies. Co-transfection of plasmids expressing TTP with those expressing GM-CSF in human 293 cells also led to increased deadenylation of the mRNA and destruction of the mRNA body. These results demonstrate that TTP binds to the GM-CSF mRNA ARE and causes its deadenylation and destabilization.

Direct comparisons of translation rates of polyadenylated and deadenylated mRNAs have indicated that the polyA tail is necessary for normal rates of translation of some mRNAs (38–41). In the present studies, not only is total hybridizeable GM-CSF mRNA increased in cells from the TTP-deficient animals, but the 32–45% of the total represented by the deadenylated mRNA species in the cells from the WT animals may not be normally translated.

These studies support a model for the severe inflammatory syndrome that characterizes the TTP-deficient mice, in which the absence of TTP leads to elevations in the steady state levels of mRNA for both TNFα and GM-CSF, as well as the increased secretion of their encoded proteins. Since each cytokine is known to stimulate the secretion of the other, the initial hypersecretion of each could lead to an interacting pathogenetic spiral in which the hypersecretion of each becomes greater with time.

One of the most striking characteristics of the TTP-deficiency syndrome in mice was the exuberant myeloid hyperplasia noted in bone marrow and in extramedullary sites. The present finding that TTP deficiency resulted in elevated levels of GM-CSF mRNA in BMSC, and increased secretion of GM-CSF from these cells, suggested that these and perhaps other cells might oversecrete this growth factor in the TTP KO mice, contributing in turn to the myeloid hyperplasia. In support of this possibility, mice deficient in the two types of TNFα receptor as well as in TTP displayed myeloid hyperplasia, both medullary and extramedullary. Therefore, the myeloid hyperplasia characteristic of the TTP-deficient mice may well be contributed to by chronic overstimulation by a growth-promoting factor such as GM-CSF.

REFERENCES FOR EXAMPLE 1

1. Varnum B C, Lim R W, Sukhatme V P, Herschman H R: Nucleotide sequence of a cDNA encoding TIS11, a message induced in Swiss 3T3 cells by the tumor promoter tetradecanoyl phorbol acetate. Oncogene 4:119, 1989
2. Lai W S, Stumpo D J, Blackshear P J: Rapid insulin-stimulated accumulation of an mRNA encoding a proline-rich protein. J. Biol. Chem. 265:16556, 1990
3. DuBois R N, McLane N W, Ryder K, Lau L F, Nathans D A: Growth factor-inducible nuclear protein with a novel cysteine/histidine repetitive sequence. J. Biol. Chem. 265: 19185, 1990
4. Taylor G A, Lai W S, Oakey R J, Seldin M F, Shows T B, Eddy R L Jr., Blackshear P J: The human TTP protein: sequence, alignment with related proteins, and chromosomal localization of the mouse and human genes. Nucl. Acids Res. 19: 3454, 1991
5. Varnum B C, Ma Q, Chi T, Fletcher B, Herschman H R: The TIS11 primary response gene is a member of a gene family that encodes proteins with a highly conserved sequence containing and unusual Cys-His repeat. Mol. Cell. Biol. 11:1754, 1991
6. Heximer S P, Forsdyke D R: A human putative lymphocyte $G_0/G_1$ switch gene homologous to a rodent gene encoding a zinc-binding potential transcription factor. DNA Cell Biol. 12:73, 1993
7. Thompson M J, Lai W S, Taylor G A, Blackshear P J: Cloning and characterization of two yeast genes encoding members of the CCCH class of zinc finger proteins: zinc finger-mediated impairment of cell growth. Gene 174: 225, 1996
8. De J, Lai W S, Thorn J M, Goldsworthy S M, Liu X, Blackwell T K, Blackshear P J: Identification of four CCCH zinc finger proteins in *Xenopus*, including a novel vertebrate protein with four zinc fingers and severely restricted expression. Gene 228:133, 1998
9. Taylor G A, Thompson M J, Lai W S, Blackshear P J: Phosphorylation of tristetraprolin, a potential zinc finger transcription factor, by mitogen stimulation in intact cells and by mitogen activated protein kinase in vitro. J. Biol. Chem. 270:13341, 1995
10. Taylor G A, Thompson M J, Lai W S, Blackshear P J: Mitogens stimulate the rapid nuclear to cytosolic translocation of tristetraprolin, a potential zinc-finger transcription factor. Mol. Endocrinol. 10:140, 1996
11. Carballo E, Lai W S, Blackshear P J: Feedback inhibition of macrophage tumor necrosis factor-α production by tristetraprolin. Science 281:1001, 1998
12. Taylor G A, Carballo E, Lee D M, Lai W S, Thompson M J, Patel D D, Schenkman D I, Gilkeson G S, Broxmeyer H E, Haynes B F, Blackshear P J: A pathogenetic role for TNFα in the syndrome of cachexia, arthritis, and autoimmunity resulting from tristetraprolin (TTP) deficiency. Immunity 4:445,
13. Carballo E, Gilkeson G S, Blackshear P J: Bone marrow transplantation reproduces the tristetraprolin-deficiency syndrome in recombination activating gene-2 (−/−) mice. J. Clin. Invest. 100:986, 1997
14. Shyu A-B, Greenberg M E, Belasco J G: The c-fos transcript is targeted for rapid decay by two distinct mRNA degradation pathways. Genes Dev. 3:60, 1989
15. Xu N, Chen C-Y A, Shyu A-B: Modulation of the fate of cytoplasmic mRNA by AU-rich elements: key sequence features controlling mRNA deadenylation and decay. Mol. Cell. Biol. 17:4611, 1997
16. Lai W S, Carballo E, Strum J R, Kennington E A, Phillips R S, Blackshear P J: Evidence that tristetraprolin binds to AU-rich elements and promotes the deadenylation and destabilization of tumor necrosis factor alpha mRNA. Mol. Cell. Biol. 19:4311, 1999
17. Rothe J, Lessiauer W, Lötscher H, Lang Y, Koebel P, Köntgen F, Althage A, Zinkemagel R, Steinmetz M, Bluethmann H: Mice lacking the tumour necrosis factor receptor 1 are resistant to TNF-mediated toxicity but highly susceptible to infection by *listeria monocytogenes*. Nature 364:798, 1993
18. Erickson S L, de Sauvage F J, Kikly K, Carver-Moore K, Pitts-Meek S, Gillett N, Sheehan K C F, Schreiber R D, Goeddel D V, Moore M W: Decreased sensitivity to tumour-necrosis factor but normal T-cell development in TNF receptor-2-deficient mice. Nature 372:560, 1994
19. Dexter T M, Allen T D, Lajtha L G: Conditions controlling the proliferation of haemopoietic stem cells in vitro. J. Cell. Physiol. 91:335, 1976
20. Dexter T M, Moore M A S, Sheridan A P C: Maintenance of hemopoietic stem cells and production of differentiated progeny in allogeneic and semiallogeneic bone marrow chimeras in vitro. J. Exp. Med. 145:1612, 1977
21. Van Den Heuvel R, Schoeters G, Leppens H, Vanderborght O: Stromal cells in long-term cultures of liver, spleen and bone marrow at different developmental ages have different capacities to maintain GM-CFC proliferation. Exp. Hematol. 19:115, 1991
22. Yam L T, Li C Y, Crosby W H: Cytochemical identification of monocytes and granulocytes. Am. J. Clin. Pathol. 55:283, 1971
23. Carballo E, Pitterle D M, Stumpo D J, Sperling R T, Blackshear P J: Phagocytic and macropinocytic activity in MARCKS-deficient macrophages and fibroblasts. Am. J. Physiol. 277:163, 1999
24. Agui T, Xin X, Cai Y, Tohru S, Matsumoto K: Stimulation of interleukin-6 production by endothelin in rat bone marrow-derived stromal cells. Blood 84:2531, 1994
25. Stumpo D J, Graff J M, Albert K A, Greengard P, Blackshear P J: Molecular cloning, characterization and expression of a cDNA encoding the 80 to 87 kDa myristoylated alanine-rich C kinase substrate: a major cellular substrate for protein kinase C. Proc. Natl. Acad. Sci. USA 86:4012, 1989
26. Tso J Y, Sun X H, Kao T H, Reece K S, Wu R: Isolation and characterization of rat and human glyceraldehyde-3-phosphate dehydrogenase cDNA: genomic complexity and molecular evolution of the gene. Nucl. Acids Res. 13:2485,
27. Bentley, S A: The role and composition of the adherent layer in long-term bone marrow culture. In: Long term bone marrow culture: proceedings of a symposium held at the Kroc Foundation. Kroc Foundation Series, vol. 18. Alan R. Liss, Inc. New York. 1984
28. Greenberger J S: Sensitivity of corticosteroid-dependent insulin-resistant lipogenesis in marrow preadipocytes of obese-diabetic (db/db) mice. Nature 275:752, 1978
29. Thorens B, Mermod J-L, Vassalli P: Phagocytosis and inflammatory stimuli induce GM-CSF mRNA in macrophages through posttranscriptional regulation. Cell 48:671, 1987
30. Beelman C A, Parker R: Degradation of mRNA in eukaryotes. Cell 81:179,
31. Chen C-Y A, Shyu A-B: Selective degradation of early-response-gene mRNAs: functional analyses of sequence features of the AU-rich elements. Mol. Cell. Biol. 14:8471, 1994
32. Vogel S N, Douches S D, Kaufman E N, Neta R: Induction of colony stimulating factor in vivo by recombinant interleukin 1α and recombinant tumor necrosis factor α. J. Immunol. 138:2143, 1987
33. Koeffler H P, Gasson J, Tobler A: Transcriptional and posttranscriptional modulation of myeloid colony-stimulation factor expression by tumor necrosis factor and other agents. Mol. Cell. Biol. 8:3432, 1988
34. Zoja C, Wang J M, Bettoni S, Sironi M, Renzi D, Chiaffarino F, Abboud H E, Van Damme J, Mantovani A, Remuzzi G, Rambaldi A: Interleukin-1β and tumor necrosis factor-α induce gene expression and production of leukocyte chemotactic factors, colony-stimulating factors, and interleukin-6 in human mesangial cells. Am. J. Pathol. 138:991, 1991
35. Derigs H G, Reifel-Miller A, Kaushansky K, Hromas R A, Boswell H S: Granulocyte-macrophage colony-stimulating factor expression is regulated at transcriptional and posttranscriptional levels in a murine bone marrow stromal cell line. Exp. Hematol. 22:924, 1994
36. Chen C-Y A, Xu N, Shyu A-B: mRNA decay mediated by two distinct AU-rich elements from c-fos and granulocyte-macrophage colony-stimulating factor transcripts: different deadenylation kinetics and uncoupling from translation. Mol. Cell. Biol. 15:5777, 1995
37. Stanley E, Metcalf D, Sobieszczuk P, Gough N M, Dunn A R: The structure and expression of the murine gene encoding granulocyte-macrophage colony stimulating factor: evidence for utilization of alternative promoters. EMBO J. 4:2569, 1985
38. Rubin H N, Halim M N: Stimulation of globin synthesis by 11-amino acid peptide. Biochem. Mol. Biol. Int. 31:267, 1993
39. Baker E J, Liggit P: Accelerated poly(A) loss and mRNA stabilization are independent effects of protein synthesis inhibition on alpha-tubulin mRNA in *Chlamydomonas*. Nuc. Acids. Res. 21:2237, 1993
40. Rubin H N, Halim M N, Leavis P C: A poly (A) binding protein-specific sequence motif: MRTENGKSKGFG-FVC binding to mRNA poly (A) and polynucleotides and its role on mRNA translation. Biochem. Mol. Biol. Int. 33:575, 1994
41. Beelman C A, Parker R: Differential effects of translational inhibition in cis and in trans on the decay of the unstable yeast MFA2 mRNA. J. Biol. Chem. 269:9687, 1994
42. Lang R A, Cuthberson R A, Dunn A R: TNFα, IL-1α and bFGF are implicated in the complex disease of GM-CSF transgenic mice. Growth Factors 6:131, 1992
43. Ulich T R, Shin S S, del Castillo J: Haematologic effects of TNF. Res. Immunol. 144:347, 1993
44. Shaw G, Kamen R: A conserved AU sequence from the 3' untranslated region of GM-CSF mRNA mediates selective mRNA degradation. Cell 46:659, 1986
45. Wodnar-Filipowicz A, Moroni C: Regulation of interleukin 3 mRNA expression in mast cells occurs at the posttranscriptional level and is mediated by calcium ions. Proc. Natl. Acad. Sci. USA 87:777, 1990
46. Ross H J, Sato N, Ueyama Y, Koeffler H P: Cytokine messenger RNA stability is enhanced in tumor cells. Blood 77:1787, 1991
47. Schuler G D, Cole M D: GM-CSF and oncogene mRNA stabilities are independently regulated in trans in a mouse monocytic tumor. Cell 55:1115,
48. Antman K S, Griffin J D, Elias A A, Socinski M A, Ryan L, Cannistra S A, Oette D, Whitley M, Frei E 3rd, Schnipper L E: Effect of recombinant human granulocyte-macrophage colony-stimulating factor on chemotherapy-induced myelosuppression. N. Engl. J. Med. 319:593, 1988
49. Gianni A, Bregni M, Siena S: Recombinant human granulocyte macrophage colony stimulating factor reduces hematologic toxicity and widens clinical applicability of high dose cyclophosphamide treatment in breast cancer. J. Clin. Oncol. 8:768, 1990

50. Nemunaitis J: Use of hematopoietic growth factors in marrow transplantation. Curr. Opin. Oncol. 6:139, 1994

51. Vadhan-Raj S, Buescher S, Broxmeyer H E: Stimulation of myelopoiesis in patients with aplastic anemia by recombinant human granulocyte macrophage colony stimulating factor. N. Engl. J. Med. 319:1628, 1988

EXAMPLE 2

Inhibition of Macrophage TNFα Production by TTP

Mice deficient in tristetraprolin (TTP), the prototype of a recently recognized family of CCCH zinc finger proteins whose members have been identified in organisms ranging from man to yeast (5–8) were developed. Although the TTP-deficient mice appeared normal at birth, they soon developed a complex syndrome of inflammatory arthritis, dermatitis, cachexia, autoimmunity and myeloid hyperplasia. The TTP-deficiency syndrome could be reproduced in recombination activating gene 2 (RAG 2) (−/−) immune-deficient mice by whole bone marrow transplantation from TTP-deficient mice after a lag period of several months, suggesting that transplanted macrophage progenitors might be among the cells responsible for the transplantability of the phenotype (10). Macrophages derived from fetal liver of TTP-deficient mice, or from bone marrow precursors or resident peritoneal macrophages from adult mice, exhibited increased production of TNFα, and increased levels of TNFα mRNA, after stimulation with lipopolysaccharide (LPS) (10). In the best-studied example, bone marrow-derived macrophages from the knockout mice secreted approximately 5-fold more TNFα than the control macrophages after incubation with LPS (1 µg/ml for 4 hrs), while TNFα mRNA levels were elevated about 2-fold in the knockout cells compared to controls (10).

To investigate the mechanism of this effect, we first evaluated the potential influence of TTP on TNFα gene transcription. We co-transfected a human TTP genomic construct, in which the instability-inducing 3'-untranslated region (UTR) of the TTP mRNA (8) was replaced by the 3'-UTR from the human growth hormone mRNA (11), with a TNFα-promoter/chloramphenicol acetyl-transferase (CAT)-reporter construct (Pro-CAT). This construct, which contained 2.3 kb of the mouse TNFα promoter linked to the CAT coding sequence and a 3'-UTR from a human growth hormone cDNA, was generously provided by Dr. Bruce Beutler, University of Texas/Southwestern Medical Center, Dallas, Tex. (12). Transfection of several cell types (chick embryo fibroblasts, NIH 3T3 mouse fibroblasts, and Rat-1 fibroblasts) showed that transfection with the TTP construct led to non-specific "squelching" of several co-transfected expression constructs, including Pro-CAT, SV2CAT (CAT driven by the SV40 promoter), and CAT driven by the *Xenopus* MARCKS gene promoter (13). In DNA dose-response studies in these cells, there was no evidence for preferential inhibition by the TTP constructs of Pro-CAT expression, when compared to the expression of the other co-transfected constructs. In human 293 cells, which express little if any endogenous TTP (11), transfection of TTP constructs did not significantly inhibit the expression of the same co-transfected constructs. When varying amounts of TTP DNA (0–10 µg) were transfected into 293 cells along with Pro-CAT (5 µg), average CAT expression (n=5 experiments) was completely unaffected by 1 and 5 µg of TTP DNA, and was increased by 52% by 10 µg of TTP DNA compared to 10 µg of vector alone; none of these differences was statistically significant, using a paired t test with the Bonferroni correction for multiple comparisons (14). In parallel experiments (n=5) using TTP co-transfection with SV2CAT, TTP DNA at 1, 5 and 10 µg caused statistically insignificant decreases in average CAT expression of 8%, 11% and 17%, respectively. Thus, there was no evidence that TTP specifically inhibited Pro-CAT expression in this cell type, suggesting that the apparent effect of TTP to decrease macrophage TNFα mRNA and protein levels seen in previous studies (10) was not due to inhibited TNFα gene expression.

We next evaluated the effect of TTP-deficiency on the stability of TNFα mRNA, which has a half-life reported to be 12 min in human monocytes (15) and 39 min in the murine macrophage cell line Raw 264.7 (16). In bone marrow-derived macrophages from wild-type (n=6) and TTP-deficient mice (n=6) that were stimulated with LPS (1 µg/ml) (Sigma Chemical Co., St. Louis, Mo.) for 4 hr followed by treatment with actinomycin D (5 µg/ml) (Sigma Chemical Co.), the half-life of TNFα mRNA in the macrophages lacking TTP was significantly increased (85 min) compared to the half-life of 39 min observed in the wild-type cells. The differences between the average TNFα mRNA levels were statistically significant at all times tested after 30 min of actinomycin D treatment, when compared by Student's t test. Northern analysis showed no evidence of stable mRNA degradation products in either the control or TTP-deficient macrophages. Similar studies with TTP (+/−) macrophages showed that TNFα mRNA decayed at the same rate as in wild-type cells, indicating that ~50% of normal cellular TTP concentrations (9) is sufficient to confer normal lability to TNFα mRNA.

These results suggest that TTP regulates TNFα mRNA levels at a post-transcriptional level. When TTP is present in the cells, TNFα mRNA is extremely labile, whereas its stability increases by more than two-fold in the absence of TTP. This increased half-life of TNFα mRNA in macrophages from the TTP-deficient mice is thus likely to be at least one of the factors responsible for the hypersecretion of TNFα by macrophages derived from these mice (10) and for the syndrome of TNFα excess that characterizes the TTP-deficient mice (9, 10).

Early studies on TTP cellular localization in fibroblasts demonstrated a nuclear localization in quiescent cells; the protein was found to either remain in the nucleus (7) or rapidly (<5 min) translocate to the cytosol after mitogen stimulation (17). Our data, however, suggest a potential role for TTP in the cytosol, leading in some way to the destabilization of TNFα mRNA. This possibility was suggested by earlier studies in the murine macrophage cell line Raw 264.7, in which TTP appeared to be predominantly if not exclusively cytosolic (17). To determine the subcellular localization of TTP in normal macrophages under these conditions, cells treated with LPS or TNFα were labeled with $^{35}$S-cysteine, separated into nuclear and cytosolic fractions, and then immunoprecipitated with anti-TTP antibody (17, 18). Both LPS and TNFα caused an increase in TTP labeling 4 hrs after stimulation that appeared to be exclusively cytosolic. Similar studies using Western blotting showed that increases in TTP protein were first detected in the cytosol 30 min after LPS stimulation, and persisted at high levels in the cytosol 2–4 hrs after stimulation. Nuclear TTP was not detectable in either the immunoprecipitation or the Western blot experiments.

These data suggested that TTP might participate in a novel negative feedback loop, in which cytosolic TTP is induced by the same stimuli that induce TNFα in macrophages, leading to instability of the TNFα mRNA and inhibition of TNFα secretion. To test this possibility, we first examined the expression of TTP mRNA in normal mouse bone marrow-derived macrophages stimulated with LPS (1 μg/ml). After LPS treatment, TTP mRNA rapidly accumulated, peaking at 60 min. TNFα mRNA levels also increased, with a somewhat more prolonged time course. We next asked whether TTP was induced in primary macrophages stimulated with TNFα. Exposure of the cells to recombinant murine TNFα (10 ng/ml) (R & D Systems, Inc., Minneapolis, Minn.) resulted in marked increases in TTP mRNA levels, which peaked at 30–60 min; as shown in other studies (19), TNFα induced expression of its own mRNA, with levels peaking at 60–120 min.

Taken together, the results presented here suggest that TTP can regulate TNFα synthesis at a post-transcriptional level by promoting the turnover of TNFα mRNA. This represents a previously unknown negative feedback mechanism for regulating TNFα production. As the above data indicate and previous studies have shown (19), TNFα promotes rather than inhibits its own synthesis and secretion. However, our data indicate that a negative feedback function can be performed instead by TNFα- or LPS-induced TTP. When TTP is absent, as in the TTP-deficient mice, the untrammeled self-stimulating property of TNFα almost certainly leads to the observed rapid downhill course in which many inflammatory processes are activated (9, 10).

TNFα mRNA contains several AU-rich elements (ARE) as well as considerable predicted secondary structure, both of which can influence mRNA stability (20).

To investigate whether the TNFα mRNA ARE was involved in the TTP effect, we co-transfected 293 cells with constructs expressing TTP (21) and constructs (generously provided by Dr. Ann-Bin Shyu, University of Texas, Houston, Tex.) in which the AREs from TNFα, granulocyte-monocyte colony-stimulating factor (GM-CSF) and interleukin 3 (IL3) mRNAs were placed 3' of the c-fos promoter and the β-globin protein coding sequence (22). Co-expression of human TTP (21), either with a genomic construct driven by the native human TTP promoter (5 μg) or with a human TTP cDNA driven by the CMV promoter (5 μg), markedly inhibited mRNA accumulation from all three constructs. Co-transfection with 0.01 μg of the CMV-TTP construct or an unrelated CMV-MLP construct (23) had little or no effect. TTP mRNA was highly expressed in the cells transfected with 5 μg of CMV-driven TTP, was expressed to an intermediate extent after 5 μg of the TTP genomic construct, and was barely detectable after the 0.01 μg concentration of CMV-TTP. Parallel experiments in which a c-fos promoter/chloramphenicol acetyl transferase (CAT) construct (24) was cotransfected with the TTP expression vectors revealed that the c-fos promoter was completely unaffected by the expression of the genomic TTP construct or 0.01 μg of the CMV construct, while it was inhibited by about 30% by 5 μg of the CMV-TTP construct. Both c-fos promoter activity and β-globin mRNA accumulation were also unaffected by co-transfection of a plasmid containing CMV-driven MLP (5 μg).

These results pointed to the ARE as the common element in these constructs responsible for the TTP stimulation of mRNA lability. To test whether TTP affected binding of cellular proteins to this region of the TNFα mRNA, we transfected 293 cells with a construct expressing epitope-tagged human TTP (21), and attempted to cross-link proteins in a cytosolic extract from these cells to a 153 bp probe from the mouse TNFα 3'-UTR (25) that spanned the ARE. In untransfected cells, the radiolabeled mRNA probe was cross-linked to a major protein species of 85 kDa. When extracts from TTP-expressing cells were used in a similar experiment, labeling of the 85 kDa protein decreased while a new binding protein of ~40 kDa appeared.

Immunoprecipitation with an antibody specific to the epitope tag revealed that the 40 kDa protein was TTP itself. Expression of the tagged protein in these cytosolic extracts was confirmed by Western blotting; the protein that reacted with the epitope tag antibody also reacted with TTP antibodies. Essentially identical results were obtained when the probe was a 70 bp fragment consisting only of the TNFα ARE (25).

These data show for the first time that TTP binds directly to the ARE contained within the 3'-UTR of TNFα mRNA and probably other labile mRNAs, and that this binding somehow destabilizes these mRNAs. Many aspects of this interaction remain to be elucidated, including: The exact interaction sites on the mRNA and protein; the identities of the other proteins that are presumably recruited to this site to facilitate mRNA cleavage; qualitative or quantitative differences in TTP binding to other mRNAs with ARE-containing destabilizing elements; the effect of TTP serine phosphorylation (18) on mRNA binding; the potential overlapping effects of other members of the CCCH protein family; a possible role for TTP in regulating TNFα production from other cell types in which both proteins are expressed, such as keratinocytes and lymphocytes; the role of TTP in cells that do not synthesize appreciable TNFα; its possible dysregulation by genetic or environmental factors or infectious processes in diseases of chronic TNFα excess; and many others. However, this demonstration of direct binding of TTP to TNFα mRNA, an interaction that presumably occurs in the cytosol, should permit the development of screening assays for compounds that potentiate, mimic or increase the specificity of this reaction, and may ultimately lead to novel drugs capable of inhibiting TNFα biosynthesis.

REFERENCES FOR EXAMPLE 2

1. B. Beutler, *J. Invest. Med.* 43, 227 (1995).
2. C. O. Jacob, *J. Autoimmunity* 5 (Suppl. A), 133 (1992); M. R. Shalaby, B. Fendly, K. C. Sheehan, R. D. Schreiber, A. J. Ammann, *Transplantation* 47, 1057 (1989); J. Cheng, K. Turksen, Q-C. Yu, H. Schreiber, M. Teng, *Genes & Development* 6, 1444 (1992); J. Keffer et al., *EMBO J.* 10, 4025 (1991); J. M. Reimund et al., *J. Clin Immunol.* 16, 144 (1996); M. Odeh, *J. Intern Med.* 228, 549 (1990).
3. H. M. Lorenz et al., *J. Immunol.* 156, 1646 (1996); E. Abraham et al., *JAMA* 277, 1531 (1997).
4. K. Hattori et al., *Blood* 90, 542 (1997); J. M. Clements et al., *J. Neuroimmunol.* 74, 85 (1997); Y Morimoto, K. Nishikawa, M. Ohashi, *Life Sci.* 61, 795 (1997); C. C. Solorzano et al., *Shock* 7, 427 (1997).
5. B. C. Varnum, R. W. Lim, V. P. Sukhatme, H. R. Herschman, *Oncogene* 4, 119 (1989); B. C. Varnum, Q. M. T. Chi, B. Fletcher, H. R. Herschman, *Mol. Cell. Biol.* 11, 1754 (1991); M. J. Thompson, W. S. Lai, G. A. Taylor, P. J. Blackshear, *Gene* 174, 225 (1996).
6. G. A. Taylor et al., *Nucleic Acids Res.* 19, 3454 (1991)
7. R. N. DuBois, M. W. McLane, K. Ryder, L. F. Lau, D. A. Nathans, *J. Biol. Chem.* 265, 19185 (1990).
8. W. S. Lai, D. J. Stumpo, P. J. Blackshear, *J. Biol. Chem.* 265, 16556 (1990).

9. G. A. Taylor et al., *Immunity* 4, 445 (1996).
10. E. Carballo, G. S. Gilkeson, P. J. Blackshear, *J. Clin. Invest.* 100, 986 (1997).
11. W. S. Lai and P. J. Blackshear, unpublished data.
12. B. Beutler and T. Brown, *J. Clin. Invest.* 87, 1336–1344 (1991); J. Han, G. Huez, B. Beutler, *J. Immunol.* 146, 1843 (1991).
13. Y. Shi et al., *J. Biol. Chem.* 272, 29290 (1997).
14. K. Godfrey, *N. Engl. J. Med.* 313, 1450 (1985).
15. A. J'rres et al., *Cytokine* 9, 119 (1997).
16. J. Han, B. Beutler, G. Huez, *Biochim. Biophys. Acta* 1090, 22 (1991).
17. G. A. Taylor, M. J. Thompson, W. S. Lai, P. J. Blackshear, *Mol. Endocrinol.* 10, 140 (1996).
18. G. A. Taylor, M. J. Thompson, W. S. Lai, P. J. Blackshear, *J. Biol. Chem.* 270, 13341 (1995).
19. G. Hensel, D. N. Mannel, K. Pfizemnaier, M. Kr'nke, *Lymphokine Res.* 6, 119 (1987); D. R. Spriggs et al., *Cancer Res.* 50, 7101 (1990).
20. G. Shaw and R. Kamen, *Cell* 46, 659 (1986); R. D. Klausner, T. A. Rouault, J. B. Harford, *Cell* 72, 19 (1993); A. B. Sachs, *Cell* 74, 413 (1993).
21. Plamid H6E was first made by inserting a 3.7 kb ExoRI-XbaI fragment from the human genomic TTP clone (29) into the plasmid vector pBS+ (Stratagene). This insert contained ~1 kb or promoter, the first exon, the intron, the second intron, and 30 bp of 3'-flanking region. For H6E.HGH3', a 597 bp NsiI-XbaI fragment in the 3'-UTR of the human TTP gene that contained five rapid degradation signal sequences was replaced by the entire 110 bp human growth hormone (HGH) 3'-UTR. The PCR primers used to amplify this fragment were (5'), 5'-GTG-GCTTCTAGatgcatGGGTGGCATC-3' (SEQ ID NO:36, and (3'), 5-GAAGGACACCtctagaGACAAAATGATGC-3' (SEQ ID NO:37), where the capital letters represent the HGH sequences and the small letters represent the recognition sites for NsiI (5' primer) and XbaI (3' primer).

For CMV.TTP.tag, the influenza hemagglutinin (HA) epitope tag (31) was attached to the last amino acid of the human TTP cDNA (6) by the PCR-overlapping mutagenesis technique (30). The fusion insert containing the entire human TTP protein coding region and the HA epitope was then cloned into the HindIII site of the vector CMV.BGH3'/BS+. This vector was created by blunt-ligating a NruI-PvuII fragment from pRc/CMV2 (Invitrogen, San Diego, Calif.), which contains the hCMV promoter/enhancer and the bovine growth hormone polyadenylation signal, into the EcoRI and HindIII sites of pBS+ (Stratagene).

22. A.-B. Shyu, M. E. Greenberg, J. G. Belasco, *Genes & Development* 3, 60 (1989); N. Xu, C.-Y. A. Chen, A.-B. Shyu, *Mol. Cell. Biol.* 17, 4611 (1997).
23. D. F. Lobach, J. M. Rochelle, M. L. Watson, M. F. Seldin, P. J. Blackshear, *Genomics* 17, 194 (1993).
24. M. Z. Gilman, R. N. Wilson, R. A. Weinberg, *Mol. Cell. Biol.* 6, 4305 (1986); D. J. Stumpo, T. N. Stewart, M. Z. Gilman, P. J. Blackshear, *J. Biol. Chem.* 263, 1611 (1988).
25. RNA probes were prepared as follows: Plasmid p3'mTNFα, containing the mouse TNFα3'-UTR (bases 1110–1627 of GenBank accession number X02611) was created by RT-PCR, with the use of total cellular RNA from Raw 264.7 cells treated for 4 hrs with 1 µg of LPS, as templates for RT. The 5' primer was 5'-CTTTCCgaattcACTGGAGCCTC-3' (SEQ ID NO:32), and the 3' primer was 5'-TAGAtctagaAGCGATCTT-TATTTCTCTC-3' (SEQ ID NO:33), with the small letters indicating the restriction sites for EcoRI and XbaI, respectively. The resulting PCR fragment was digested and cloned into the EcoRI and XbaI sites of the vector pSK-(Stratagene). Plasmid pTNFα 1197–1350 contained a 153 bp fragment that included the ARE of the mouse TNFα 3'-UTR (1197–1350 of X02611); this was made using plasmid p3'mTNFα as the template. The 5' primer was 5'-GATAagatctCAGGCCTTCC-3' (SEQ ID NO:34), and the 3'primer was 5'-GCCTtctagaTAAATACATTCAT-AAGC-3' (SEQ ID NO:35). The resulting PCR product was digested with BglII and XbaI (sites indicated by small letters in the primers) and cloned into the BamHI and XbaI sites of the vector pSK-. Plasmid pTNFα 1281–1350 contained the seven AUUUA motifs of the TNFα ARE (1281–1350 of X02611). This was constructed using similar methods. Correct sequences of these plasmids were confirmed by dideoxy sequencing (Amersham Life Sciences Inc., Arlington Heights, Ill.). To radiolabel the RNA transcripts with α-$^{32}$P-UTP (800 Ci/mmol), plasmid TNFα1197–1350 was linearized with XbaI and used as the template in the Promega Riboprobe in vitro Transcription System protocol (Promega, Madison, Wis.). The resulting product was precipitated with ammonium acetate and ethanol.

26. J. Y. Tso, X. H. Sun, T. H. Kao, K. S. Reece, R. Wu, *Nucleic Acids Res.* 13, 2485 (1985).
27. Confluent dishes were washed three times with cysteine-free medium supplemented with 10% FCS. Cells were stimulated for 4 hrs in the same medium with control conditions (Con), 1 µg/ml LPS or 10 ng/ml TNFα. For the last three hours of the incubation, 200 µCi/ml of 35S-cysteine (NEN Life Sciences, Boston, Mass.) were added to the cultures. Cells were washed twice with ice-cold PBS, scraped into 10 ml of PBS and pelleted by centrifugation (1000 g for 5 min at 4°). Cells were then resuspended in 600 µl of lysis buffer (50 mM Tris-HCl, pH 7.5; 50 mM NaCl; 3 mM MgCl2; 5% (v/v) glycerol; 0.5% (v/v) NONIDET® P-40 (octylphenolpoly(ethyleneglycolether)) (NP-40); 0.02% (w/v) sodium azide; 5 mM EDTA; 0.1 mM phenylmethylsulfonyl fluoride (PMSF); 20 µg/ml soybean trypsin inhibitor; and 8 µg/ml leupeptin), incubated on ice for 20 min, and lysed by passing 5 times through a 28 gauge needle attached to a 1 ml syringe with no dead space (Becton Dickinson and Company, Franklin Lakes, N.J.). Nuclei (pellet after centrifugation at 1000 g for 5 min at 4° C.) were washed once in ice-cold wash buffer (10 mM Tris-HCl, pH 7.5; 15 mM KCl; 1.5 mM MgCl$_2$; 0.5 mM PMSF; and 5% glycerol), centrifuged at 1000 g for 5 min at 4° C., and then resuspended and sonicated in the same volume of lysis buffer used initially to lyse the cells. The cytosolic fraction (supernatant) was clarified by centrifugation at 45,000 g for 30 min at 4° C., using a table-top ultracentrifuge (Beckman TL-100, rotor TLA.45, Beckman Instruments, Inc., Fullerton, Calif.). This method has been shown to result in clean cytosol-nuclear preparations, when assessed by Western-blotting with an anti-SP1 antibody. Cytosolic extracts matched by trichloroacetic acid-precipitable radioactivity and equivalent volumes of nuclear extracts were pre-cleared with pre-immune rabbit serum (1:100 dilution, 1 hr at 4° C.) and protein A-sepharose (1 hr at 4° C.), and then incubated overnight at 4° C. in the presence of either pre-immune serum (1:100) or a 1:100 dilution of a polyclonal rabbit anti-mouse immune serum (17, 18). Immune complexes were recovered by centrifugation after the addition of protein A-sepharose, washed three times with wash buffer (50 mM Tris-HCl, pH 8.3; 150 mM NaCl; 1 mM EDTA; 0.5% NP-40), resuspended in 100 µl of SDS-sample buffer (28), and subjected to 9% SDS-polyacrylamide gel electrophoresis. Prior to autoradiography, gels were fixed and treated with Autofluor (National Diagnostics, Atlanta, Ga.).

28. P. J. Blackshear, *Methods Enzymol.* 104, 237 (1984).
29. W. S. Lai, M. J. Thompson, G. A. Taylor, Y. Liu, P. J Blackshear, *J. Biol. Chem.* 270, 25266 (1995).
30. W. S. Lai, M. J. Thompson, P. J Blackshear, *J. Biol. Chem.* 273, 506 (1998).
31. P. A. Kolodziej, R. A. Young, *Methods Enzymol.* 194, 508 (1991).

EXAMPLE 3

Evidence that TTP Binds to AU-Rich Elements and Promotes the Deadenylation and Destabilization of TNFα mRNA In the present study, we asked whether the integrity of TTP's zinc fingers was necessary for its mRNA destabilizing and/or direct binding effect, and explored the nature of the cleavage of TNFα mRNA that resulted from TTP binding to its ARE in intact cells. Our data indicate that TTP exhibits zinc-finger-dependent ARE-binding activity, as well as a zinc finger-dependent ability to promote TNFα mRNA deadenylation and degradation. Through regulation of its cellular, subcellular and tissue-specific expression, induction kinetics and post-translational modification, this protein offers a myriad of potential mechanisms for regulating the stability of ARE-containing mRNAs.

Materials and Methods

1. Plasmid Construction.
   a. Parent Plasmids.

The human TTP cDNA (43) and a human TTP genomic clone were obtained as described (23). Plasmid H6E was made by inserting a 3.7 kb EcoRI-XbaI fragment from the human genomic clone into the plasmid vector pBS+ (Stratagene, La Jolla, Calif.). This insert contained ~1 kb of promoter, the first exon, the single intron, the second exon, and 30 bp of 3' flanking region.

b. Expression Constructs.

H6E.HGH3' was constructed as follows: a 597 bp NsiI-XbaI fragment in the 3' untranslated region (3' UTR) of H6E that contained five rapid degradation signal sequences was replaced by 110 bp of human growth hormone (HGH) sequence that encode the entire HGH 3' UTR (GenBank accession number M13438). The template used to amplify this fragment was pØGH (Nichols Institute Diagnostics, San Juan, Calif.). The PCR primers were, (5'), 5'GTGGCTTCTAGAtgcatGGGTGGCATC3' (SEQ ID NO:30), and (3'), 5'GAAGGACACCtctagaGACAAAATGATGC3' (SEQ ID NO:31), where the capital letters correspond to the HGH sequences and the small letters correspond to the recognition sites for NsiI (5' primer) and XbaI (3' primer).

Construct CMV.hTTP.tag was made as follows: The epitope tag derived from the influenza hemagglutinin (HA) protein (21) was attached to the last amino acid of human TTP (hTTP) cDNA by the polymerase chain reaction primer-overlapping mutagenesis technique (24). The fusion insert that contained the entire human TTP protein coding region and the HA epitope (hTTP.tag) was then cloned into the HindIII site of the vector CMV.BGH3'/pBS+. The vector CMV.BGH3'/pBS+ was created by blunt-ligating a NruI-PvuII fragment from pRc/CMV2 (Invitrogen, Carlsbad, Calif.), which contains the hCMV promoter/enhancer and bovine growth hormone polyadenylation signal, into the EcoRI and HindIII sites of pBS+ (Stratagene). Expression of the fusion protein was confirmed by Western analysis of cytosolic extracts from human embryonic kidney (HEK) 293 cells transfected with the construct CMV.hTTP.tag, using the polyclonal antibody HA.11 (BAbCO, Richmond, Calif.) that recognized the tag. The zinc finger mutants C124R and C147R of CMV.hTTP.tag, which contained a single amino acid mutation at position 124 or 147, were made by the polymerase chain reaction primer-overlapping mutagenesis technique. In these mutants, the third cysteine in the CCCH motif of the first (C124) or the first cysteine (C147) in the second zinc finger were changed to arginine. Mutant S228A of CMV.hTTP.tag, in which the serine at position 228 (equivalent to the MAP kinase phosphorylation site S220 in mouse TTP (44)), was mutated to alanine using the same technique. All mutations were confirmed by dideoxy sequencing (Amersham/USB).

CMV.hTTP.EGFP was made as follows: Using the polymerase chain reaction primer-overlapping mutagenesis technique, an AgeI site was created immediately after the last amino acid of hTTP, so that the stop codon of hTTP was eliminated. When the Asp718-AgeI fragment containing the entire hTTP coding region was inserted into the corresponding restriction sites of plasmid EGFP-N1 (Clontech, Palo Alto, Calif.), hTTP was fused to the N-terminus of EGFP in the same reading frame. The zinc finger mutants of CMV.hTTP.EGFP(C124R or C147R) were made by inserting BstEII-BamHI fragments of hTTP containing the mutations from the C124R or C147R mutants of CMV.hTTP.tag into the corresponding restriction sites in CMV.hTTP.EGFP. To make the construct H6E.EGFP, a promoterless fusion construct was created by first removing the CMV promoter from plasmid CMV.hTTP.EGFP by digestion with AseI and BglII, and then blunt-religating the remaining DNA. The hTTP-EGFP fusion plasmid without the promoter was then digested with EcoRI (a site in the multiple cloning site of the vector) and BstEII (a site in the hTTP coding region), and then an EcoRI-BstEII fragment from plasmid H6E containing ~1 kb of promoter, the first exon, the intron, and part of the second exon up to the BstEII site, was inserted into the corresponding sites in the fusion construct.

CMV.mTNFa was made by first inserting a NarI-XbaI fragment containing bp 117–1325 of a mouse TNFα cDNA sequence (GenBank accession number X02611) into the HindIII (blunt-ligation) and XbaI sites of vector pSK-(Stratagene); an AseI-XhoI fragment containing the hCMV promoter/enhancer from pEGFP-N1 (Clontech) was then blunt-ligated into the XhoI site of the vector. Correct orientation of the promoter with respect to the mTNFα insert was confirmed by dideoxy sequencing. The mTNFα cDNA clone, provided by Dr. B. Beutler (The University of Texas Southwestern Medical Center, Dallas, Tex.), contained an incomplete 3' UTR that ended at bp 1325 (GenBank accession number X02611), with 33 adenylate residues attached to the last T.

CMV.mTNFa (dARE) was made by deleting the ARE region (bp 1302–1325 of GenBank accession number X02611) of CMV.mTNFα using the polymerase chain reaction primer-overlapping mutagenesis technique. There were 28 adenylate residues attached to the last nucleotide (bp 1301 of GenBank accession number X02611) of this construct.

2. Transfection of HEK 293 Cells, Northern Analysis, RNase H Assay, and Cytosolic Extract Preparation.

HEK 293 cells were maintained in minimal essential medium (Life Technologies, Inc., Gaithersburg, Md.)

supplemented with 10% fetal bovine serum, 100 units/ml penicillin, and 100 μg/ml streptomycin. Transient transfection of 2×10⁶ cells with CMV.mTNFα or other constructs in calcium-phosphate precipitates was performed as described previously (23, 24), except that the transfection mixture was allowed to stay on the cells for 16 to 20 hrs, and the glycerol shock step was omitted. In some experiments, pXGH5 (Nichols Institute Diagnostics) was also co-transfected to monitor transfection efficiency. Assays of released HGH were performed as described previously (23, 24).

Twenty-four hrs after the removal of the transfection mixture, total cellular RNA was harvested from the HEK 293 cells using the RNeasy system (Qiagen, Valencia, Calif.). Northern blots were prepared as described (22). Blots were hybridized to a random-primed, $\alpha$-$^{32}$P-labeled mouse TTP cDNA (22) or a ~1 kb NarI-BglII fragment of mTNFα cDNA. Some blots were also hybridized to an $\alpha$-$^{32}$P-labeled GAPDH cDNA probe (7) or a ~0.3 kb fragment of mouse cyclophilin cDNA (bp 166–480, GenBank accession number X52803).

RNase H assays were performed by annealing RNA and oligonucleotide in 10 μl of 50 mM KCl for 5 min at 50° C. followed by an additional 10 min at 22° C. The mixture was incubated further at 37° C. for 30 min in a buffer (4 mM HEPES-KOH (pH 8), 50 mM KCl, 2 mM $MgCl_2$, 0.2 mM dithiothreitol (DTT) and 1 μg/μl bovine serum albumin (BSA)) containing 0.8 unit of RNase H (Promega, Madison, Wis.), in a final volume of 25 μl. The reaction mixture was then precipitated with sodium acetate and ethanol and the resulting RNA was subjected to Northern analysis.

Cytosolic extracts were prepared from HEK 293 cells 24 hr after the removal of the transfection mixture. The cells were incubated on ice for 20 min in a buffer consisting of 10 mM HEPES (pH 7.6), 3 mM $MgCl_2$, 40 mM KCl, 5% (v/v) glycerol, 0.5% (v/v) Nonidet-P40, 2 mM DTT, 0.5 mM phenylmethylsulfonyl fluoride (PMSF) and 8 μg/ml leupeptin (lysis buffer). Lysis of the cells and maintenance of intact nuclei were carefully monitored by microscopy. The nuclei and cell membrane debris were removed by centrifugation at 16,000 g at 4° C. for 15 min. Glycerol was added to the supernatant (cytosolic extract) to 20% (v/v), and the resulting extract was stored at −70° C.

3. Analysis of RNA-Protein Complexes by Sodium Dodecyl Sulfate-Polyacrylamide Gel Electrophoresis (SDS-PAGE), Electrophoretic Mobility Shift Assay, and Immunoprecipitation.

a. Preparation of RNA Probes

Plasmid p3'mTNFα containing the mouse TNFα3'UTR (bp 1110–1627 of GenBank accession number X02611) was constructed by RT-PCR, using RNA from Raw 264.7 cells treated for 4 hrs with 1 μg/ml of LPS (Sigma, St. Louis, Mo.) as a template for RT. The 5' primer for PCR amplification was 5'CTTTCCgaattcACTGGAGCCTC3' (SEQ ID NO:32), and the 3' primer was 5'TAGAtctagaAGCGATCTTTATTTCTCTC3' (SEQ ID NO:33), where the small letters indicate the restriction sites for EcoRI and XbaI, respectively. The resulting PCR product was digested with these enzymes and cloned into the EcoRI and XbaI sites of the vector pSK-(Stratagene).

Plasmid pTNFα 1197–1350, which contained a 153 bp fragment containing the AU-rich element (ARE) of mouse TNFα3'UTR (bp 1197–1350 of GenBank accession number X02611), was made by PCR using plasmid p3'mTNFα as a template, with a 5' primer, 5'GATAagatctCAGGCCTTCC3' (SEQ ID NO:34), and a 3' primer, 5'GCCTtctagaTAAATACATTCATAAGC3' (SEQ ID NO:35. The resulting PCR product was digested with BglII and XbaI (sites indicated by small letters in the primers) and cloned into the BamHI and XbaI sites of the vector pSK-.

Plasmid pTNFα 1197–1300 (bp 1197–1300 of GenBank accession number X02611), containing only one AUUUA motif, was made using the TNFα3'UTR as template, with the M13–20 primer as the 5' primer, and a 3' primer, 5'CTGAtctagaAGTGCAAATATAAATAGAGG3' (SEQ ID NO:38). The resulting PCR product was digested with EcoRV and XbaI (site indicated by small letters in the 3' primer) and cloned into the corresponding sites of the vector pSK-.

Plasmid pTNFα 1281–1350 (bp 1281–1350 of GenBank accession number X02611) contained seven AUUUA motifs, five of them being overlapping UUAUUUAUU nanomers. This was constructed using the TNFα 3'UTR as template, with a 5' primer, 5'GACTggatccTCTATTTATATTTGCAC3' (SEQ ID NO:39, and the M13 reverse primer as the 3' primer. The resulting PCR product was digested with BamHI (site indicated by small letters in the 5' primer) and XbaI and cloned into the corresponding sites of the vector pSK-.

Plasmid pTNFα 1309–1332 (bp 1309–1332 of GenBank accession number X02611), containing four overlapping UUAUUUAUU nanomers, was constructed by inserting double-stranded oligonucleotides spanning bp 1309–1332 into the EcoRV-XbaI cloning sites of pSK-. Plasmid pTNFα 1309–1332 (A/G), containing the same sequence except that the five As in the AUUUA motifs were replaced with Gs (see FIG. 1B), was made with the same technique.

Plasmid pTNFα 1110–1325 (bp 1110–1325 of GenBank accession number X02611) was made by inserting the EcoRI-XbaI fragment of the mTNFα clone from Dr. Beutler into the corresponding sites of pSK-. This 248 base fragment contained five AUUUA motifs, three of them being clustered nanomers. There were 33 adenylate residues at its 3' end.

Correct sequences of all plasmid inserts were confirmed by dideoxy sequencing.

To label RNA transcripts with $\alpha$-$^{32}$P-UTP (800 Ci/mmol), the above plasmids linearized with XbaI were used as templates, and the Promega Riboprobe in vitro Transcription Systems protocol was employed. The resulting product was precipitated with ammonium acetate and ethanol.

b. Cross-Linking of Proteins to RNA

Cytosolic extracts prepared from HEK 293 cells transfected with CMV.hTTP.tag or vector (20 μg of protein) were incubated with 2×10⁶ cpm of RNA probe in a 96-well plate at room temperature for 20 min in 20 μl lysis buffer (without protease inhibitors). Heparin and yeast tRNA were added to final concentrations of 0.5 μg/μl and 50 ng/μl, respectively, for an additional 10 min. The 96-well plate was then placed on ice and irradiated at 254 nm UV light in a Stratalinker (Stratagene) for 30 min at a distance of 5 cm from the light source. RNA not associated with protein was digested with 100 units of RNase T1 (Life Technologies, Inc) for 20 min at room temperature, and further digested with 1 μg/μl of RNase A (Pharmacia Biotech, Piscataway, N.J.) at 37° C. for 15 min. The RNase resistant RNA/protein complexes were analyzed by SDS-PAGE (10% acryl amide gel) followed by autoradiography.

Identical samples were diluted to 0.5 ml in RIPA buffer and precleared with non-immune rabbit serum (1:100 dilution, 1 hr at 4° C.) and protein A-sepharose (Pharmacia Biotech) (1 hr at 4° C.), and then incubated overnight at 4° C. in the presence of either non-immune serum (1:100) or a 1:100 dilution of a polyclonal antiserum. Immune complexes were recovered by centrifugation after the addition of protein A-sepharose, washed three times with wash buffer (50 mM Tris-HCl, pH 8.3; 150 mM NaCl; 1 mM EDTA; 0.5% (v/v) NP-40), resuspended in 100 µl of SDS-sample buffer, and subjected to SDS-PAGE on 10% acrylamide gels and autoradiography.

c. Western Blotting.

Cell extracts (5–50 µg protein) were mixed with ⅕ volume of 5×SDS sample buffer (2), boiled for 5 min, then loaded onto 10% SDS-PAGE gels. Western blotting was performed by standard techniques. Membranes were incubated in Tris-buffered saline/0.5% TWEEN® 20 (polyoxyethylene sorbitan monolaureate) (TBS/T) with either polyclonal antiserum HA.11 (1:2,500), or a rabbit antiserum to mouse TTP, 2640 (1:100; (38)), or a rabbit antiserum to human TTP, DU88 (1:100; (32)). Incubation of the membranes with second antibody and development were performed as described (6).

d. RNA Electrophoretic Mobility Shift Assay.

Cytosolic extracts prepared from HEK 293 cells transfected with either vector alone, or H6E.HGH3', or expression constructs driven by the CMV promoter (10 µg of protein), were incubated with $1 \times 10^5$ cpm of RNA probe at room temperature for 20 min in 20 µl lysis buffer (without protease inhibitors). Heparin and yeast tRNA were added to final concentrations of 0.5 µg/µl and 50 ng/µl, respectively, for an additional 10 min. RNA not associated with protein was digested with 100 units of RNase T1 (Life Technologies, Inc.) for 20 min at room temperature; the reaction mixture was then loaded onto a 6% non-denaturing acrylamide gel and subjected to electrophoresis at 250 V for 90 min, in 0.4× Tris/borate/EDTA buffer.

4. Green Fluorescent Protein Assays.

Cells were plated onto 100 mm dishes and transfected with hTTP-EGFP fusion constructs as described above. Twenty four hrs after the removal of the transfection mixture, the cells were transferred into 4-well Titertek slides (Fisher Scientific, Pittsburgh, Pa.) and incubated at 37° C. overnight. The cells were washed once in PBS, fixed with 3.7% (v/v) formaldehyde for 5 min, and washed again with PBS. Glass cover slips were mounted using Vectashield fluorescent mounting media (Vector Laboratories, Burlingame, Calif.) and sealed with nail polish. Fluorescence microscopy was performed with a Zeiss confocal microscope model LSM 410 UV (Carl Zeiss, Inc., Thornwood, N.Y.). Images were collected under 488 nm excitation using a 515–565 nm emission filter and a 100×1.4 NA oil immersion lens. Photographs were taken with a 16.1 sec scan.

Results

Effect of TTP on TNFα mRNA Species.

In most of the expression studies in 293 cells described below, we used a TNFα expression construct, CMV.mTNFα, that did not contain the entire native 3'UTR; instead, the TNFα sequence ended in the middle of the fourth AUUUA motif within the ARE (bp 1325 of GenBank accession number X02611; FIG. 1B) and was immediately followed by 33 adenylate residues encoded by the vector. To test whether this shortened ARE exhibited TTP binding activity, we compared TTP binding to a 3'-truncated RNA probe, comprising bases 1110–1325 of GenBank accession number X02611, to its binding to a non-truncated probe, comprising bases 1281–1350. This non-truncated probe contained the seven natural AUUUA motifs, five of them in clustered nanomers (FIG. 1B). We recently demonstrated that TTP could bind directly to a 1197–1350 probe (7). UV cross-linking of these probes to proteins in extracts from CMV.hTTP.tag-transfected cells indicated that TTP bound to the truncated probe 1110–1325 almost as well as to the probe containing all of the native AUUUA motifs (probe 1281–1350) (FIG. 1). A probe spanning bases 1197–1300, which only contained one AUUUA, exhibited barely detectable TTP binding activity under these conditions (FIG. 1).

We therefore used CMV.mTNFα in the cell expression studies described below, given the ability of TTP to bind to its mRNA ARE. The HEK 293 cells used in these studies normally do not express either TTP or TNFα, making these widely used cells a suitable intact cell system in which to study the interaction of TNFα mRNAs with transfected-expressed TTP. In addition, the expression of the truncated form of TNFα mRNA in these cells made possible for the first time the detection of a processing (probably deadenylated; see below) intermediate; this intermediate was not detectable when the native, full-length TNFα mRNA was expressed.

Both TTP and TNFα mRNAs were readily detected when the cells were transfected with either TTP or TNFα expression plasmids. There was a complex relationship found between the concentration of transfected CMV.hTTP.tag DNA and the resulting TNFα mRNA accumulation in the absence of actinomycin D treatment. At low concentrations of transfected DNA (5 and 10 ng per plate), TNFα mRNA accumulation was ~20% of control, as determined by scanning densitometry of the Northern blot. This decrease in mRNA amount was accompanied by the appearance of a smaller species of mRNA, which first became apparent at 5–10 ng of DNA, but was more obvious at 50 ng. As described below, we believe this lower band to be the deadenylated form of the TNFα mRNA. Beginning at 50 ng DNA through all higher concentrations used essentially all TNFα mRNA was in this smaller form. However, the total amount of TNFα mRNA accumulation increased substantially at higher concentrations of DNA (see below) to reach a maximum of 214% of control at 500 ng. It remained high at 1 µg before decreasing to 51% of control at 5 µg. A similar but "right-shifted" dose-response relationship was present with the genomic TTP construct H6E.HGH3', which uses the weaker native TTP promoter rather than the CMV promoter; in this case, 2 µg of DNA decreased total TNFα mRNA accumulation to 16% of control (n=3); higher concentrations (5 and 10 µg) resulted in continued expression of the smaller species in greater amounts.

The predominance of the smaller band and the almost complete absence of the larger band could be seen more readily after actinomycin D exposure, presumably because the larger band represented recently synthesized TNFα mRNA that was more likely to be full-length. In this case, 5 and 10 ng of CMV.hTTP.tag DNA resulted in less than 10% of control TNFα mRNA expression.

Because of the peculiar nature of this dose response, we performed four identical experiments with low concentrations of CMV.hTTP.tag, in which all samples were corrected for transfection efficiency using HGH expression, and were corrected for loading using Northern analysis of GAPDH mRNA and Phosphorimager analysis. Compared to the vector alone control, there was a decrease in total hybridizing TNFα mRNA by 83% (to 17% of control) at 0.01 µg CMV.hTTP.tag. This mean value increased to 173% of control at 0.05 µg, and to 300% of control at 0.1 µg DNA. Most of the hybridizing TNFα mRNA seen at the higher concentration of transfected CMV.hTTP.tag was in the smaller form.

To determine whether transcription of CMV.TNFα was affected by the TTP expression plasmids, various amounts of either H6E.HGH3' or CMV.hTTP.tag were co-transfected into 293 cells with CMV.mTNFα or CMV.mTNFα (dARE). In the latter construct, which was otherwise identical to CMV.mTNFα, 24 bp of the ARE were deleted (bp 1302–1325 of mTNFα cDNA; see FIG. 1B), resulting in a disrupted ARE that was incapable of binding TTP (see below). In this case, despite equivalent co-expression of TTP, the TNFα mRNA expressed from the CMV.mTNFα construct containing the normal ARE was shortened in the normal way by the co-expressed TTP, while expression of the mutated CMV.mTNFα construct was unaffected either in apparent size or total accumulation by any concentration of co-transfected H6E.HGH3', and was minimally affected by CMV.hTTP.tag. Quantitation of these result by PhosphorImager analysis and normalization for loading by cyclophilin mRNA showed that H6E.HGH3' at 5 and 10 μg resulted in TNFα (dARE) expression that was 105% and 98%, respectively, of the vector alone co-transfected control; whereas CMV.hTTP.tag at 0.01, 0.1 and 1 μg resulted in TNFα (DARE) expression that was 110%, 97% and 73% of control, respectively. These experiments indicate that the effect of TTP to decrease TNFα mRNA accumulation at low concentrations of CMV.hTTP.tag (i.e., 5 and 10 ng) was unlikely to be due to non-specific "squelching" of transcription (7, 34), although this may have contributed to the modest decrease in TNFα mRNA expression seen with larger (5 μg) amounts of CMV.hTTP.tag.

Evidence that TTP Promoted Deadenylation of TNFα mRNA.

The effect of TTP expression to cause shortening of the TNFα mRNA suggested that TTP was promoting deadenylation of the TNFα mRNA poly A tail. To evaluate this possibility, oligo $dT_{12-18}$ (P1) was added to total cellular RNA, and RNase H was used to remove the poly A tail (31). When this technique was used on RNA samples from cells co-transfected with CMV.mTNFα and either vector alone or TTP expression constructs (H6E.HGH3' in A, CMV.hTTP.tag in B and C), only the smaller of the two TNFα mRNA species remained. The smaller of the two mRNA species seen in the cells transfected with TTP constructs did not further decrease in size with the RNase treatment; this fact, and its identical size to the deadenylated TNFα mRNA from the control cells, indicated that the smaller form of the TNFα mRNA was deadenylated mRNA.

We also performed an RNase H experiment that used an oligonucleotide complementary to bp 506–528 of TNFα mRNA (GenBank accession number X02611; P2). The predicted sizes of the mRNA fragments from the resulting mRNA cleavage were ~400 b (5' portion) and ~810 b (3' portion). When RNA from 293 cells expressing both TNFα and TTP was analyzed after cleavage, most of the 3' TNFα mRNA fragment was in the form of the deadenylated smaller species, as compared to RNA harvested from cells expressing TNFα and vector alone. When both oligonucleotides were added together, the 3' fragment of the TNFα mRNA was of identical size in samples from control and TTP expressing cells. The size of the ~400 b 5' fragment was unaffected by TTP expression. These data confirmed that TTP promoted deadenylation of the TNFα mRNA.

Evidence for a Precursor-Product Relationship Between the Upper and Lower Forms of TNFα mRNA.

In order to demonstrate that the larger, presumably polyadenylated form of TNFα mRNA could be converted to the smaller, deadenylated form by the presence of TTP, we analyzed the patterns of TNFα mRNA expression in cells co-transfected with small amounts of TTP expression constructs, before and after 4 hrs of exposure to actinomycin D (10 μg/ml). As shown in the cells transfected with vector alone (BS+, 10 μg; BS+, 5 μg), there was no conversion of the larger form of TNFα mRNA to a stable, smaller form in the absence of TTP, although the total amount of full-length mRNA decreased modestly after 4 hrs of actinomycin D. However, in the presence of TTP (10 μg of H6E.HGH3' or 0.05–0.5 μg of CMV.hTTP.tag), actinomycin D exposure clearly led to the disappearance of the larger band, so that only the smaller band remained. Two additional experiments also examined intermediate time points. In both cases, the expression of TTP resulted in both forms of TNFα mRNA; the upper form then gradually disappeared after actinomycin D treatment.

Evidence that the ARE Binding Protein in 293 and Macrophage Extracts is TTP.

We next examined TNFα ARE binding activity in cytosolic extracts from bone marrow-derived macrophages from wild-type and TTP (−/−) mice that had been stimulated with LPS. After the cell extracts were UV cross-linked to the TNFα ARE probe and treated with RNases, an RNase-resistant RNA-protein complex was immunoprecipitated by an anti-TTP antibody but not by pre-immune serum. The macrophage TTP that was immunoprecipitated from the LPS-treated TTP (+/+) cells, but not from untreated (+/+) cells or from the treated or untreated TTP (−/−) cells, appeared as a smear with an average size of 50 kDa, as compared to the apparent 40–44 kDa of mTTP expressed from CMV.mTTP in 293 cells. In our earlier studies, TTP migrated as a smear or multiple bands of ~35 to ~55 kDa (7, 44, 45). The difference in apparent molecular weights seen in the present experiment may have been due to differences in post-translational modification of the TTP protein, since, for example, its apparent molecular weight is known to increase after mitogen-stimulated phosphorylation (44). Despite these differences in apparent M, the identity of the immunoprecipitated protein as TTP cross-linked to $^{32}P$-labeled TNFα ARE was confirmed by the facts that the complex was precipitated from 293 cells that were transfected with TTP-expressing plasmids but not from cells transfected with vector alone; it was precipitated from 293 cells by three different antibodies including an antibody to the epitope tag (7); and that it was specifically immunoprecipitated from LPS-stimulated wild-type macrophages but not from unstimulated wild-type cells or from stimulated or unstimulated TTP-deficient cells.

These results indicate that the endogenous TTP formed after LPS treatment of normal macrophages can also bind to the TNFα ARE, and support the previously documented connection between the expression of TTP and the more rapid decay of TNFα mRNA in macrophages (7).

Involvement of the TTP Zinc Fingers in the Binding of TTP to the ARE of TNFα mRNA.

We next evaluated the possible involvement of each of the two CCCH zinc fingers in the ARE-binding activity of TTP, using the TNFα probe 1197–1350 (see FIG. 1B). When cell extracts prepared from 293 cells that had been transfected with vector alone were used in UV cross-linking experiments, a major radioactive band of $M_r$ ~80,000 and several minor species were noted. When cell extracts prepared from 293 cells that had been transfected with hTTP expression constructs were used in UV cross-linking experiments, the extracts from cells transfected with either the wild-type CMV.hTTP.tag or the S228A mutant (a point mutation at a MAP kinase phosphorylation site in the protein; 44) formed readily detectable RNase-resistant RNA-protein complexes of $M_r$ ~43,000 with the $^{32}$P-labeled TNFα RNA probe, while simultaneously decreasing binding of the ARE probe to the endogenous cellular $M_r$ ~80,000 protein. However, extracts from cells transfected with 10 μg of H6E.HGH3' (human TTP driven by its native promoter and intron), with the C124R mutation in the CMV.hTTP.tag construct (the third C in the first zinc finger mutated to an R) or the C147R mutation in CMV.hTTP.tag (the first C in the second zinc finger mutated to an R) zinc finger mutants exhibited no detectable ARE binding activity. This indicates that single cysteine to arginine mutations in each of the TTP zinc fingers completely prevented TTP binding to the TNFα ARE.

When the same UV cross-linked, RNase-treated extracts from cells transfected with CMV.hTTP.tag or H6E.HGH3' were immunoprecipitated with a polyclonal antibody to human TTP (DU88), or with a polyclonal antibody to mouse TTP (2640), an RNA-protein complex of $M_r$ 40,000–50,000 was precipitated. This indicates that the failure to see binding of TTP to the TNFα ARE probe in crude extracts from H6E.HGH3' transfected cells was simply due to much lower expression of the construct relative to the CMV construct. Neither antibody immunoprecipitated complexes from cells transfected with vector alone.

When the same UV cross-linked, RNase-treated extracts were immunoprecipitated with a polyclonal antibody to the epitope tag on TTP, the same RNA-protein complexes were precipitated from cells transfected with either the wild-type CMV.hTTP.tag or the S228A mutant, but only barely detectable complexes were seen in extracts from the cells transfected with either of the two zinc finger mutants in the CMV.hTTP.tag construct. The appearance of an immunoprecipitated complex of $M_r$ ~100,000 was clearly recognized by both antibodies to TTP and to the epitope tag, and most likely represented either TTP dimers or TTP complexed to a second protein of similar size as well as to the TNFα ARE probe.

To determine whether the mutant constructs used in these experiments expressed amounts of TTP protein that were equivalent to those expressed by the wild-type constructs, extracts prepared from 293 cells transfected with equivalent amounts of vector alone or either wild-type or mutant plasmids were subjected to Western blotting. Comparable amounts of fusion proteins were expressed from all four constructs, as recognized by the antibody to the epitope tag HA.11. An immunoreactive protein of $M_r$ ~100,000 was also seen by this technique, indicating that the integrity of the two zinc fingers in TTP is not required for the formation of these higher $M_r$ complexes, whether they are TTP dimers or TTP bound to another protein.

To further demonstrate that the binding of TTP to the TNFα ARE was specific, we made a mutant probe of pTNFα 1309–1332 in which five of the flanking As in the AUUUA motif of the ARE sequence were mutated to Gs (see FIG. 1B). When this radiolabeled mutant probe was UV cross-linked to the extract from CMV.hTTP.tag transfected 293 cells, there was no detectable formation of the TTP complex, while the amount of the $M_r$ ~80,000 complex was decreased but not eliminated. In contrast, the wild-type probe 1309–1332 could be readily cross-linked to TTP.

Electrophoretic Mobility Shift Assays.

The specificity of TTP binding to the TNFα ARE was also analyzed by electrophoretic mobility shift assays using TNFα3' UTR probes. Incubation of probe 1197–1350 (containing the seven AUUUA motifs and some sequence 5' to them; see FIG. 1B) with a cytosolic extract prepared from 293 cells transfected with vector alone resulted in three major RNA-protein complexes, denoted I, II and III. When extracts from cells transfected with hTTP expression constructs were used, there were changes in the mobility of RNA-protein complexes I and II, while complex III disappeared. In a separate experiment, the extract from control cells was incubated with probe 1197–1350, and RNA-protein complexes were separated in a mobility shift assay. After the gel was exposed to UV light, complexes I, II, and III were eluted and analyzed by SDS-PAGE. Complexes I and II corresponded to an ~80 kDa protein, and complex III corresponded to a ~55 kDa protein. In the mobility-shift assays, the TTP-probe complex migrated approximately in the same positions as complexes I and II (as noted above in the UV cross-linking assays, the binding of TTP to the TNFα mRNA ARE simultaneously decreased the binding of the ARE probe to the endogenous cellular $M_r$ ~80,000 protein). The same changes in protein-probe complex formation were seen when probes 1110–1325 (containing four AUUUA motifs; see FIG. 1B), 1281–1350 (containing seven AUUUA motifs), and 1309–1332 (containing only four clustered UUAUUUAUU nanomers) were used in the same assay.

In order to demonstrate that the binding of complexes I and II, and TTP, to the TNFα ARE probes was specific, we also used a 54-nt region from the c-fos 3'UTR that has a 62% AU content without any AUUUA motifs (53) in the mobility shift assay. This 54-nt probe did not form complexes I and II with cytosolic extracts prepared from 293 cells transfected with vector alone, nor did it form a binding complex with extracts from TTP-expressing cells.

When one of the cysteine residues in either the first or the second zinc finger was mutated in construct CMV.hTTP.tag, extracts prepared from 293 cells transfected with these mutants no longer changed the mobility pattern of complexes formed when probe 1197–1350 was used. Similar results were obtained when probes 1110–1325 or 1281–1350 were used.

To demonstrate that the mobility changes in complexes I and II were due to the binding of TTP to the TNFα RNA probe, an antibody to the epitope tag of the TTP fusion protein was added to the mobility shift assay. Although the antibody did not change the migration pattern of the RNA-protein complexes in extracts from control cells or from cells transfected with the two TTP zinc finger mutants, it retarded the migration of complexes formed in extracts from cells expressing either wild-type TTP or its S228A mutant. This supershift of the binding complex provided additional confirmation that the protein that bound to the RNA was TTP.

Importantly, the absence of TNFα ARE binding activity of the two TTP zinc finger mutants corresponded to their lack of effect on the conversion of TNFα mRNA to the smaller species in 293 cells. Normal amounts of the larger species of TNFα mRNA were present when CMV.mTNFα was co-transfected with either of the two TTP zinc finger mutant constructs, driven either by the CMV or the native human TTP promoter. The MAP kinase phosphorylation site mutant S228A, which retained its ability to bind to the TNFα ARE, also behaved like native TTP in promoting the shift to the smaller species of TNFα mRNA in intact 293 cells.

These experiments demonstrated the importance of the integrity of each of the zinc fingers in the binding of TTP to the TNFα ARE, as well as in the apparent deadenylation of the TNFα mRNA. These assays also indicated the importance of multiple cysteines in the zinc fingers, since mutating either the third C in the first finger or the first C in the second finger abolished TTP's RNA binding and cleavage-promoting activity.

TTP is Largely Non-Nuclear in these Experiments

We previously demonstrated by differential centrifugation techniques that TTP was almost exclusively cytosolic in normal mouse macrophages (7) and in the macrophage cell line RAW 264.7 (45), although it had previously been localized to the nucleus of both quiescent (11, 45) and serum-stimulated (11) fibroblasts. For the present study, we constructed plasmids that expressed human TTP as a fusion protein with a modified green fluorescent protein (GFP), which normally is distributed throughout the cytoplasm and nucleus; this modified GFP localizes within the cell based on the peptides fused to it (12, 39). When 293 cells were transfected with EGFP-N1 (GFP alone driven by the CMV promoter), fluorescence was present in both the nucleus and cytoplasm. However, when the TTP-GFP fusion construct was transfected into 293 cells, the fluorescence was somewhat heterogeneous and appeared to be largely non-nuclear. This was true in cells transfected with both CMV.hTTP.EGFP, or the H6E.EGFP construct in which the hTTP-GFP fusion protein expression was driven by the native human TTP promoter and intron. Both the promoter and single intron of TTP play important roles in its expression (23, 24). Similar predominantly cytosolic distribution was seen in HeLa cells transfected with the same constructs.

To determine whether the hTTP-GFP fusion protein expressed in 293 cells was biologically active in these cells, we tested its ability to bind to the TNFα ARE probe in the cell-free assays and to promote the size-shift of TNFα mRNA in the intact cells. Both activities were exhibited by the hTTP-GFP fusion protein. We also demonstrated that a single C to R mutation in either the first or second zinc finger of human TTP markedly inhibited the ability of this human TTP-GFP fusion protein to cause the size shift in TNFα mRNA in 293 cells, or to bind to the TNFα ARE in cell-free extracts. These mutations did not appear to affect the pattern of distribution of the protein in the cells.

TTP can participate in the series of steps comprising the initial deadenylation followed by the ultimate degradation of at least some of those mRNAs containing so-called type II AREs (8, 37), exemplified by TNFα, GM-CSF and IL-3 (53). It seems likely that an early or possibly the first step in this interaction is the direct, zinc finger-mediated binding of TTP to the ARE, followed by a series of unknown steps that leads ultimately to removal of the polyA tail and subsequent (or simultaneous) mRNA degradation. That these events are likely to be physiologically significant is indicated by the results of our earlier studies with the TTP knockout mice and macrophages derived from them, in which the mice developed a TNFα excess syndrome associated with increased macrophage production of TNFα, due at least in part to increased stability of the TNFα mRNA in the cells (6, 7, 46).

Figure Legend for Example 3.

FIGS. 1A and 1B. UV Cross-Linking of Human TTP to TNFα mRNA ARE Probes.

FIG. 1A: Cytosolic extracts were prepared from 293 cells transfected with either 5 μg of CMV.hTTP.tag or vector alone as described in Methods. Extract (20 μg of protein) was incubated with the indicated $^{32}$P-labeled TNFα RNA probes ($2 \times 10^6$ cpm). The numbers at the top of each set refer to the base numbers in the mouse TNFα mRNA, as shown in FIG. 1B. Probe 1110–1325 contained approximately 35% U residues; probe 1197–1300, 40%; and probe 1281–1350, 62%. Heparin and yeast tRNA were then added to decrease nonspecific binding. After UV cross-linking of the probes to cellular proteins, RNase T1 and A were added to digest probe not cross-linked to protein. The RNase-resistant RNA-protein complexes were resolved by 10% SDS-PAGE followed by autoradiography. Lanes 1: Probe alone (5,000 cpm). Lanes 2: Probe ($2 \times 10^6$ cpm) treated with RNase T1 and A. Lanes 3: Extract (20 μg of protein) from 293 cells transfected with vector alone (5 μg of DNA). Lanes 4: Extract (20 μg of protein) from 293 cells transfected with CMV.hTTP.tag (5 μg). The position of TTP cross-linked to $^{32}$P-labeled RNA is indicated by the arrow. The positions of protein molecular weight standards are indicated on the left.

FIG. 1B: Shown is a portion of the mTNFα mRNA 3'UTR (GenBank accession number X02611), from which the probes were derived. The five AU-rich nanomers are underlined. The five flanking As within the ARE that were mutated to form a non-binding probe are indicated in bold type.

REFERENCES FOR EXAMPLE 3

1. Akashi, M., G. Shaw, M. Gross, M. Saito, and H. P. Koeffler. 1991. Role of AUUUA sequences in stabilization of granulocyte-macrophage colony-stimulating factor RNA in stimulated cells. Blood 78:2005–2012.
2. Blackshear, P. J. 1984. Systems for polyacrylamide gel electrophoresis. Methods Enzymol. 104:237–255.
3. Bohjanen, P. R., B. Petryniak, C. H. June, C. B. Thompson, and T. Lindsten. 1991. An inducible cytoplasmic factor (AU-B) binds selectively to AUUUA multimers in the 3' untranslated region of lymphokine mRNA. Mol. Cell. Biol. 11:3288–3295.
4. Bohjanen, P. R., B. Petryniak, C. H. June, C. B. Thompson, and T. Lindsten. 1992. AU RNA-binding factors differ in their binding specificities and affinities. J. Biol. Chem. 267:6302–6309.
5. Caput, D., B. Beutler, K. Hartog, R. Thayer, S. Brown-Shimer, and A. Cerami. 1986. Identification of a common nucleotide sequence in the 3'-untranslated region of mRNA molecules specifying inflammatory mediators. Proc. Natl. Acad. Sci. USA 83:1670–1674.
6. Carballo, E., G. S. Gilkeson, and P. J. Blackshear. 1997. Bone marrow transplantation reproduces the tristetraprolin-deficiency syndrome in recombination activating gene-2 (−/−) mice. J. Clin. Invest. 100:986–995.
7. Carballo, E., W. S. Lai, and P. J. Blackshear. 1998. Feedback inhibition of macrophage tumor necrosis factor α (TNFα) production by tristetraprolin (TTP). Science, 281:1001–1005.
8. Chen, C.-Y. A., and A.-B. Shyu. 1995. AU-rich elements: characterization and importance in mRNA degradation. Trends Biochem. Sci. 20:465–470.
9. Cheng, J., K Tursken, Q-C. Yu, H. Schreiber, and M. Teng. 1992. Cachexia and graft-vs.-host-disease-type skin changes in keratin promoter-driven TNFα transgenic mice. Genes & Development 6:1444–1456.
10. De, J., W. S. Lai, J. Thorn, X. Liu, T. K. Blackwell, and P. J. Blackshear. 1999. Gene; in press.
11. DuBois, R. N., N. W. McLane, K. Ryder, L. F. Lau, and D. A. Nathans. 1990. Growth factor-inducible nuclear protein with a novel cysteine/histidine repetitive sequence. J. Biol. Chem. 265:19185–19191.
12. Flach, J., M. Bossie, J. Vogel, A. Corbett, T. Jinks, D. A. Willins, and P. A. Silver. 1994. A yeast RNA-binding protein shuttles between the nucleus and the cytoplasm. Mol. Cell. Biol. 50:1–12.

13. Gomperts, M., J. C. Pascall, and K. D. Brown. 1990. The nucleotide sequence of an EGF-inducible gene indicates the existence of a new family of mitogen-inducible genes. Oncogene 5:1081–1083.
14. Gueydan, C., L. Houetz, A. Marchant, A. Sels, G. Huez, and V. Kruys. 1996. Engagement of tumor necrosis factor mRNA by an endotoxin-inducible cytoplamic protein. Mol. Med. 2:479–488.
15. Hel, Z., E. Skamene, and D. Radzioch. 1996. Two distinct regions in the 3' untranslated region of tumor necrosis factor alpha mRNA form complexes with macrophage proteins. Mol. Cell. Biol. 16:5579–90.
16. Hel, Z., S. Di Marco, and D. Radzioch. 1998. Characterization of the RNA binding proteins forming complexes with a novel putative regulatory region in the 3'-UTR of TNF-α mRNA. Nucleic Acids Res. 26:2803–2812.
17. Heximer, S. P., and D. R. Forsdyke. 1993. A human putative lymphocyte $G_0/G_1$ switch gene homologous to a rodent gene encoding a zinc-binding potential transcription factor. DNA & Cell Biol. 12:73–88.
18. Katz, D. A., N. G. Theodorakis, D. W. Cleveland, T. Lindsten, and C. B. Thompson. 1994. AU-A, an RNA-binding activity distinct from hnRNP A1, is selective for AUUUA repeats and shuttles between the nucleus and the cytoplasm. Nucleic Acids Res. 22:238–46.
19. Keffer, J., L. Probert, H. Cazlaris, S. Georgopoulos, E. Kaslaris, D. Kioussis, and G. Kollias. 1991. Transgenic mice expressing tumor necrosis factor: a predictive genetic model of arthritis. EMBO J. 10:4025–4031.
20. Kim, Y.-U., H. G. Rus, S. N. Fisher, P. M. Pitha, and M. L. Shin. 1996. Binding of a protein to an AU-rich domain of tumor necrosis factor α mRNA as a 35 kDa complex and its regulation in primary rat astrocytes. Biochem. J. 316:455–460.
21. Kolodziej, P. A., and R. A. Young. 1991. Epitope tagging and protein surveillance. Methods in Enzymology 194:508–519.
22. Lai, W. S., D. J. Stumpo, and P. J. Blackshear. 1990. Rapid insulin-stimulated accumulation of an mRNA encoding a proline-rich protein. J. Biol. Chem. 265:16556–16563.
23. Lai, W. S., M. J. Thompson, G. A. Taylor, Y. Liu, and P. J. Blackshear. 1995. Promoter analysis of Zfp-36, the mitogen-inducible gene encoding the zinc finger protein tristetraprolin. J. Biol. Chem. 270:25266–25272.
24. Lai, W. S., M. J. Thompson, and P. J. Blackshear. 1998. Characteristics of the intron involvement in the mitogen-induced expression of Zfp-36. J. Biol. Chem. 273:506–517.
25. Lai, W. S., and P. J. Blackshear. Unpublished data.
26. Lewis, T., C. Gueydan, G. Huez, J.-J. Toulme, and V. Kruys. 1998. Mapping of a minimal AU-rich sequence required for lipopolysaccharide-induced binding of a 55-kDa protein on tumor necrosis factor-α mRNA. J. Biol. Chem. 273:13781–13786.
27. Ma, Q., and H. R. Herschman. 1991. A corrected sequence for the predicted protein from the mitogen-inducible TIS11 primary response gene. Oncogene 6:1277–1278.
28. Ma, Q., D. Wadleigh, T. Chi, and H. R. Herschman. 1994. The *Drosophila* TIS11 homologue encodes a developmentally regulated gene. Oncogene 9:3329–3334.
29. Ma, Q., and H. R. Herschman. 1995. The yeast homologue YTIS11, of the mammalian TIS11 gene family is a non-essential, glucose repressible gene. Oncogene 10:487–494.
30. Mello, C. C., C. Schubert, B. Draper, W. Zhang, R. Lobel, and J. R. Priess. 1996. The PIE-1 protein and germline specification in *C. elegans* embryos. Nature 382:710–712.
31. Mercer, J. F. B., and S. A. Wake. 1985. An analysis of the rate of metallothionein mRNA poly(A)-shortening using RNA blot hybridization. Nucleic Acids Res. 13:7929–7943.
32. Montague, J., and P. J. Blackshear. Unpublished data.
33. Muller, W. E., H. Slor, K Pfeifer, P. Huhn, A. Bek, S. Orsulic, H. Ushijima, and H. C. Schroder. 1992. Association of AUUUA-binding protein with A+U-rich mRNA during nucleo-cytoplasmic transport. J. Mol. Biol. 226:721–33.
34. Natesan, S., V. M. Rivera, E. Molinari, and M. Gilman. 1997. Transcriptional squelching re-examined. Nature 390:349–350.
35. Nie, X. F., K. N. Maclean, V. Kumar, I. A. McKay, and S. A. Bustin. 1995. ERF-2, the human homologue of the murine Tis11d early response gene. Gene 152:285–286.
36. Otsuka, T., A. Miyajima, N. Brown, K. Otsu, J. S. Abrams, S. Saeland, C. Caux, R. D. W. Malefijt, J. DeVries, P. Meyerson, T. Yokota, L. Gemmel, D. Rennick, F. Lee, K.-I. Arai, and T. Yokota. 1988. Isolation and characterization of an expressible cDNA encoding human IL-3. Induction of IL-3 mRNA in human T cell clones. J. Immunol. 140:2288–2295.
37. Peng, S. S.-Y., C.-Y. A. Chen, A.-B. and Shyu. 1996. Functional characterization of a non-AUUUA AU-rich element from the c-jun proto-oncogene mRNA: Evidence for a novel class of AU-rich elements. Mol. Cell. Biol. 16:1490–1499.
38. Phillips, R. S., and P. J. Blackshear. Unpublished data.
39. Rizzuto, R., M. Brini, P. Pizzo, M. Murgia, and T. Pozzan. 1995. Chimeric green fluorescent protein as a tool for visualizing subcellular organelles in living cells. Curr. Biol. 5:635–642.
40. Seydoux, G., C. C. Mello, J. Pettitt, W. B. Wood, J. R. Priess, and A. Fire. 1996. Repression of gene expression in the embryonic germ lineage of *C. elegans*. Nature 382:713–716.
41. Shaw, G., and R. Kamen. 1986. A conserved AU sequence from the 3' untranslated region of GM-CSF mRNA mediates selective mRNA degradation. Cell 46:659–667.
42. Stoecklin, G., S. Hahn, and C. Moroni. 1994. Functional hierarchy of AUUUA motifs in mediating rapid interleukin-3 mRNA decay. J. Biol. Chem. 269:28591–28597.
43. Taylor, G. A., W. S. Lai, R. J. Oakey, M. F. Seldin, T. B. Shows, R. L. Eddy Jr., and P. J. Blackshear. 1991. The human TTP protein: sequence, alignment with related proteins, and chromosomal localization of the mouse and human genes. Nucleic. Acid Res. 19:3454.
44. Taylor, G. A., M. J. Thompson, W. S. Lai and P. J. Blackshear. 1995. Phosphorylation of tristetraprolin, a potential zinc finger transcription factor, by mitogen stimulation in intact cells and by mitogen activated protein kinase in vitro. J. Biol. Chem. 270:13341–13347.
45. Taylor, G. A., M. J. Thompson, W. S. Lai, and P. J. Blackshear. 1996. Mitogens stimulate the rapid nuclear to cytosolic translocation of tristetraprolin, a potential zinc-finger transcription factor. Mol. Endocrinol. 10:140–146.
46. Taylor, G. A., E. Carballo, D. M. Lee, W. S. Lai, M. J. Thompson, D. D. Patel, D. I. Schenkman, G. S. Gilkeson, H. E. Broxmeyer, B. F. Haynes, and P. J. Blackshear. 1996. A pathogenetic role for TNFα in the syndrome of cachexia, arthritis and autoimmunity resulting from tristetraprolin (TTP) deficiency. Immunity 4:445–454.
47. Thompson, M. J., W. S. Lai, G. A. Taylor, and P. J. Blackshear. 1996. Cloning and characterization of two yeast genes encoding members of the CCCH class of zinc finger proteins: zinc-mediated impairment of cell growth. Gene 174:225–233.
48. Ulich, T. R., S. S. Shin, and J. del Castillo. 1993. Haematologic effects of TNF. Res. Immunol. 144:347–354.
49. Varnum, B. C., R. W. Lim, V. P. Sukhatme, and H. R. Herschman. 1989. Nucleotide sequence of a cDNA encoding TIS11, a message induced in Swiss 3T3 cells by the tumor promoter tetradecanoyl phorbol acetate. Oncogene 4:119–120.
50. Varnum, B. C., Q. Ma, T. Chi, B. Fletcher, and H. R. Herschman. 1991. The TIS11 primary response gene is a member of a gene family that encodes proteins with a highly conserved sequence containing an unusual Cys-His repeat. Mol. Cell. Biol. 11:1754–1758.
51. Wang, E., W. J. Ma, C. Aghajanian, and D. R. Spriggs. 1997. Posttranscriptional regulation of protein expression in human epithelial carcinoma cells by adenine-uridine-rich elements in the 3'-untranslated region of tumor necrosis factor-alpha messenger RNA. Cancer Res. 57: 5426–5433.
52. Worthington, M. T., B. T. Amann, D. Nathans, and J. M. Berg. 1996. Metal binding properties and secondary structure of the zinc-binding domain of Nup475. Proc. Natl. Acad. Sci. USA 93:13754–13759.
53. Xu, N., C.-Y. Chen, and A.-B. Shyu. 1997. Modulation of the fate of cytoplasmic mRNA by AU-rich elements: Key sequence features controlling mRNA deadenylation and decay. Mol. Cell. Biol. 17:4611–4621.

EXAMPLE 4

The Tandem Zinc Finger Domain from TTP and TTP-Related Proteins Binds to AU-Rich Elements and Destabilizes mRNA Methods 1. Plasmid Construction.

a. Parent Plasmids.

The human (21) and mouse (2) TTP cDNAs were obtained as described. The cDNAs encoding the *Xenopus* CCCH proteins XC3H-1, XC3H-3 and XC3H-4 were obtained as described (20).

b. Expression Constructs.

Human TTP expression constructs H6E.HGH3' and CMV.hTTP.tag were made as described (11). CMV.mTTP.tag, which contained the entire protein coding region of mouse TTP, was made using the same methods. CMV.hTTP (97–173).tag, CMV.hTTP(1–173).tag and CMV.hTTP (97–326).tag, which all contained the double zinc finger domain (aa 104–166 from ref 21) and part of the protein sequence of human TTP, were made as described (11).

CMV.http (97–173).tag contained essentially only the zinc fingers and seven flanking amino acids on both ends. CMV.hTTP(1–173).tag contained amino acids 1–173, and CMV.hTTP(97–326).tag contained amino acids 97–326 (the last amino acid) of human TTP.

CMV.CMG1.tag was made by inserting a PCR fragment containing the entire protein coding region of rat cMG1 (ref. 13, bp 108–1190 of GenBank accession number X52590), into the vector CMV.BGH3'/pBS+. The template cMG1 for the PCR reaction was generously provided by Dr. K. D. Brown (AFRC Institute of Physiology and Genetics Research, Babraham, Cambridge, UK). The epitope tag derived from the influenza virus hemagglutinin protein (22) was attached to the last amino acid of the cMG1 protein as described (23).

CMV.XC3H-1.tag and CMV.XC3H-3.tag were made by inserting PCR fragments containing the entire protein coding region of the corresponding *Xenopus* cDNA clones (20), as well as the epitope tag fused to the last amino acid of each protein, into the vector CMV.BGH3'/pBS+. CMV.U2AF35 was made by inserting a PCR fragment containing the entire protein coding region of the splicing factor U2AF35 (24) into the vector CMV.BGH3'/pBS+.

Plasmid pRSET B, which contained the entire coding region of U2AF35, was provided by Drs. B. R. Graveley and T. Maniatis (Harvard University, Cambridge, Mass.), and was used as a template in the PCR reaction.

CMV.mTNF containing a NarI-XbaI fragment spanning bp 127–1325 of a mouse TNF cDNA sequence (GenBank accession number X02611) was made as described (11). The mTNF cDNA clone, provided by Dr. B. Beutler (The University of Texas Southwestern Medical Center, Dallas, Tex.), contained an incomplete 3' UTR that ended at bp 1325 (GenBank accession number X02611), with 33 adenylate residues attached to the last T. This sequence is shown in FIG. 1 of reference (11).

2. Transfection of HEK 293 Cells, Northern Analysis, and Cytosolic Extract Preparation.

HEK 293 cells were maintained in minimal essential medium (Life Technologies, Inc., Gaithersburg, Md.) supplemented with 10% fetal bovine serum, 100 units/ml penicillin, and 100 µg/ml streptomycin. Transient transfection of $1.5 \times 10^6$ cells with CMV.hTTP.tag, or with expression constructs containing the protein coding regions of the other CCCH zinc finger proteins, or with vector pBS+alone in calcium-phosphate precipitates, was performed as described previously (23, 25), except that the transfection mixture was allowed to stay on the cells for 16 to 20 h, and the glycerol shock step was omitted. When cells were co-transfected with CMV.m TNF and CCCH protein expression constructs, human growth hormone expression plasmid pXGH5 (Nichols Institute Diagnostics, San Juan Capistrano, Calif.) was also co-transfected to monitor transfection efficiency.

Twenty-four h after the removal of the transfection mixture, samples were taken from the cell culture medium and human growth hormone released was assayed according to the manufacturer's protocol. Total cellular RNA was then harvested from the HEK 293 cells using the RNeasy system (Qiagen, Valencia, Calif.). Northern blots were prepared as described (2). Blots were hybridized to random-primed, –32P-labeled cDNA probes coding for various CCCH zinc finger proteins, including mouse TTP (2); *Xenopus* XC3H-1 and XC3H-3 (20); rat cMG1 (13); or splicing factor U2AF35 (24). Blots were also hybridized with a ~1 kb NarI-BglII fragment of a m TNF cDNA (11) and a ~0.3 kb fragment of mouse cyclophilin cDNA (bp 166 to 480; GenBank accession number X52803).

Cytosolic extracts were prepared from HEK 293 cells 24 h after the removal of the transfection mixture. The cells were incubated on ice for 20 min in a buffer consisting of 10 mM HEPES (pH 7.6), 3 mM $MgCl_2$, 40 mM KCl, 5% (v/v) glycerol, 0.5% (v/v) NONIDET® P-40, 2 mM DTT, 0.5 mM phenylmethylsulfonyl fluoride (PMSF) and 8 µg/ml leupeptin (lysis buffer). Lysis of the cells and maintenance of intact nuclei were carefully monitored by microscopy. The nuclei and cell membrane debris were removed by centrifugation at 16,000 g at 4° C. for 15 min. Glycerol was added to the supernatant (cytosolic extract) to 20% (v/v), and the resulting extract was stored at 70° C.

3. Analysis of RNA-Protein Complexes by Sodium Dodecyl Sulfate-Polyacrylamide Gel Electrophoresis (SDS-PAGE), Electrophoretic Mobility Shift Assay, and Western Blotting.

a. Preparation of RNA Probes

Plasmid pTNF 1281–1350 (bp 1281–1350 of GenBank accession number X02611) contained seven AUUUA motifs, five of them being overlapping UUAUUUAUU nonamers. This was constructed as described (11).

Plasmid pTNF 1309–1332 (bp 1309–1332 of GenBank accession number X02611), containing four overlapping UUAUUUAUU nonamers, was constructed by inserting double-stranded oligonucleotides spanning bp 1309–1332 into the EcoRV-XbaI cloning sites of pSK-.

Plasmid pTNF 1309–1332 (A/G) contained five Gs (underlined) replacing the five flanking As of bp 1309–1332 of GenBank accession number X02611 (UUGUUUGUUU GUUGUUUGUUUUU) (SEQ ID NO:45) and was constructed as described for pTNF 1309–1332.

Correct sequences of all plasmid inserts were confirmed by dRhodamine Terminator Cycle Sequencing (Perkin-Elmer, Foster City, Calif.).

To label RNA transcripts with $^{32}$P-UTP (800 Ci/mmol), the above plasmids linearized with XbaI were used as templates, and the Promega Riboprobe in vitro Transcription Systems protocol was employed. The resulting products were precipitated with ammonium acetate and ethanol.

b. Cross-Linking of Proteins to RNA

Cytosolic extracts prepared from HEK 293 cells transfected with CMV.hTTP.tag, or other zinc finger protein expression constructs, or vector (5 or 20 µg of protein) were incubated with $1.5 \times 10^6$ cpm of RNA probe in a 96-well plate at room temperature for 20 min in 20 µl lysis buffer (without protease inhibitors). Heparin and yeast tRNA were added to final concentrations of 2.5 µg/µl and 50 ng/µl, respectively, for an additional 10 min. The 96-well plate was then placed on ice and irradiated at 254 nm UV light in a Stratalinker (Stratagene, La Jolla, Calif.) for 30 min at a distance of 5 cm from the light source. RNA not associated with protein was digested with 100 units of RNase T1 (Life Technologies, Inc) for 20 min at room temperature, and further digested with 25 µg of RNase A (Pharmacia Biotech, Piscataway, N.J.) at 37° C. for 15 min. The remaining RNA/protein complexes were analyzed by SDS-PAGE (12% or 16% acrylamide gel) followed by autoradiography.

c. Western Blotting.

Cell extracts (5–50 µg protein) were mixed with ⅕ volume of 5×SDS sample buffer (26), boiled for 5 min, then loaded onto 12% or 16% SDS-PAGE gels. Western blotting was performed by standard techniques. Membranes were incubated in Tris-buffered saline/0.3% TWEEN® 20 (polyoxyethylene sorbitan monolaureate) (TBS/T) with either polyclonal antiserum HA.11 (1:2,500) or an antiserum to U2AF35 (27). Incubation of the membranes with second antibody and development were performed as described (8). For some blots, 125I-protein A (0.2 µCi/ml in TBS/T; Amersham, Arlington Heights, Ill.) was used in place of second antibody.

d. RNA Electrophoretic Mobility Shift Assay.

Cytosolic extracts prepared from HEK 293 cells transfected with either vector alone or expression constructs driven by the CMV promoter (5 or 20 µg of protein) were incubated with $2 \times 10^5$ cpm of RNA probe at room temperature for 20 min in 20 µl lysis buffer (without protease inhibitors). Heparin and yeast tRNA were added to final concentrations of 2.5 µg/µl and 50 ng/µl, respectively, for an additional 10 min. RNA not associated with protein was digested with 100 units of RNase T1 (Life Technologies, Inc.) for 20 min at room temperature; the reaction mixture was then loaded onto a 6% non-denaturing acrylamide gel and subjected to electrophoresis at 250 V for 90 min, in 0.4× Tris/borate/EDTA buffer.

4. Expression of XC3-H4 Protein and its Fragments in *Xenopus* Oocytes.

a. Preparation of XC3H-4 RNA In Vitro cDNAs encoding various regions of the XC3H-4 protein (20), full length (aa 1–276); from amino acids 1 to 120 (containing the tandem CCCH zinc fingers of the TTP-type); and from amino acids 121 to 276 (containing the second pair of CCCH zinc fingers) were inserted into the BglII cloning site of plasmid pSP64TEN (a gift from Dr. Douglas Melton, Harvard University, Cambridge, Mass.). The epitope tag derived from the influenza hemagglutinin protein (22) was attached to the last amino acid of each of the peptides as described (23). Correct sequence of the inserts was confirmed by dRhodamine Terminator Cycle Sequencing (Perkin-Elmer). The plasmids were linearized by XbaI digestion, and were used as templates to synthesize RNA in vitro. The RNAs were prepared with the use of the mMESSAGEmA-CHINE SP6 Kit (Ambion, Inc., Austin, Tex.) following the manufacturer's protocol.

b. Microinjection of Oocytes

Ovary was removed from adult *Xenopus* females (Xenopus I, Ann Arbor, Mich.), and stage VI oocytes were separated from the ovary and manually defolliculated. Oocytes were allowed to recover for 16 h at 18° C. in buffer OR-2 (5 mM HEPES (pH 7.8), 82.5 mM NaCl, 2.5 mM KCL, 1 mM CaCl2, 1 mM MgCl2, 3.8 mM NaOH). Oocytes were injected with 30–50 ng of mRNA and incubated for 24 h at 18° C. Oocyte cytosolic extracts were prepared as described above for 293 cell extracts.

Results

The other two human members of the mammalian CCCH double zinc finger protein family, ERF1 (cMG1, TIS11b) and ERF2 (TIS11d), share strikingly similar amino acid sequences in the tandem zinc finger (TZF) region with TTP (FIG. 2, underlined). Although the carboxyl termini exhibit some sequence similarities, there are major differences between TTP and the other two proteins, while the amino acid sequences of ERF1 and ERF2 are more closely related to each other (FIG. 2).

To determine whether these other two family members shared TTP's ability to bind to the ARE region of the TNF mRNA and destabilize it, ARE binding studies were performed using proteins expressed in HEK 293 cells, and co-transfection assays with the TNF mRNA expression construct were performed in the same cell type. Besides the TTP expression constructs, the new expression constructs used were made from rat cMG1 (113), which is the rat homologue of mouse TIS11b, human ERF1, and *Xenopus* XC3H-2; and *Xenopus* XC3H-3 (20), which is the *Xenopus* homologue of mouse TIS11d and human ERF2.

Effects of TTP-Related Proteins on TNF mRNA

In the expression studies described below, we used a previously described (11) TNF expression construct, CMV.mTNF. This construct does not contain the full 3'UTR of mTNF; instead, it ends at base 1325 (of GenBank accession number X02611) followed by 33 adenylate residues encoded by the cDNA. The expression of TNF mRNA from this construct allowed the detection of both the adenylated and deadenylated forms of this mRNA in the presence of TTP (11). TTP has similar effects on the full-length mouse TNF mRNA (data not shown), but for technical reasons involving size overlap with the 18S ribosomal RNA, these are more difficult to quantitate.

The HEK 293 cells used in the transfection experiments do not express endogenous TNF or TTP mRNA (11). Quantitation of Northern blot mRNA expression was determined by Phosphorimager, and was corrected for transfection efficiency by HGH secretion and for gel loading by quantitating endogenous cyclophillin mRNA levels. When these cells were co-transfected with CMV.mTNF and a range of concentrations of the human TTP expression construct CMV.hTTP.tag, the mTNF mRNA exhibited a characteristic expression pattern. At a low concentration of TTP DNA (0.005 µg per dish of cells), the total amount of m TNF mRNA was reduced to ~40% of control in this experiment. When the amount of co-transfected TTP DNA was increased to 0.01 µg of DNA, the total amount of hybridizeable TNF mRNA was further reduced to 23% of control. When 0.1 and 1 µg of TTP were co-transfected, a smaller species of m TNF mRNA was increased in intensity, while the upper band decreased markedly. We have previously shown by RNase H experiments that the lower band is a deadenylated species of TNF mRNA (11). At these higher concentrations of TTP DNA, the total accumulated hybridizeable mTNF mRNA was actually greater than that seen in the cells co-transfected with vector alone.

After correcting for transfection efficiency, the amounts of hybridizeable mTNF mRNA from cells co-transfected with 0.1 or 1 µg of CMV.hTTP.tag were 254% and 481% of control, respectively. The apparent decrease in hybridizable mTNF mRNA seen at the highest concentration of TTP DNA (1 µg) is likely to be due to the global inhibition of transcription seen at this level of TTP expression, as noted previously (11); this was reflected in a marked decrease in HGH expression from these cells. These results are similar to those described previously (11), in which Phosphorimager values from four independent experiments were normalized for both transfection efficiency and gel loading and then averaged. In that study, an average decrease of TNF mRNA to 17% of control was seen at 10 ng of CMV.hTTP.tag DNA; this value increased to 173% and 300% of control at 50 and 100 ng of DNA, respectively. The mechanism of the increased accumulation of the deadenylated species of TNF mRNA seen at higher TTP expression plasmid concentrations is not known, but is a consistent and highly reproducible finding (11).

In the same co-transfection experiment, we tested the ability of the two TTP-related proteins to destabilize TNF mRNA and to promote the formation of the deadenylated species. When either CMV.CMG1.tag (a rat cMG1 expression plasmid, representing the cMG1/TIS11b/ERF1 proteins) or CMV.XC3H-3.tag (a *Xenopus* XC3H-3 expression construct, representing the TIS11d/ERF2 proteins) was co-transfected with CMV.mTNF into 293 cells, each exhibited a similar pattern to TTP in influencing the accumulation of TNF mRNA. With very low amounts of co-transfected CMV.CMG1.tag DNA, 0.005 and 0.01 µg, the total hybridizeable amounts of TNF mRNA were decreased to 40% and 27% of control, respectively. The accumulation of the smaller species of TNF mRNA was obvious at 0.1 and 1 µg of co-transfected CMV.CMG1.tag DNA; total hybridizeable TNF mRNA was 106% and 663% of control, respectively. Expression of the *Xenopus* protein, XC3H-3, resulted in a similar pattern. Transfection of low concentrations of CMV.XC3H-3.tag DNA (0.005 and 0.01 µg) caused a decrease in total TNF mRNA to 57% and 49% of control, respectively. At 0.1 µg of CMV.XC3H-3.tag DNA co-transfection, the characteristic two sizes of TNF mRNA were detected, while at 1 µg of CMV.XC3H-3.tag DNA, the deadenylated species of the mRNA accumulated to 461% of control.

As a control, we used the human RNA splicing factor U2AF35 (24). This protein contains two putative zinc fingers of the CCCH class, which, instead of being 18 amino acids apart, are widely separated by 116 amino acids, and are also not preceded by the YKTEL lead-in sequence. The U2AF35 protein is the smaller subunit of the essential splicing factor U2AF (24). Its heterodimeric complex with U2AF65 is thought to be required for recognition of the 3' splice acceptor site in pre-mRNA splicing (for reviews see (28, 29)). U2AF35 has also been shown to interact with other proteins involved in splicing, such as SC35, SF2/ASF, tra and tra2, and was originally not thought to directly bind to RNA (27, 30); however, this conclusion has been revised recently (31–33). Although endogenous U2AF35 mRNA in 293 cells was readily detectable, the transfection markedly increased the expression of this mRNA and protein. In this co-transfection experiment, the TNF mRNA was not affected by the expression of increasing amounts of U2AF35. This is in contrast to the effects of two other TTPs, mouse (2) and *Xenopus* (XC3H-1 (20)), both of which behaved like their human counterpart in this assay.

Binding of CCCH Zinc Finger Proteins to the ARE of TNF mRNA

Using the 70 b $^{32}$P-labeled TNF ARE probe (bases 1281–1350 of Genbank accession number X02611), we performed UV cross-linking experiments with extracts from 293 cells that had been transfected with constructs expressing these CCCH zinc finger proteins driven by the CMV promoter. In addition to human TTP, both rat cMG1 and *Xenopus* XC3H-3) were crosslinked by the TNF ARE probe. Two major crosslinked proteins bands were formed with XC3H-3; one at Mr ~48,000, presumably representing the intact protein, and one at Mr~32,000, presumably representing a proteolytic fragment. Human U2AF35 protein, whose widely spaced zinc fingers lack the YKTEL lead-in sequence, did not form detectable complexes with the TNF ARE probe. The identities of the endogenous 293 cell proteins that cross-linked to this probe, of Mr ~85,000, ~70,000, ~46,000 and ~35,000 are unknown; their possible relationship to other ARE binding proteins described in the literature has been discussed previously (11).

The ARE binding activity of the two TTP-related proteins was also tested in RNA mobility shift assays. As we have shown (11), the TNF ARE probe formed three RNA-protein complexes (I, II and III) with a control extract prepared from 293 cells transfected with vector alone. When an extract from cells transfected with CMV.hTTP.tag was used, new complexes were formed while complexes I, II and III seen in the extract from vector-transfected cells decreased or disappeared.

Formation of new RNA-protein complexes was likewise observed when extracts from 293 cells transfected with either CMV.CMG1.tag or CMV.XC3H-3.tag were used in the assay. Considerable radioactivity also remained in the gel wells when extracts containing these two proteins were used. Human U2AF35 RNA splicing factor did not form detectable complexes with the TNF ARE probe under these conditions. Expression of these proteins from the expression constructs was readily detectable using antibodies to the epitope-tagged proteins.

Binding of TTP and Related Proteins to Mutant TNF ARE Probes

Figures 3A, 3B:
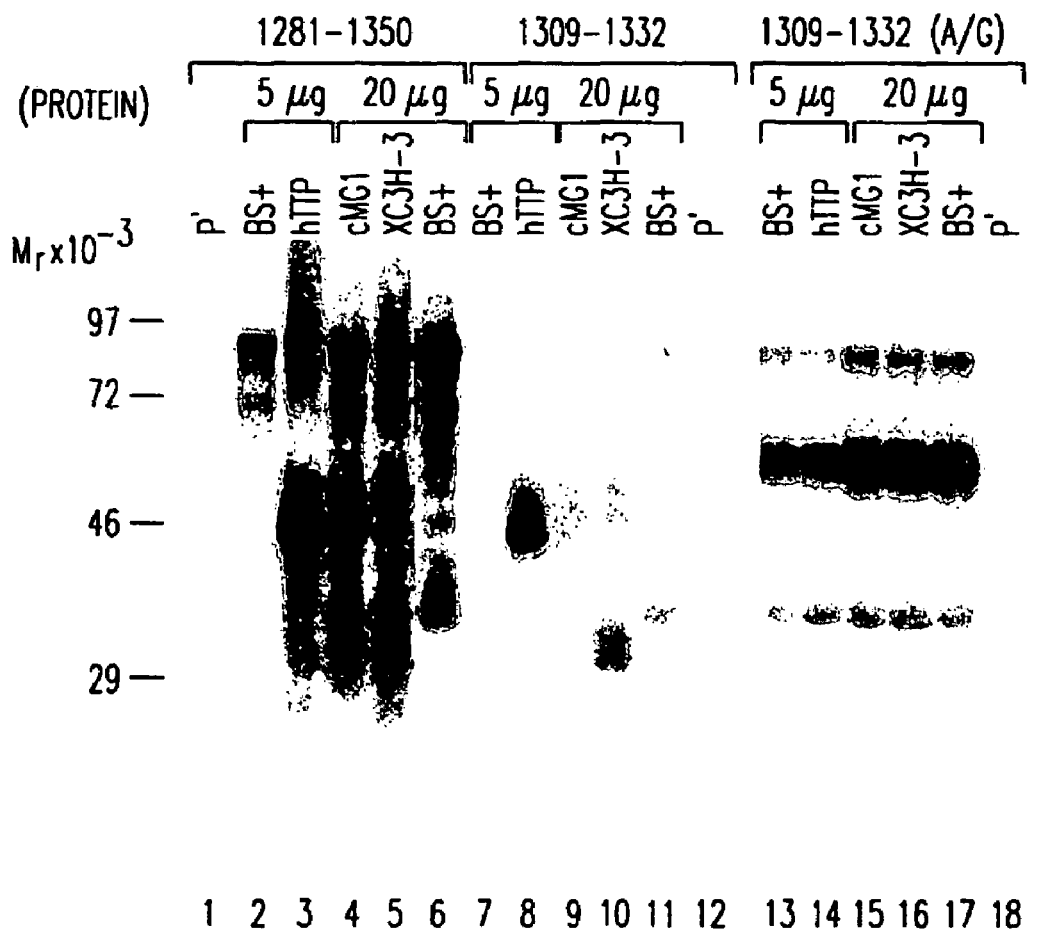
FIG. 3A is a diagram of a UV cross-linking assay showing cross-linking of TTP and TTP-related proteins with mouse TNFα mRNA ARE probes containing point mutations.
FIG. 3B is a is a diagram showing the nucleotide sequence of the mouse TNFα ARE probes used in the experiment depicted in FIG. 3A.

We previously determined that the flanking A nucleotides of the AUUUA motifs in the TNF ARE were essential for binding of TTP to the TNF ARE (11). We next evaluated the ability of the TTP-related proteins to bind to mutant ARE probes. We first compared a longer TNF ARE probe (representing b 1281 to 1350 of GenBank accession number X02611) that contained seven AUUUA motifs to a probe (b 1309–1332) that contained only four of the AUUUA sequences (FIG. 3B). Using probe 1281–1350, cytosolic complexes of Mr~85,000, ~70,000, ~46,000 and ~35,000 were seen when vector-transfected cell extracts were used; these were less apparent when the shorter probe 1309–1332 was used (FIG. 3A, compare lane 2 with 7, or lane 6 with 11). Extracts prepared from 293 cells transfected with the hTTP, cMG1, and XC3H-3 expression constructs all formed complexes with both long and short probes (FIG. 3A, lanes 3–5, 8–10).

We next studied the binding specificity of TTP and its related proteins to a mutant of the short probe 1309–1332. None of the proteins was able to form detectable complexes with probe 1309–1332 (A/G) (FIG. 3B, mutation sites indicated by triangles), a mutated ARE probe in which the flanking A residues in the AUUUA motif were substituted with Gs (FIG. 3B, lanes 13–17).

Characteristics of a Fourth CCCH Protein.

We previously identified a fourth prospective family member of the CCCH TZF protein family in *Xenopus* (accession number AAD24210 (20)). This protein, XC3H-4, contained two zinc fingers spaced 18 amino acids apart that contained all of the hallmarks of the TZF domains from the three proteins discussed above; in addition, it contained two additional, more carboxyl-terminal CCCH zinc fingers, spaced more closely together and containing more degenerate lead-in sequences (20). Database searches revealed sequence similarity to the amino terminal portions of two CCCH proteins from zebrafish (34) and carp (35). Subsequent correction of the fish DNA sequences (CAA71245.2 for carp CTH1, CAB55775.1 for zebrafish CTH1) showed apparent homology with the *Xenopus* sequence over the entire lengths of the proteins (FIG. 4). To our knowledge, mammalian homologues of these proteins have not been cloned to date.

Attempts to express the *Xenopus* member of this group, XC3H-4, or various subdomains, in 293 cells failed to yield significant levels of mRNA or protein. However, significant expression of protein was readily achieved by injecting mRNA into *Xenopus* oocytes; extracts from these oocytes were then used in ARE crosslinking studies. Using the $^{32}$P-labeled TNF ARE probe (bases 1281–1350 of GenBank accession number X02611), we performed UV cross-linking experiments with extracts from *Xenopus* oocytes that had been injected with in vitro transcribed RNAs encoding the full length, the first half (aa 1 to 120 of accession number AAD24210), or the second half (aa 121 to 276) of the XC3H-4 protein. Similar to human, mouse, or *Xenopus* (XC3H-1) TTP expressed in 293 cells, extracts prepared from oocytes injected with *Xenopus* XC3H-4 RNA that encoded the full-length protein were crosslinked by the TNF ARE probe, while no probe-protein complex was detectable when extracts of buffer-injected oocytes were used. When an extract from oocytes injected with RNA encoding the first 120 amino acids of XC3H-4 protein was used in the UV cross-linking assay, a probe-protein complex with an apparent Mr 15,000 was observed. This complex formation is presumably due to the TZF domain that is related to the one in TTP (see FIG. 5B). When an extract from oocytes injected with RNA encoding the second half of the XC3H-4 protein (aa 121–276) was used in the UV cross-linking assay, no probe-protein complex could be detected. The second half of the protein contains a pair of CCCH zinc fingers that each have the internal spacing of the TTP-type zinc fingers, but the two fingers are separated by only 7 amino acids and they lack the R(K)YKTEL lead-in sequence. Human U2AF35 protein also did not form detectable complexes with the TNF ARE probe. Expression of the XC3H-4 protein and its fragments from the RNA-injected oocytes was readily detectable using antibodies to the epitope-tagged proteins.

Interaction of TTP Fragments with TNF mRNA

As shown in FIG. 2, the human proteins ERF1 and ERF2 exhibit much greater similarity in amino acid sequence with TTP within the TZF domain than in other regions of the proteins, suggesting that the common TZF domain may be the key component of these proteins that binds to and regulates the stability of ARE-containing mRNAs. We have already shown that the integrity of both zinc fingers is necessary for TTP binding to the TNF ARE in cell-free assays, and for destabilizing TNF mRNA in cell transfection experiments (11).

We asked next whether the TZF domain alone was sufficient for TTP to interact with the TNF mRNA. Three expression constructs were prepared that all contained the TZF domain; this spans amino acids 104–166 of human TTP (21) GenBank accession number M63625). CMV.hTTP (1–173).tag contained amino acids 1–173; CMV.hTTP (97–326).tag contained amino acids 97–326 (the carboxyl terminus of the protein); and CMV.hTTP(97–173).tag contained the double zinc finger domain flanked by seven amino acids at each end.

When cell extracts from 293 cells expressing these protein fragments were used in UV cross-linking experiments using TNF ARE probes, TTP and all of its fragments could be cross-linked to a longer probe containing the full ARE (b 1281–1350) as well as a shorter probe containing only four AUUUA motifs (b 1309–1332). Neither the full-length TTP protein, nor any of its fragments, was able to form a detectable complex with the mutant probe 1309–1332 (A/G), in which the flanking As of its four AUUUA motifs were replaced by Gs.

In RNA mobility shift assays using the TNF ARE 1309–1332 probe and 293 cell extracts prepared from cells transfected with these TTP expression constructs, each of these TTP fragments, like the full-length protein, was able to form a probe-protein complex. When an epitope-tag antibody was included in the mobility shift assay, all of these TTP fragments formed super-shifted complexes, while there was no super-shifted complex formation with extracts from vector-transfected 293 cells.

Although the amount of mRNA and protein expression from these TTP fragment expression constructs was somewhat decreased relative to full-length TTP, readily detectable amounts of these fragments were seen by probing a Western blot with an antibody to the epitope tag.

We then tested the ability of these truncated forms of TTP to cause deadenylation and/or degradation of the TNF mRNA in intact cells. When 293 cells were co-transfected with CMV.m TNF and either CMV.hTTP(1–173).tag or CMV.hTTP(97–326).tag, the TNF mRNA exhibited the shortening to the deadenylated form seen with full-length TTP. When construct CMV.hTTP(97–173).tag was used, the characteristic two bands of TNF mRNA were seen at both 1 and 5 µg of transfected DNA. These data indicated that the 77 amino acid peptide containing the TZF domain alone was capable of promoting the decrease in size of the TNF mRNA, which we have attributed to its deadenylation (11). Concentration-response experiments showed that the apparent differences in potency of these constructs to promote deadenylation of the TNF mRNA appear to be due to differences in expression.

Alignment of TZF Domains of Known CCCH Proteins

Figure 5A:
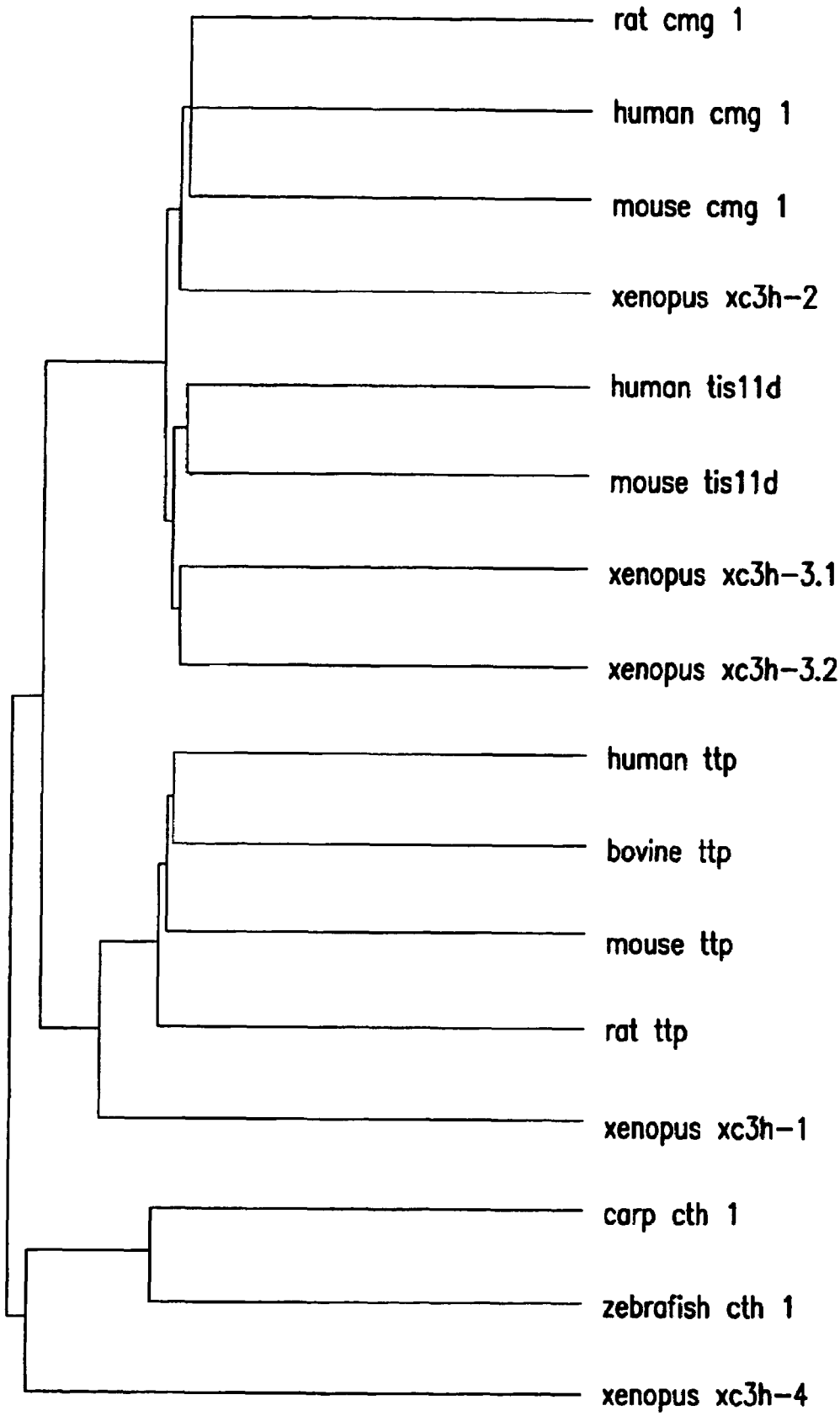
FIG. 5A is a diagram of a dendrogram showing the relatedness of amino acid sequences from the 64 amino acid tandem zinc finger domains of TTP and TTP-like polypeptides from various species.

In order to identify critical sequence requirements for ARE binding, we have begun an analysis of the TZF domain of the vertebrate CCCH proteins. We aligned the TZF domains from the four vertebrate proteins discussed here, making the assumption (borne out in every case in which it has been tested directly) that the domains from homologues from other animal species would bind to the ARE probe similarly to the prototype protein. We identified TZF domains from larger amino acid sequences already in GenBank (with one exception), as listed in the legend to FIG. 5B. The single exception is from an unpublished *Xenopus* EST, in which a single open reading frame predicted a *Xenopus* allelic variant of XC3H-33. This is now listed as XC3H-3.2, with the original allele (20) listed as XC3H-3.1. The 64 amino acid TZF domains from all of these proteins were aligned using the program Pileup from GCG. In FIG. 5A is illustrated the dendrogram produced by these alignments; despite the facts that these proteins are much more disparate outside of the TZF domains than within them, the alignment program still aligned them into homologous groups (FIG. 5A). The alignment itself is pictured in FIG. 5B. To simplify the discussion of the alignment, the amino acids within the TZF domains are numbered from 1–64.

Examination of FIG. 5B reveals that 34 of the 64 amino acids in the TZF domains (53%) have been conserved among all four proteins from species as diverse as human, *Xenopus* and zebrafish. These include the RYKTEL (SEQ ID NO:26) lead-in sequence for the first zinc finger, the lead-in sequence KYKTEL (SEQ ID NO:40) in the second zinc finger, and several other amino acids in the inter-finger 18 amino acid spacer, including a G residue at position 27, an acidic residue at 30, an L at 31, an H at 37, and a P at 38. Within both zinc fingers, the canonical CCCH residues were conserved. Within the first finger, an E residue was conserved at position 12, a G at 14, a Y at 18, a basic residue at 21, and a QFA at 23–25. Within the second finger, a G residue was conserved at position 52, a Y at 56, an R at 59, an F at 62, and a branched chain amino acid at 63.

The TZF domains also appeared to contain protein-specific "signatures", which allowed the domains from a given protein (e.g., TTP) to be grouped appropriately with its homologues (see FIG. 5A), despite the great evolutionary distance between the animal species examined. For example, TTPs from human, cow, rat, mouse, and *Xenopus* all contain T residues at position 9, S residues at position 11, A residues at position 20, N residues at position 35, HK at 46 and 47, YL at 49 and 50, and S residues at position 58, differentiating the TTP homologues from all other proteins examined. Similarly, the cMG1 homologues all contain D residues at position 20 and I residues at position 28, distinguishing them from the others. The TIS11D proteins had as their only signature an F residue at position 28. The more distantly related XC3H-4 proteins also contained signature amino acids, including SR at 8 and 9, A at 11, and L at 61.

These comparisons also identified some positions within the TZF domains that can tolerate significant amino acid diversity. For example, P, T and R were present at position 9, E and S at position 11, N, S and T at 13, A, S, T, R, and F at 15, D, E, A, and N at 20, I, F, L, P and K at 28, H, G, I, and S at 29, etc. Less diversity is evident at other positions; for example, only hydrophobic residues were present at positions 10, 48 and 49, and only basic residues were present at position 21.

Figure Legends for Example 4.

FIG. 2. Alignments of Human CCCH Zinc Finger Proteins.

The three known human (h) CCCH proteins hTTP ((21) GenBank accession number M63625), hsERF1 (11B) ((14) accession number X71901), and hsERF2 (11D) ((16) accession number X78992) sequences were aligned using ClustalW Alignments (MacVector 6.5, Oxford Molecular) with an open gap penalty of 10.0 and an extended gap penalty of 0.05. The shaded areas indicate amino acid identity. The closely related double zinc finger domains are underlined, with the key cysteine and histidine residues indicated by dots under the sequence.

FIGS. 3A and 3B. UV Cross-Linking Assays of TTP and Related Proteins with Mutant Mouse TNF-ARE Probes.

FIG. 3A: Cytosolic Extracts of 293 cells transfected with either vector alone or constructs expressing the CCCH zinc finger proteins were prepared as described in Methods. Assays used $^{32}$P-labeled m TNF ARE probes 1281–1350, 1309–1332, or a mutant of probe 1309–1332 (A/G), as indicated. Incubation of extracts (each sample in lanes 2, 3, 7, 8, 13 and 14 contained 5 μg of protein; lanes 4–6, 9–11, 15–17 contained 20 μg of protein) with $1.5 \times 10^6$ cpm of probe, UV cross-linking and RNase digestion were performed as described in Methods. Lanes 1, 12 and 18 (P', $1.5 \times 10^6$ cpm per sample): probe alone after digestion with RNase. Lanes 2, 6, 7, 11, 13 and 17 (BS+): Extracts from 293 cells transfected with 5 μg of vector plasmid. Lanes 3–5: Extracts from 293 cells transfected with 1 μg/plate of plasmid CMV.hTTP.tag, CMV.CMG1.tag, or CMV.XC3H-3.tag, respectively; vector DNA was added to make the total transfected DNA 5 μg/plate. Extracts described in lanes 3–5 were also used for lanes 8–10 and lanes 14–16. The RNA-protein complexes were resolved by SDS-PAGE (12% gel) followed by autoradiography. The exposure time for the gel using probes 1281–1350 and 1309–1332 was 4 h at −70° C., and was 8 h for the gel using 1309–1332 (A/G). The positions of molecular weight standards are indicated to the left of the gel.

FIG. 3B: The sequences of the probes used for the experiments described in FIG. 3A are shown; the adenosine residues mutated to guanosine residues in probe 1309–1332 (A/G) are indicated by the triangles.

FIG. 4. Alignments of XC3H-4-Like CCCH Zinc Finger Proteins

The three known proteins that contain four CCCH zinc fingers were aligned using ClustalW Alignments (MacVector 6.5, Oxford Molecular) with an open gap penalty of 10.0 and an extended gap penalty of 0.05. The shaded areas indicate amino acid identity, the outlined areas indicate similarities. The closely related tandem zinc finger domains are underlined, with the key cysteine and histidine residues indicated by dots under the sequence. The sequences are: Carp CTH1 ((35) GenBank accession number CAA71245.2); Zebrafish CTH1 ((34) GenBank accession number CAB55775.1); *Xenopus* XC3H-4 ((20) GenBank accession number AAD24210).

FIGS. 5A and 5B: Alignment of Tandem Zinc Finger Domains of Known CCCH Proteins.

The 64 amino acid TZF domains from the proteins described in the text were aligned with the Pileup function from GCG.

FIG. 5A shows a dendrogram is shown in which only the 64 amino acid TZF domains shown in 5B were used to calculate sequence similarities. The four major groupings are indicated.

FIG. 5B shows the alignment of the TZF domains. Identical amino acids are shaded in black; related amino acids are shaded in gray. The accession numbers for the proteins listed are as follows; for the cMG1 group: rat cMG1, X52590; human cMG1, X71901; mouse cMG1, P23950; and *Xenopus* XC3H-2, AAD24208. For the tis11d group: human TIS11 id, X78992; mouse tis11d, P23949; *Xenopus* XC3H-3.1, AAD24209; and *Xenopus* XC3H-3.23. For the TTP group: human TTP, P26651; bovine TTP, P53781; mouse TTP, P22893; rat TTP, P47973; and *Xenopus* XC3H-1, AAD24207. For the XC3H-4 group: carp CTH1, CAA71245.2; zebrafish CTH1, CAA76889; and *Xenopus* XC3H-4, AAD 24210.

REFERENCES FOR EXAMPLE 4

1. DuBois, R. N., McLane, M. W., Ryder, K., Lau, L. F., and Nathans, D. (1990) J Biol Chem 265, 19185–19191
2. Lai, W. S., Stumpo, D. J., and Blackshear, P. J. (1990) J Biol Chem 265, 16556–16563
3. Ma, Q., and Herschman, H. R. (1991) Oncogene 6, 1277–1278
4. Varnum, B. C., Lim, R. W., Sukhatme, V. P., and Herschman, H. R. (1989) Oncogene 4, 119–120
5. Taylor, G. A., Thompson, M. J., Lai, W. S., and Blackshear, P. J. (1995) J Biol Chem 270, 13341–13347
6. Taylor, G. A., Thompson, M. J., Lai, W. S., and Blackshear, P. J. (1996) Mol Endocrinol 10, 140–146
7. Taylor, G. A., Carballo, E., Lee, D. M., Lai, W. S., Thompson, M. J., Patel, D. D., Schenkman, D. I., Gilkeson, G. S., Broxmeyer, H. E., Haynes, B. F., and Blackshear, P. J. (1996) Immunity 4, 445–454
8. Carballo, E., Gilkeson, G. S., and Blackshear, P. J. (1997) J Clin Invest 100, 986–995
9. Carballo, E., Lai, W. S., and Blackshear, P. J. (1998) Science 281, 1001–1005
10. Carballo, E., Lai, W. S., and Blackshear, P. J. (2000) Blood 95, 1891–1899
11. Lai, W. S., Carballo, E., Strum, J. R., Kennington, E. A., Phillips, R. S., and Blackshear, P. J. (1999) Mol Cell Biol 19, 4311–4323
12. Barnard, R. C., Pascall, J. C., Brown, K. D., McKay, I. A., Williams, N. S., and Bustin, S. A. (1993) Nucleic Acids Res 21, 3580
13. Gomperts, M., Pascall, J. C., and Brown, K. D. (1990) Oncogene 5, 1081–1083
14. Ning, Z. Q., Norton, J. D., Li, J., and Murphy, J. J. (1997) Biochem Soc Trans 25, 306S
15. Varnum, B. C., Ma, Q. F., Chi, T. H., Fletcher, B., and Herschman, H. R. (1991) Mol Cell Biol 11, 1754–1758
16. Nie, X. F., Maclean, K. N., Kumar, V., McKay, I. A., and Bustin, S. A. (1995) Gene 152, 285–286
17. Ma, Q., Wadleigh, D., Chi, T., and Herschman, H. (1994) Oncogene 9, 3329–3334.
18. Ma, Q., and Herschman, H. R. (1995) Oncogene 10, 487–494
19. Thompson, M. J., Lai, W. S., Taylor, G. A., and Blackshear, P. J. (1996) Gene 174,225–233
20. De, J., Lai, W. S., Thorn, J. M., Goldsworthy, S. M., Liu, X., Blackwell, T. K., and Blackshear, P. J. (1999) Gene 228, 133–145
21. Taylor, G. A., Lai, W. S., Oakey, R. J., Seldin, M. F., Shows, T. B., Eddy, R. L., Jr., and Blackshear, P. J. (1991) Nucleic Acids Res 19, 3454
22. Kolodziej, P. A., and Young, R. A. (1991) Methods Enzymol 194, 508–519
23. Lai, W. S., Thompson, M. J., and Blackshear, P. J. (1998) J Biol Chem 273, 506–517
24. Zhang, M., Zamore, P. D., Carmo-Fonseca, M., Lamond, A. I., and Green, M. R. (1992) Proc Natl Acad Sci USA 89, 8769–8773
25. Lai, W. S., Thompson, M. J., Taylor, G. A., Liu, Y., and Blackshear, P. J. (1995) J Biol Chem 270, 25266–25272
26. Blackshear, P. J. (1984) Methods Enzymol 104, 237–255
27. Zuo, P., and Maniatis, T. (1996) Genes Dev 10, 1356–1368
28. Achsel, T., and Shimura, Y. (1996) J Biochem (Tokyo) 120, 53–60
29. Fu, X. D. (1995) Rna 1, 663–680
30. Gozani, O., Potashkin, J., and Reed, R. (1998) Mol Cell Biol 18, 4752–4760
31. Zorio, D. A., and Blumenthal, T. (1999) Nature 402, 835–838
32. Wu, S., Romfo, C. M., Nilsen, T. W., and Green, M. R. (1999) Nature 402, 832–835 33. Merendino, L., Guth, S., Bilbao, D., Martinez, C., and Valcarcel, J. (1999) Nature 402, 838–841
34. te Kronnie, G., Stroband, H., Schipper, H., and Samallo, J. (1999) Dev Genes Evol 209,443–446
35. Stevens, C. J., Schipper, H., Samallo, J., Stroband, H. W., and te Kronnie, T. (1998) Int J Dev Biol 42, 181–188
36. Stumpo, D. J., Bock, C. B., Tuttle, J. S., and Blackshear, P. J. (1995) Proc Natl Acad Sci USA 92, 944–948
37. Wu, M., Chen, D. F., Sasaoka, T., and Tonegawa, S. (1996) Proc Natl Acad Sci U S A 93, 2110–2115

INCORPORATION BY REFERENCE

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

OTHER EMBODIMENTS

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of identifying a compound that modulates the binding of a tristetraprolin (TTP) or a TTP-like polypeptide to an AU-rich element (ARE), comprising:

a) contacting a sample containing the TTP or the TTP-like polypeptide and an ARE with the compound, and b) detecting or measuring the binding between the ARE and the TTP or the TTP-like polypeptide, whereby an increase or decrease in the binding between the ARE and the polypeptide, relative to the binding between the ARE and the polypeptide in the absence of the compound, identifies a compound that modulates the binding of TTP or a TTP-like polypeptide to an ARE.

2. The method of claim 1, whereby an increase in the binding between the ARE and the polypeptide identifies a compound that stimulates an activity of a TTP or a TTP-like polypeptide.

3. The method of claim 2, wherein the method identifies a compound that stimulates degradation of an mRNA molecule comprising an ARE.

4. The method of claim 3, wherein the mRNA molecule encodes tumor necrosis factor-α (TNF-α).

5. The method of claim 1, whereby a decrease in the binding between the ARE and the polypeptide identifies a compound that inhibits an activity of TTP or a TTP-like polypeptide.

6. The method of claim 5, wherein the method identifies a compound that inhibits degradation of an mRNA molecule comprising an ARE.

7. The method of claim 3, wherein the mRNA molecule encodes granulocyte-macrophage stimulating factor (GM-CSF) or IL-3.

8. The method of claim 1, further comprising contacting the sample with an inhibitor of mRNA transcription prior to detecting or measuring the binding between the ARE and the polypeptide.

9. The method of claim 1, wherein the ARE is a class II ARE.

10. The method of claim 6, wherein the mRNA molecule encodes TNF-α.

11. The method of claim 6, wherein the mRNA molecule encodes GM-CSF or IL-3.

* * * * *

SEQUENCE LISTING

<160> NUMBER OF SEQ ID NOS: 48

<210> SEQ ID NO 1
<211> LENGTH: 326
<212> TYPE: PRT
<213> ORGANISM: Homo sapiens

<400> SEQUENCE: 1

```
Met Asp Leu Thr Ala Ile Tyr Glu Ser Leu Ser Leu Ser Pro Asp
 1               5                  10                  15

Val Pro Val Pro Ser Asp His Gly Gly Thr Glu Ser Ser Pro Gly Trp
            20                  25                  30

Gly Ser Ser Gly Pro Trp Ser Leu Ser Pro Ser Asp Ser Ser Pro Ser
        35                  40                  45

Gly Val Thr Ser Arg Leu Pro Gly Arg Ser Thr Ser Leu Val Glu Gly
    50                  55                  60

Arg Ser Cys Gly Trp Val Pro Pro Pro Gly Phe Ala Pro Leu Ala
65                  70                  75                  80

Pro Arg Leu Gly Pro Glu Leu Ser Pro Ser Pro Thr Ser Pro Thr Ala
                85                  90                  95

Thr Ser Thr Thr Pro Ser Arg Tyr Lys Thr Glu Leu Cys Arg Thr Phe
            100                 105                 110

Ser Glu Ser Gly Arg Cys Arg Tyr Gly Ala Lys Cys Gln Phe Ala His
        115                 120                 125

Gly Leu Gly Glu Leu Arg Gln Ala Asn Arg His Pro Lys Tyr Lys Thr
    130                 135                 140

Glu Leu Cys His Lys Phe Tyr Leu Gln Gly Arg Cys Pro Tyr Gly Ser
145                 150                 155                 160

Arg Cys His Phe Ile His Asn Pro Ser Glu Asp Leu Ala Ala Pro Gly
                165                 170                 175

His Pro Pro Val Leu Arg Gln Ser Ile Ser Phe Ser Gly Leu Pro Ser
            180                 185                 190

Gly Arg Arg Thr Ser Pro Pro Pro Gly Leu Ala Gly Pro Ser Leu
        195                 200                 205

Ser Ser Ser Ser Phe Ser Pro Ser Ser Pro Pro Pro Gly Asp
    210                 215                 220

Leu Pro Leu Ser Pro Ser Ala Phe Ser Ala Ala Pro Gly Thr Pro Leu
225                 230                 235                 240

Ala Arg Arg Asp Pro Thr Pro Val Cys Cys Pro Ser Cys Arg Arg Ala
                245                 250                 255

Thr Pro Ile Ser Val Trp Gly Pro Leu Gly Gly Leu Val Arg Thr Pro
            260                 265                 270

Ser Val Gln Ser Leu Gly Ser Asp Pro Asp Glu Tyr Ala Ser Ser Gly
        275                 280                 285

Ser Ser Leu Gly Gly Ser Asp Ser Pro Val Phe Glu Ala Gly Val Phe
    290                 295                 300

Ala Pro Pro Gln Pro Val Ala Ala Pro Arg Arg Leu Pro Ile Phe Asn
305                 310                 315                 320

Arg Ile Ser Val Ser Glu
                325
```

<210> SEQ ID NO 2
<211> LENGTH: 338
<212> TYPE: PRT

<213> ORGANISM: Homo sapiens

<400> SEQUENCE: 2

```
Met Thr Thr Thr Leu Val Ser Ala Thr Ile Phe Asp Leu Ser Glu Val
 1               5                  10                  15

Leu Cys Lys Gly Asn Lys Met Leu Asn Tyr Ser Ala Pro Ser Ala Gly
            20                  25                  30

Gly Cys Leu Leu Asp Arg Lys Ala Val Gly Thr Pro Ala Gly Gly Gly
        35                  40                  45

Phe Pro Arg Arg His Ser Val Thr Leu Pro Ser Ser Lys Phe Arg Gln
    50                  55                  60

Asn Gln Leu Leu Ser Ser Leu Lys Gly Glu Pro Ala Pro Ala Leu Ser
 65                 70                  75                  80

Ser Arg Asp Ser Arg Phe Arg Asp Arg Ser Phe Ser Glu Gly Gly Glu
                85                  90                  95

Arg Leu Leu Pro Thr Gln Lys Gln Pro Gly Gly Gly Gln Val Asn Ser
            100                 105                 110

Ser Arg Tyr Lys Thr Glu Leu Cys Arg Pro Phe Glu Glu Asn Gly Ala
        115                 120                 125

Cys Lys Tyr Gly Asp Lys Cys Gln Phe Ala His Gly Ile His Glu Leu
    130                 135                 140

Arg Ser Leu Thr Arg His Pro Lys Tyr Lys Thr Glu Leu Cys Arg Thr
145                 150                 155                 160

Phe His Thr Ile Gly Phe Cys Pro Tyr Gly Pro Arg Cys His Phe Ile
                165                 170                 175

His Asn Ala Glu Glu Arg Arg Ala Leu Ala Gly Ala Arg Asp Leu Ser
            180                 185                 190

Ala Asp Arg Pro Arg Leu Gln His Ser Phe Ser Phe Ala Gly Phe Pro
        195                 200                 205

Ser Ala Ala Ala Thr Ala Ala Thr Gly Leu Leu Asp Ser Pro Thr
    210                 215                 220

Ser Ile Thr Pro Pro Pro Ile Leu Ser Ala Asp Asp Leu Leu Gly Ser
225                 230                 235                 240

Pro Thr Leu Pro Asp Gly Thr Asn Asn Pro Phe Ala Phe Ser Ser Gln
                245                 250                 255

Glu Leu Ala Ser Leu Phe Ala Pro Ser Met Gly Leu Pro Gly Gly Gly
            260                 265                 270

Ser Pro Thr Thr Phe Leu Phe Arg Pro Met Ser Glu Ser Pro His Met
        275                 280                 285

Phe Asp Ser Pro Pro Ser Pro Gln Asp Ser Leu Ser Asp Gln Glu Gly
    290                 295                 300

Tyr Leu Ser Ser Ser Ser Ser Ser His Ser Gly Ser Asp Ser Pro Thr
305                 310                 315                 320

Leu Asp Asn Ser Arg Arg Leu Pro Ile Phe Ser Arg Leu Ser Ile Ser
                325                 330                 335

Asp Asp
```

<210> SEQ ID NO 3
<211> LENGTH: 492
<212> TYPE: PRT
<213> ORGANISM: Homo sapiens

<400> SEQUENCE: 3

```
Met Ser Thr Thr Leu Leu Ser Ala Phe Tyr Asp Val Asp Phe Leu Cys
 1               5                  10                  15
```

```
Lys Thr Glu Lys Ser Leu Ala Asn Leu Asn Leu Asn Asn Met Leu Asp
         20                  25                  30

Lys Lys Ala Val Gly Thr Pro Val Ala Ala Pro Ser Ser Gly Phe
         35                  40                  45

Ala Pro Gly Phe Leu Arg Arg His Ser Ala Ser Asn Leu His Ala Leu
 50                  55                  60

Ala His Pro Ala Pro Ser Pro Gly Ser Cys Ser Pro Lys Phe Pro Gly
 65                  70                  75                  80

Ala Ala Asn Gly Ser Ser Cys Gly Ser Ala Ala Gly Gly Pro Thr
                 85                  90                  95

Ser Tyr Gly Thr Leu Lys Glu Pro Ser Gly Gly Gly Thr Ala Leu
             100                 105                 110

Leu Asn Lys Glu Asn Lys Phe Arg Asp Arg Ser Phe Ser Glu Asn Gly
         115                 120                 125

Asp Arg Ser Gln His Leu Leu His Leu Gln Gln Gln Lys Gly Gly
 130                 135                 140

Gly Gly Ser Gln Ile Asn Ser Thr Arg Tyr Lys Thr Glu Leu Cys Arg
145                 150                 155                 160

Pro Phe Glu Glu Ser Gly Thr Cys Lys Tyr Gly Glu Lys Cys Gln Phe
                 165                 170                 175

Ala His Gly Phe His Glu Leu Arg Ser Leu Thr Arg His Pro Lys Tyr
             180                 185                 190

Lys Thr Glu Leu Cys Arg Thr Phe His Thr Ile Gly Phe Cys Pro Tyr
         195                 200                 205

Gly Pro Arg Cys His Phe Ile His Asn Ala Asp Glu Arg Arg Pro Ala
 210                 215                 220

Pro Ser Gly Gly Ala Ser Gly Asp Leu Arg Ala Phe Gly Thr Arg Asp
225                 230                 235                 240

Ala Leu His Leu Gly Phe Pro Arg Glu Pro Arg Pro Lys Leu His His
                 245                 250                 255

Ser Leu Ser Phe Ser Gly Phe Pro Ser Gly His His Gln Pro Pro Gly
             260                 265                 270

Gly Leu Glu Ser Pro Leu Leu Leu Asp Ser Pro Thr Ser Arg Thr Pro
         275                 280                 285

Pro Pro Pro Ser Cys Ser Ser Ala Ser Ser Cys Ser Ser Ser Ala Ser
290                 295                 300

Ser Cys Ser Ser Ala Ser Ala Ala Ser Thr Pro Ser Gly Thr Pro Thr
305                 310                 315                 320

Cys Cys Ala Ser Ala Ala Ala Leu Arg Leu Leu Tyr Gly Thr Gly
                 325                 330                 335

Gly Ala Glu Asp Leu Leu Ala Pro Gly Ala Pro Cys Ala Ala Cys Ser
             340                 345                 350

Ser Ala Ser Cys Ala Asn Asn Ala Phe Ala Phe Gly Pro Glu Leu Ser
         355                 360                 365

Ser Leu Ile Thr Pro Leu Ala Ile Gln Thr His Asn Phe Ala Ala Val
 370                 375                 380

Ala Ala Ala Ala Tyr Tyr Arg Ser Gln Gln Gln Gln Gln Gln Gly
385                 390                 395                 400

Leu Ala Pro Pro Ala Gln Pro Pro Ala Pro Ser Ala Thr Leu Pro
                 405                 410                 415

Ala Gly Ala Ala Ala Pro Pro Ser Pro Pro Phe Ser Phe Gln Leu Pro
             420                 425                 430
```

```
Arg Arg Leu Ser Asp Ser Pro Val Phe Asp Ala Pro Pro Ser Pro Pro
        435                 440                 445

Asp Ser Leu Ser Asp Arg Asp Ser Tyr Leu Ser Gly Ser Leu Ser Ser
        450                 455                 460

Gly Ser Leu Ser Gly Ser Glu Ser Pro Ser Leu Asp Pro Gly Arg Arg
465                 470                 475                 480

Leu Pro Ile Phe Ser Arg Leu Ser Ile Ser Asp Asp
                485                 490

<210> SEQ ID NO 4
<211> LENGTH: 276
<212> TYPE: PRT
<213> ORGANISM: Xenopus laevis

<400> SEQUENCE: 4

Met Glu Ile Ser Asn Asp Ser Leu Asp Leu Phe Ser Ser Phe Phe Pro
1               5                   10                  15

Gln Leu Ser Pro Pro Ala Asp Pro Glu Thr Pro Leu Leu Pro Ser Phe
                20                  25                  30

Ser Ala Pro Pro Lys His Leu Ser Leu Ser Ser Leu Arg Tyr Lys Thr
            35                  40                  45

Glu Leu Cys Ser Arg Tyr Ala Glu Ser Gly Phe Cys Ala Tyr Arg Asn
    50                  55                  60

Arg Cys Gln Phe Ala His Gly Leu Ser Glu Leu Arg Pro Pro Val Gln
65                  70                  75                  80

His Pro Lys Tyr Lys Thr Glu Leu Cys Arg Ser Phe His Val Leu Gly
                85                  90                  95

Thr Cys Asn Tyr Gly Leu Arg Cys Leu Phe Ile His Ser Pro Gln Glu
            100                 105                 110

Arg Arg Glu Pro Pro Val Leu Pro Asp Asn Leu Ser Leu Pro Pro Arg
        115                 120                 125

Arg Tyr Gly Gly Pro Tyr Arg Glu Arg Cys Arg Leu Trp Ser Ala Pro
130                 135                 140

Gly Gly Cys Pro Tyr Gly Ala Arg Cys His Phe Gln His Pro Lys Ser
145                 150                 155                 160

Ala Arg Glu Thr Cys Arg His Phe Ala Ala Leu Gly Asp Cys Pro Tyr
                165                 170                 175

Gly Ala Cys Cys His Phe Ser His Ser Pro Leu Asp Arg Trp Gly
            180                 185                 190

Ser Gly Thr Lys Asn Ser Ser Gly Ser Leu Ser Pro Ser Asp Pro Asp
        195                 200                 205

Ser Asp Pro Asp Thr Pro Val Leu Ser Glu Ser Pro Ala Asn Asn Ala
    210                 215                 220

Phe Ser Phe Ser Ser Leu Leu Pro Leu Ala Leu Arg Leu Gln Ile
225                 230                 235                 240

Leu Gly Asp Asp Asp Leu Pro Thr Ala Ser Asp Pro Leu Pro Gly Asp
                245                 250                 255

Asp Thr Asp Leu Leu Pro Gly Asp Glu Glu Ile Ala Gln Gly Leu Leu
            260                 265                 270

Ser Val Leu Gly
        275

<210> SEQ ID NO 5
<211> LENGTH: 327
<212> TYPE: PRT
<213> ORGANISM: Cyprinas carpio
```

<400> SEQUENCE: 5

```
Met Phe Glu Thr Ser Thr Asp Asn Leu Phe Leu Phe Pro Thr Glu Gly
1               5                   10                  15

Leu Asn Glu Ala Phe Phe Pro Glu Glu Gly Leu Ala Ser Gly Ser Leu
            20                  25                  30

Ser Leu Ala Lys Ala Leu Leu Pro Leu Val Glu Ser Pro Ser Pro Pro
        35                  40                  45

Met Thr Pro Trp Leu Cys Ser Thr Arg Tyr Lys Thr Glu Leu Cys Ser
    50                  55                  60

Arg Tyr Ala Glu Thr Gly Thr Cys Lys Tyr Ala Glu Arg Cys Gln Phe
65                  70                  75                  80

Ala His Gly Leu His Asp Leu His Val Pro Ser Arg His Pro Lys Tyr
                85                  90                  95

Lys Thr Glu Leu Cys Arg Thr Tyr His Thr Ala Gly Tyr Cys Val Tyr
            100                 105                 110

Gly Thr Arg Cys Leu Phe Val His Asn Leu Lys Glu Gln Arg Pro Val
        115                 120                 125

Arg Gln Arg Cys Arg Asn Val Pro Cys Arg Thr Phe Arg Ala Phe Gly
130                 135                 140

Val Cys Pro Phe Gly Thr Arg Cys His Phe Leu His Val Glu Gly Gly
145                 150                 155                 160

Ser Glu Ser Asp Gly Gly Glu Glu Gln Thr Cys Gln Pro Met Ser
                165                 170                 175

Gln Ser Gln Glu Trp Lys Pro Arg Gly Ala Leu Cys Arg Thr Phe Ser
            180                 185                 190

Ala Phe Gly Phe Cys Leu Tyr Gly Thr Arg Cys Arg Phe Gln His Gly
        195                 200                 205

Leu Pro Asn Ser Ile Lys Gly Val Asn Ser Thr His Thr Ser Trp Pro
    210                 215                 220

His Gln Met Thr Asn Arg Gly Ser Leu Ser Pro Val Ser Asp Ala Cys
225                 230                 235                 240

Ser Ser Gln Ser Pro Ser Ser Val Pro Ser Val Cys Val Gly Phe
                245                 250                 255

Ala Val Tyr Pro Glu Gly Ser Gly Pro Val Thr Pro Ser Val Glu
            260                 265                 270

Ala Val Ala Asn Asn Ala Phe Thr Phe Ser Ser Gln His Leu Asn Asp
        275                 280                 285

Leu Leu Leu Pro Leu Ala Leu Arg Leu Gln Gln Leu Glu Asn Val Thr
    290                 295                 300

Asn Ala Gly Pro Gln Asp Ala Val Asp Lys Pro Leu Leu Leu Ser Leu
305                 310                 315                 320

Trp Gln Asp Asp Pro Arg Ser
                325
```

<210> SEQ ID NO 6
<211> LENGTH: 319
<212> TYPE: PRT
<213> ORGANISM: Danio rerio

<400> SEQUENCE: 6

```
Met Phe Glu Thr Ser Gln Asp Asp Leu Phe Leu Phe Pro Thr Glu Gly
1               5                   10                  15

Leu Asn Glu Ala Phe Phe Pro Glu Glu Gly Leu Gly Gly Gly Gly Gly
            20                  25                  30
```

-continued

```
Gly Leu Ser Leu Ala Glu Ala Leu Pro Leu Val Glu Ser Pro Ser
            35                  40                  45

Pro Pro Met Thr Pro Trp Leu Cys Ser Thr Arg Tyr Lys Thr Glu Leu
 50                  55                  60

Cys Ser Arg Tyr Ala Glu Thr Gly Thr Cys Lys Tyr Ala Glu Arg Cys
 65                  70                  75                  80

Gln Phe Ala His Gly Leu His Asp Leu His Val Pro Ser Arg His Pro
                 85                  90                  95

Lys Tyr Lys Thr Glu Leu Cys Arg Thr Tyr His Thr Ala Gly Tyr Cys
            100                 105                 110

Val Tyr Gly Thr Arg Cys Leu Phe Val His Asn Leu Lys Glu Gln Arg
            115                 120                 125

Pro Ile Arg Pro Arg Arg Asn Val Pro Cys Arg Thr Phe Arg Ala
            130                 135                 140

Phe Gly Val Cys Pro Phe Gly Asn Arg Cys His Phe Leu His Val Glu
145                 150                 155                 160

Gly Gly Ser Glu Ser Asp Gly Ala Glu Glu Gln Thr Trp Gln Pro
                165                 170                 175

Pro Ser Gln Ser Gln Glu Trp Lys Pro Arg Gly Ala Leu Cys Arg Thr
                180                 185                 190

Phe Ser Ala Phe Gly Phe Cys Leu Tyr Gly Thr Arg Cys Arg Phe Gln
            195                 200                 205

His Gly Leu Pro Asn Thr Ile Lys Gly His Asn Ala Asn His Thr Ser
            210                 215                 220

Trp Pro Gln Gln Met Thr Asn Gly Gly Ser Ile Ser Pro Ile Ser Asp
225                 230                 235                 240

Thr Cys Thr Ser Pro Ser Pro Ser Ser Pro Thr Ser Ala Leu
                245                 250                 255

Pro Ser Pro Val Tyr Pro Asp Ser Ser Gly Pro Ile Thr Pro Pro Ser
                260                 265                 270

Val Glu Ala Val Ala Asn Asn Ala Phe Thr Phe Ser Ser Gln His Leu
            275                 280                 285

Asn Asp Leu Leu Leu Pro Leu Ala Leu Arg Leu Gln Gln Leu Glu Lys
            290                 295                 300

Ala Ala Ser Ala Gly Pro Gln Asp Val Leu Asp Lys Pro Leu Leu
305                 310                 315
```

<210> SEQ ID NO 7
<211> LENGTH: 64
<212> TYPE: PRT
<213> ORGANISM: Rattus norvegicus

<400> SEQUENCE: 7

```
Arg Tyr Lys Thr Glu Leu Cys Arg Pro Phe Glu Glu Asn Gly Ala Cys
 1               5                  10                  15

Lys Tyr Gly Asp Lys Cys Gln Phe Ala His Gly Ile His Glu Leu Arg
             20                  25                  30

Ser Leu Thr Arg His Pro Lys Tyr Lys Thr Glu Leu Cys Arg Thr Phe
            35                  40                  45

His Thr Ile Gly Phe Cys Pro Tyr Gly Pro Arg Cys His Phe Ile His
            50                  55                  60
```

<210> SEQ ID NO 8
<211> LENGTH: 64
<212> TYPE: PRT

<213> ORGANISM: Homo sapiens

<400> SEQUENCE: 8

```
Arg Tyr Lys Thr Glu Leu Cys Arg Pro Phe Glu Glu Asn Gly Ala Cys
 1               5                  10                  15
Lys Tyr Gly Asp Lys Cys Gln Phe Ala His Gly Ile His Glu Leu Arg
            20                  25                  30
Ser Leu Thr Arg His Pro Lys Tyr Lys Thr Glu Leu Cys Arg Thr Phe
        35                  40                  45
His Thr Ile Gly Phe Cys Pro Tyr Gly Pro Arg Cys His Phe Ile His
    50                  55                  60
```

<210> SEQ ID NO 9
<211> LENGTH: 64
<212> TYPE: PRT
<213> ORGANISM: Mus musculus

<400> SEQUENCE: 9

```
Arg Tyr Lys Thr Glu Leu Cys Arg Pro Phe Glu Glu Asn Gly Ala Cys
 1               5                  10                  15
Lys Tyr Gly Asp Lys Cys Gln Phe Ala His Gly Ile His Glu Leu Arg
            20                  25                  30
Ser Leu Thr Arg His Pro Lys Tyr Lys Thr Glu Leu Cys Arg Thr Phe
        35                  40                  45
His Thr Ile Gly Phe Cys Pro Tyr Gly Pro Arg Cys His Phe Ile His
    50                  55                  60
```

<210> SEQ ID NO 10
<211> LENGTH: 64
<212> TYPE: PRT
<213> ORGANISM: Xenopus laevis

<400> SEQUENCE: 10

```
Arg Tyr Lys Thr Glu Leu Cys Arg Pro Phe Glu Glu Asn Gly Ser Cys
 1               5                  10                  15
Lys Tyr Gly Asp Lys Cys Gln Phe Ala His Gly Ile His Glu Leu Arg
            20                  25                  30
Ser Leu Thr Arg His Pro Lys Tyr Lys Thr Glu Leu Cys Arg Thr Phe
        35                  40                  45
His Thr Ile Gly Phe Cys Pro Tyr Gly Pro Arg Cys His Phe Ile His
    50                  55                  60
```

<210> SEQ ID NO 11
<211> LENGTH: 64
<212> TYPE: PRT
<213> ORGANISM: Homo sapiens

<400> SEQUENCE: 11

```
Arg Tyr Lys Thr Glu Leu Cys Arg Pro Phe Glu Glu Ser Gly Thr Cys
 1               5                  10                  15
Lys Tyr Gly Glu Lys Cys Gln Phe Ala His Gly Phe His Glu Leu Arg
            20                  25                  30
Ser Leu Thr Arg His Pro Lys Tyr Lys Thr Glu Leu Cys Arg Thr Phe
        35                  40                  45
His Thr Ile Gly Phe Cys Pro Tyr Gly Pro Arg Cys His Phe Ile His
    50                  55                  60
```

<210> SEQ ID NO 12
<211> LENGTH: 64

```
<212> TYPE: PRT
<213> ORGANISM: Mus musculus

<400> SEQUENCE: 12

Arg Tyr Lys Thr Glu Leu Cys Arg Pro Phe Glu Glu Ser Gly Thr Cys
 1               5                  10                  15

Lys Tyr Gly Glu Lys Cys Gln Phe Ala His Gly Phe His Glu Leu Arg
             20                  25                  30

Ser Leu Thr Arg His Pro Lys Tyr Lys Thr Glu Leu Cys Arg Thr Phe
         35                  40                  45

His Thr Ile Gly Phe Cys Pro Tyr Gly Pro Arg Cys His Phe Ile His
     50                  55                  60

<210> SEQ ID NO 13
<211> LENGTH: 64
<212> TYPE: PRT
<213> ORGANISM: Xenopus laevis

<400> SEQUENCE: 13

Arg Tyr Lys Thr Glu Leu Cys Arg Pro Phe Glu Glu Asn Gly Ala Cys
 1               5                  10                  15

Lys Tyr Gly Glu Lys Cys Gln Phe Ala His Gly Phe His Glu Leu Arg
             20                  25                  30

Ser Leu Thr Arg His Pro Lys Tyr Lys Thr Glu Leu Cys Arg Thr Phe
         35                  40                  45

His Thr Ile Gly Phe Cys Pro Tyr Gly Pro Arg Cys His Phe Ile His
     50                  55                  60

<210> SEQ ID NO 14
<211> LENGTH: 64
<212> TYPE: PRT
<213> ORGANISM: Xenopus laevis

<400> SEQUENCE: 14

Arg Tyr Lys Thr Glu Leu Cys Arg Pro Phe Glu Glu Ser Gly Ala Cys
 1               5                  10                  15

Lys Tyr Gly Glu Lys Cys Gln Phe Ala His Gly Phe His Glu Leu Arg
             20                  25                  30

Ser Leu Thr Arg His Pro Lys Tyr Lys Thr Glu Leu Cys Arg Thr Phe
         35                  40                  45

His Thr Ile Gly Phe Cys Pro Tyr Gly Pro Arg Cys His Phe Ile His
     50                  55                  60

<210> SEQ ID NO 15
<211> LENGTH: 64
<212> TYPE: PRT
<213> ORGANISM: Homo sapiens

<400> SEQUENCE: 15

Arg Tyr Lys Thr Glu Leu Cys Arg Thr Phe Ser Glu Ser Gly Arg Cys
 1               5                  10                  15

Arg Tyr Gly Ala Lys Cys Gln Phe Ala His Gly Leu Gly Glu Leu Arg
             20                  25                  30

Gln Ala Asn Arg His Pro Lys Tyr Lys Thr Glu Leu Cys His Lys Phe
         35                  40                  45

Tyr Leu Gln Gly Arg Cys Pro Tyr Gly Ser Arg Cys His Phe Ile His
     50                  55                  60

<210> SEQ ID NO 16
```

<211> LENGTH: 64
<212> TYPE: PRT
<213> ORGANISM: Bos taurus

<400> SEQUENCE: 16

Arg Tyr Lys Thr Glu Leu Cys Arg Thr Phe Ser Glu Ser Gly Arg Cys
1               5                   10                  15

Arg Tyr Gly Ala Lys Cys Gln Phe Ala His Gly Leu Gly Glu Leu Arg
            20                  25                  30

Gln Ala Asn Arg His Pro Lys Tyr Lys Thr Glu Leu Cys His Lys Phe
        35                  40                  45

Tyr Leu Gln Gly Arg Cys Pro Tyr Gly Ser Arg Cys His Phe Ile His
    50                  55                  60

<210> SEQ ID NO 17
<211> LENGTH: 64
<212> TYPE: PRT
<213> ORGANISM: Mus musculus

<400> SEQUENCE: 17

Arg Tyr Lys Thr Glu Leu Cys Arg Thr Tyr Ser Glu Ser Gly Arg Cys
1               5                   10                  15

Arg Tyr Gly Ala Lys Cys Gln Phe Ala His Gly Leu Gly Glu Leu Arg
            20                  25                  30

Gln Ala Asn Arg His Pro Lys Tyr Lys Thr Glu Leu Cys His Lys Phe
        35                  40                  45

Tyr Leu Gln Gly Arg Cys Pro Tyr Gly Ser Arg Cys His Phe Ile His
    50                  55                  60

<210> SEQ ID NO 18
<211> LENGTH: 64
<212> TYPE: PRT
<213> ORGANISM: Rattus norvegicus

<400> SEQUENCE: 18

Arg Tyr Lys Thr Glu Leu Cys Arg Thr Tyr Ser Glu Ser Gly Arg Cys
1               5                   10                  15

Arg Tyr Gly Ala Lys Cys Gln Phe Ala His Gly Pro Gly Glu Leu Arg
            20                  25                  30

Gln Ala Asn Arg His Pro Lys Tyr Lys Thr Glu Leu Cys His Lys Phe
        35                  40                  45

Tyr Leu Gln Gly Arg Cys Pro Tyr Gly Ser Arg Cys His Phe Ile His
    50                  55                  60

<210> SEQ ID NO 19
<211> LENGTH: 64
<212> TYPE: PRT
<213> ORGANISM: Xenopus laevis

<400> SEQUENCE: 19

Arg Tyr Lys Thr Glu Leu Cys Arg Thr Phe Ser Glu Thr Gly Thr Cys
1               5                   10                  15

Lys Tyr Gly Ala Lys Cys Gln Phe Ala His Gly Lys Ile Glu Leu Arg
            20                  25                  30

Glu Pro Asn Arg His Pro Lys Tyr Lys Thr Glu Leu Cys His Lys Phe
        35                  40                  45

Tyr Leu Tyr Gly Glu Cys Pro Tyr Gly Ser Arg Cys Asn Phe Ile His
    50                  55                  60

-continued

```
<210> SEQ ID NO 20
<211> LENGTH: 64
<212> TYPE: PRT
<213> ORGANISM: Cyprinus carpio

<400> SEQUENCE: 20

Arg Tyr Lys Thr Glu Leu Cys Ser Arg Tyr Ala Glu Thr Gly Thr Cys
1               5                   10                  15

Lys Tyr Ala Glu Arg Cys Gln Phe Ala His Gly Leu His Asp Leu His
                20                  25                  30

Val Pro Ser Arg His Pro Lys Tyr Lys Thr Glu Leu Cys Arg Thr Tyr
            35                  40                  45

His Thr Ala Gly Tyr Cys Val Tyr Gly Thr Arg Cys Leu Phe Val His
        50                  55                  60

<210> SEQ ID NO 21
<211> LENGTH: 64
<212> TYPE: PRT
<213> ORGANISM: Danio rerio

<400> SEQUENCE: 21

Arg Tyr Lys Thr Glu Leu Cys Ser Arg Tyr Ala Glu Thr Gly Thr Cys
1               5                   10                  15

Lys Tyr Ala Glu Arg Cys Gln Phe Ala His Gly Leu His Asp Leu His
                20                  25                  30

Val Pro Ser Arg His Pro Lys Tyr Lys Thr Glu Leu Cys Arg Thr Tyr
            35                  40                  45

His Asn Ala Gly Tyr Cys Val Tyr Val Thr Arg Cys Leu Phe Val His
        50                  55                  60

<210> SEQ ID NO 22
<211> LENGTH: 64
<212> TYPE: PRT
<213> ORGANISM: Xenopus laevis

<400> SEQUENCE: 22

Arg Tyr Lys Thr Glu Leu Cys Ser Arg Tyr Ala Glu Ser Gly Phe Cys
1               5                   10                  15

Ala Tyr Arg Asn Arg Cys Gln Phe Ala His Gly Leu Ser Glu Leu Arg
                20                  25                  30

Pro Pro Val Gln His Pro Lys Tyr Lys Thr Glu Leu Cys Arg Ser Phe
            35                  40                  45

His Val Leu Gly Thr Cys Asn Tyr Gly Leu Arg Cys Leu Phe Ile His
        50                  55                  60

<210> SEQ ID NO 23
<211> LENGTH: 77
<212> TYPE: PRT
<213> ORGANISM: Homo sapiens

<400> SEQUENCE: 23

Thr Ser Thr Thr Pro Ser Arg Tyr Lys Thr Glu Leu Cys Arg Thr Phe
1               5                   10                  15

Ser Glu Ser Gly Arg Cys Arg Tyr Gly Ala Lys Cys Gln Phe Ala His
                20                  25                  30

Gly Leu Gly Glu Leu Arg Gln Ala Asn Arg His Pro Lys Tyr Lys Thr
            35                  40                  45

Glu Leu Cys His Lys Phe Tyr Leu Gln Gly Arg Cys Pro Tyr Gly Ser
        50                  55                  60
```

Arg Cys His Phe Ile His Asn Pro Ser Glu Asp Leu Ala
65                  70                  75

<210> SEQ ID NO 24
<211> LENGTH: 241
<212> TYPE: RNA
<213> ORGANISM: Mus musculus

<400> SEQUENCE: 24
gaauucacug gagccucgaa uguccauucc ugaguucugc aaagggagag uggucagguu     60
gccucugucu cagaaugagg cuggauaaga ucucaggccu uccuaccuuc agaccuuucc    120
agacucuucc cugaggugca augcacagcc uuccucacag agccagcccc ccucuauuua    180
uauuugcacu uauuauuuau uauuuauuua uuauuuauuu auuugcuuau gaauguauuu    240
a                                                                    241

<210> SEQ ID NO 25
<211> LENGTH: 70
<212> TYPE: RNA
<213> ORGANISM: Mus musculus

<400> SEQUENCE: 25
cucuauuuau auuugcacuu auuauuuauu auuuauuuau uauuuauuua uuugcuuaug     60
aauguauuua                                                            70

<210> SEQ ID NO 26
<211> LENGTH: 6
<212> TYPE: PRT
<213> ORGANISM: Homo sapiens

<400> SEQUENCE: 26

Arg Tyr Lys Thr Glu Leu
1               5

<210> SEQ ID NO 27
<211> LENGTH: 6
<212> TYPE: PRT
<213> ORGANISM: Homo sapiens
<220> FEATURE:
<221> NAME/KEY: VARIANT
<222> LOCATION: 1
<223> OTHER INFORMATION: Xaa can be Arg or Lys

<400> SEQUENCE: 27

Xaa Tyr Lys Thr Glu Leu
1               5

<210> SEQ ID NO 28
<211> LENGTH: 27
<212> TYPE: DNA
<213> ORGANISM: Mus Musculus

<400> SEQUENCE: 28
gtcgacactc agagagaaag gctaagg                                         27

<210> SEQ ID NO 29
<211> LENGTH: 23
<212> TYPE: DNA
<213> ORGANISM: Mus musculus

<400> SEQUENCE: 29
cattcaaagg ggatatcagt cag                                             23

```
<210> SEQ ID NO 30
<211> LENGTH: 27
<212> TYPE: DNA
<213> ORGANISM: Homo sapiens

<400> SEQUENCE: 30
gtggcttcta gatgcatggg tggcatc                                27

<210> SEQ ID NO 31
<211> LENGTH: 29
<212> TYPE: DNA
<213> ORGANISM: Homo sapiens

<400> SEQUENCE: 31
gaaggacacc tctagagaca aaatgatgc                              29

<210> SEQ ID NO 32
<211> LENGTH: 23
<212> TYPE: DNA
<213> ORGANISM: Mus musculus

<400> SEQUENCE: 32
ctttccgaat tcactggagc ctc                                    23

<210> SEQ ID NO 33
<211> LENGTH: 29
<212> TYPE: DNA
<213> ORGANISM: Mus musculus

<400> SEQUENCE: 33
tagatctaga agcgatcttt atttctctc                              29

<210> SEQ ID NO 34
<211> LENGTH: 20
<212> TYPE: DNA
<213> ORGANISM: Mus musculus

<400> SEQUENCE: 34
gataagatct caggccttcc                                        20

<210> SEQ ID NO 35
<211> LENGTH: 27
<212> TYPE: DNA
<213> ORGANISM: Mus musculus

<400> SEQUENCE: 35
gccttctaga taaatacatt cataagc                                27

<210> SEQ ID NO 36
<211> LENGTH: 27
<212> TYPE: DNA
<213> ORGANISM: Homo sapiens

<400> SEQUENCE: 36
gtggcttcta gatgcatggg tggcatc                                27

<210> SEQ ID NO 37
<211> LENGTH: 29
<212> TYPE: DNA
<213> ORGANISM: Homo sapiens

<400> SEQUENCE: 37
gaaggacacc tctagagaca aaatgatgc                              29
```

<210> SEQ ID NO 38
<211> LENGTH: 30
<212> TYPE: DNA
<213> ORGANISM: Mus musculus

<400> SEQUENCE: 38
ctgatctaga agtgcaaata taaatagagg                                    30

<210> SEQ ID NO 39
<211> LENGTH: 27
<212> TYPE: DNA
<213> ORGANISM: Mus musculus

<400> SEQUENCE: 39
gactggatcc tctatttata tttgcac                                       27

<210> SEQ ID NO 40
<211> LENGTH: 6
<212> TYPE: PRT
<213> ORGANISM: Homo sapiens

<400> SEQUENCE: 40

Lys Tyr Lys Thr Glu Leu
1               5

<210> SEQ ID NO 41
<211> LENGTH: 24
<212> TYPE: RNA
<213> ORGANISM: Mus musculus

<400> SEQUENCE: 41
uuauuuauuu auuauuuauu uauu                                          24

<210> SEQ ID NO 42
<211> LENGTH: 7
<212> TYPE: PRT
<213> ORGANISM: Homo sapiens

<400> SEQUENCE: 42

Arg Tyr Lys Thr Glu Leu Cys
1               5

<210> SEQ ID NO 43
<211> LENGTH: 6
<212> TYPE: PRT
<213> ORGANISM: Homo sapiens

<400> SEQUENCE: 43

Cys Gln Phe Ala His Gly
1               5

<210> SEQ ID NO 44
<211> LENGTH: 9
<212> TYPE: PRT
<213> ORGANISM: Homo sapiens

<400> SEQUENCE: 44

His Pro Lys Tyr Lys Thr Glu Leu Cys
1               5

<210> SEQ ID NO 45
<211> LENGTH: 24
<212> TYPE: RNA

```
<213> ORGANISM: Artificial Sequence
<220> FEATURE:
<223> OTHER INFORMATION: Description of Artificial Sequence; note =
      synthetic construct

<400> SEQUENCE: 45
uuguuuguuu guuguuuguu uuuu                                          24

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2-9, 11, 13, 16, 19, 21
<223> OTHER INFORMATION: Xaa = any amino acid
<220> FEATURE:
<221> NAME/KEY: VARIANT
<222> LOCATION: 17
<223> OTHER INFORMATION: Xaa can be Arg or Lys

<400> SEQUENCE: 46

Cys Xaa Xaa Xaa Xaa Xaa Xaa Xaa Xaa Gly Xaa Cys Xaa Tyr Gly Xaa
 1               5                  10                  15

Xaa Cys Xaa Phe Xaa His
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2-9, 11-15, 17-19
<223> OTHER INFORMATION: Xaa = any amino acid

<400> SEQUENCE: 47

Cys Xaa Xaa Xaa Xaa Xaa Xaa Xaa Xaa Cys Xaa Xaa Xaa Xaa Xaa Cys
 1               5                  10                  15

Xaa Xaa Xaa His
            20

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 48

Cys Cys Cys His
 1
```